United States Patent
Park et al.

(10) Patent No.: US 9,705,088 B2
(45) Date of Patent: Jul. 11, 2017

(54) TRIAZINE-BASED COMPOUNDS AND ORGANIC LIGHT-EMITTING DEVICES INCLUDING TRIAZINE-BASED COMPOUNDS

(71) Applicant: SAMSUNG DISPLAY CO., LTD., Yongin, Gyeonggi-Do (KR)

(72) Inventors: Jun-Ha Park, Yongin (KR); Young-Kook Kim, Yongin (KR); Eun-Young Lee, Yongin (KR); Eun-Jae Jeong, Yongin (KR); Seok-Hwan Hwang, Yongin (KR)

(73) Assignee: Samsung Display Co., Ltd., Yongin-si (KR)

(*) Notice: Subject to any disclaimer, the term of this patent is extended or adjusted under 35 U.S.C. 154(b) by 478 days.

(21) Appl. No.: 14/290,950

(22) Filed: May 29, 2014

(65) Prior Publication Data
US 2015/0171336 A1   Jun. 18, 2015

(30) Foreign Application Priority Data
Dec. 13, 2013  (KR) .................. 10-2013-0155641

(51) Int. Cl.
*H01L 51/50* (2006.01)
*H01L 51/00* (2006.01)
(Continued)

(52) U.S. Cl.
CPC ........ *H01L 51/0067* (2013.01); *C07D 403/04* (2013.01); *C09K 11/06* (2013.01);
(Continued)

(58) Field of Classification Search
None
See application file for complete search history.

(56) References Cited

U.S. PATENT DOCUMENTS

| 5,645,948 A | 7/1997 | Shi et al. |
| 2004/0053069 A1 | 3/2004 | Sotoyama et al. |

(Continued)

FOREIGN PATENT DOCUMENTS

| JP | 10-17860 | 1/1998 |
| JP | 11-087067 | 3/1999 |

(Continued)

OTHER PUBLICATIONS

Chihaya, Adachi et al., *Confinement of charge carriers and molecular excitons within 5nmthick emitter layer in organic electroluminescent devices with a double heterostructure*, Applied Physics Letters, 57 (6), Aug. 6, 1990, American Institute of Physics, 531-533.

(Continued)

*Primary Examiner* — Gregory Clark
(74) *Attorney, Agent, or Firm* — Lewis Roca Rothgerber Christie LLP

(57) ABSTRACT

A triazine-based compound is represented by Formula 1 and an organic light-emitting device includes the triazine-based compound.

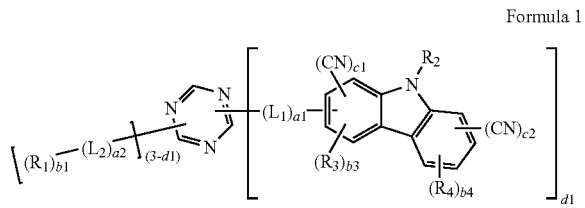

Formula 1

20 Claims, 1 Drawing Sheet

(51) Int. Cl.
 C07D 403/04 (2006.01)
 C09K 11/06 (2006.01)
(52) U.S. Cl.
 CPC ...... H01L 51/0072 (2013.01); H01L 51/0052 (2013.01); H01L 51/5072 (2013.01); H01L 2251/308 (2013.01)

(56) References Cited

U.S. PATENT DOCUMENTS

| | | |
|---|---|---|
| 2004/0137270 A1 | 7/2004 | Seo et al. |
| 2010/0039026 A1 | 2/2010 | Yang et al. |
| 2011/0121274 A1 | 5/2011 | Parham et al. |
| 2012/0126692 A1 | 5/2012 | Ise et al. |
| 2012/0223276 A1 | 9/2012 | Parham et al. |
| 2012/0267620 A1* | 10/2012 | Min ............... C09K 11/06 257/40 |
| 2013/0306959 A1 | 11/2013 | Ikeda et al. |
| 2015/0041773 A1 | 2/2015 | Park et al. |
| 2015/0060787 A1 | 3/2015 | Park et al. |
| 2015/0069342 A1 | 3/2015 | Lee et al. |
| 2015/0069347 A1 | 3/2015 | Kim et al. |
| 2015/0069355 A1 | 3/2015 | Hwang et al. |

FOREIGN PATENT DOCUMENTS

| | | |
|---|---|---|
| JP | 4060669 B2 | 3/2008 |
| JP | 2009-021336 A | 1/2009 |
| JP | 2010-195708 A | 9/2010 |
| JP | 2011-49512 A | 3/2011 |
| KR | 10-0525408 | 11/2005 |
| KR | 10-0958641 | 5/2010 |
| KR | 10-2011-0075690 | 7/2011 |
| KR | 10-2012-0104246 | 9/2012 |
| KR | 10-2015-0018229 | 2/2015 |
| KR | 10-2015-0025259 | 3/2015 |
| KR | 10-2015-0027897 | 3/2015 |
| KR | 10-2015-0028860 | 3/2015 |
| KR | 10-2015-0028935 | 3/2015 |
| WO | WO 2010/015306 A1 | 2/2012 |
| WO | WO 2012/086170 A1 | 6/2012 |

OTHER PUBLICATIONS

Tang, C.W. et al., *Organic electroluminescent diodes*, Applied Physics Letters, 51 (12), Sep. 21, 1987, American Institute of Physics, 913-915.

Tao, Y.T., et al., *Sharp green electroluminescence from 1H-pyrazolo[3,4-b]quinoline-based light-emitting diodes*, Applied Physics Letters, vol. 77, No. 11, Sep. 11, 2000, pp. 1575-1577.

Johansson, Nicklas et al., *Solid-State Amplified Spontaneous Emission in Some Spiro-Type Molecules: A New Concept for the Design of Solid-State Lasing Molecules*, Advanced Materials, 1998, 10, No. 14, pp. 1136-1141.

Yamaguchi, Shigehiro, *Diphenylamino-Substituted 2,5-Diarylsiloles for Single-Layer Organic Electroluminescent Devices*, Chemistry Letters 2001, The Chemical Society of Japan, pp. 98-99.

Sakamoto, Youichi et al., *Synthesis, Characterization, and Electron-Transport Property of Perfluorinated Phenylene Dendrimers*, J. Am. Chem. Soc. vol. 122, No. 8, 2000, pp. 1832-1833, 2 pages.

* cited by examiner

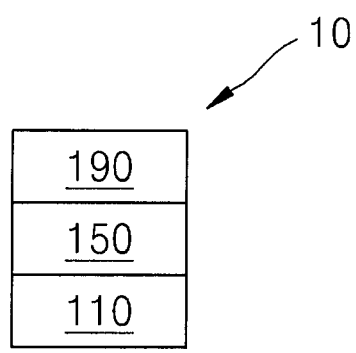

TRIAZINE-BASED COMPOUNDS AND ORGANIC LIGHT-EMITTING DEVICES INCLUDING TRIAZINE-BASED COMPOUNDS

CROSS-REFERENCE TO RELATED APPLICATION

This application claim priority to and the benefit of Korean Patent Application No. 10-2013-0155641, filed on Dec. 13, 2013, in the Korean Intellectual Property Office, the disclosure of which is incorporated herein in its entirety by reference.

BACKGROUND

1. Field

One or more embodiments of the present invention relate to triazine-based compounds and organic light-emitting devices including the triazine-based compounds.

2. Description of the Related Art

Organic light-emitting devices (OLEDs) are self-emitting devices that have enhancements such as wide viewing angles, excellent contrast, or quick response time; excellent characteristics such as brightness, driving voltage, or response speed; and can provide multicolored images.

An OLED has a structure including a first electrode, a hole transport region, an emission layer (EML), an electron transport region, and a second electrode, which are sequentially stacked on a substrate.

Holes injected from the first electrode move to the EML via the hole transport region, and electrons injected from the second electrode move to the EML via the electron transport region. Carriers such as holes and electrons recombine in the EML to generate excitons. When the excitons drop from an excited state to a ground state, light is emitted.

SUMMARY

Aspects according to one or more embodiments of the present invention are directed toward triazine-based compounds and organic light-emitting devices including the triazine-based compounds.

Additional aspects will be set forth in part in the description which follows and, in part, will be apparent from the description, or may be learned by practice of the presented embodiments.

According to one or more embodiments of the present invention, a triazine-based compound is represented by Formula 1:

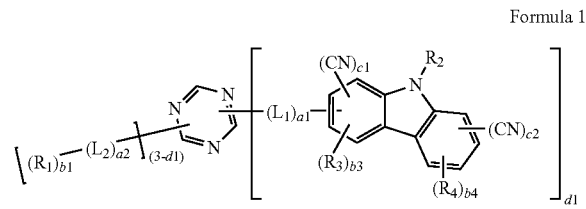

Formula 1 in Formula 1, $L_1$ and $L_2$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ hetero-cycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group and a substituted or unsubstituted divalent non-aromatic hetero-condensed polycyclic group, except for a substituted or unsubstituted anthracenylene group, and a substituted or unsubstituted pyrenylene group;

a1 and a2 may be each independently selected from integers of 0 to 6;

$R_1$ may be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group and a substituted or unsubstituted monovalent non-aromatic hetero-condensed polycyclic group, except for a substituted or unsubstituted carbazolyl group;

$R_2$ may be selected from a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic hetero-condensed polycyclic group;

$R_3$ and $R_4$ may be each independently selected from a hydrogen, a deuterium, —F, —Cl, —Br, —I, a cyano group, a nitro group, a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic hetero-condensed polycyclic group;

at least one substituent for each of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_6$-$C_{60}$ aryl group, substituted $C_1$-$C_{60}$ heteroaryl group, substituted monovalent non-aromatic condensed polycyclic group, and substituted monovalent non-aromatic hetero-condensed polycyclic group may be selected from:

a deuterium, —F, —Cl, —Br, —I, a hydroxyl group, a cyano group, a nitro group, an amino group, an amidino group, a hydrazine, a hydrazone, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, $C_2$-$C_{60}$ alkynyl group, $C_1$-$C_{60}$ alkoxy group, and —Si($Q_1$)($Q_2$)($Q_3$);

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine, a hydrazone, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic hetero-condensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic hetero-condensed polycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic hetero-condensed polycyclic group, each substituted with at least one selected from a deuterium, a halogen atom, a hydroxyl group, a cyano group, a nitro group, an amino group, an amidino group, a hydrazine, a hydrazone, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, non-aromatic condensed polycyclic group, and a non-aromatic hetero-condensed polycyclic group;

$Q_1$ to $Q_3$ may be each independently selected from, a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic hetero-condensed polycyclic group;

b1 and b3 may be each independently selected from integers of 1 to 3;

b4 may be selected from integers of 1 to 4;

c1 and c2 may be each independently selected from integers of 0 to 3; a sum of c1 and c2 is an integer of 1 or greater; and d1 is an integer of 1 to 3.

According to one or more embodiments of the present invention, an organic light-emitting device includes a first electrode; a second electrode facing the first electrode; and an organic layer between the first electrode and the second electrode, the organic layer including an emission layer, and at least one triazine-based compound described above.

BRIEF DESCRIPTION OF THE DRAWINGS

These and/or other aspects will become apparent and more readily appreciated from the following description of the embodiments, taken in conjunction with the accompanying drawings in which:

The drawing is a schematic view of a structure of an organic light-emitting device according to an embodiment.

DETAILED DESCRIPTION

Reference will now be made in more detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the FIGURES, to explain aspects of the present description. As used herein, terms such as "hydroxyl", "$C_6$-$C_{60}$ aryl", etc. each refers to a functional group, such as a hydroxyl group, a $C_6$-$C_{60}$ aryl group, etc. Expressions such as "at least one of," when preceding a list of elements, modify the entire list of elements and do not modify the individual elements of the list. Further, the use of "may" when describing embodiments of the present invention refers to "one or more embodiments of the present invention."

A triazine-based compound is represented by Formula 1 below:

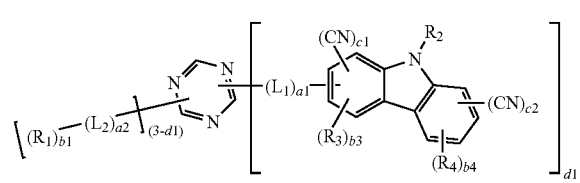

Formula 1 in Formula 1, $L_1$ and $L_2$ may be each independently selected from a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic hetero-condensed polycyclic group, except for a substituted or unsubstituted anthracenylene and a substituted or unsubstituted pyrenylene;

at least one substituent for each of the substituted $C_3$-$C_{10}$ cycloalkylene, substituted $C_1$-$C_{10}$ heterocycloalkylene, substituted $C_3$-$C_{10}$ cycloalkenylene, substituted $C_1$-$C_{10}$ heterocycloalkenylene, substituted $C_6$-$C_{60}$ arylene, substituted $C_1$-$C_{60}$ heteroarylene, a substituted divalent non-aromatic condensed polycyclic group, and a substituted divalent non-aromatic hetero-condensed polycyclic group may be selected from:

a deuterium, —F, —Cl, —Br, —I, a hydroxyl, a cyano, a nitro, an amino, an amidino, a hydrazine, a hydrazone, a carboxyl group and a salt thereof, a sulfonic acid and a salt thereof, a phosphoric acid and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, and —Si($Q_1$)($Q_2$)($Q_3$);

a $C_1$-$C_{60}$ alkyl, a $C_2$-$C_{60}$ alkenyl, a $C_2$-$C_{60}$ alkynyl, and a $C_1$-$C_{60}$ alkoxy, each substituted with at least one selected $C_1$-$C_{60}$ from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group;

a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group; and a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group; and $Q_1$ to $Q_3$ may be each independently selected from a $C_1$-$C_{60}$ alkyl, a $C_6$-$C_{60}$ aryl, a $C_1$-$C_{60}$ heteroaryl, a monovalent non-aromatic condensed polycyclic group, and a monovalent non-aromatic hetero-condensed polycyclic group.

In an embodiment, in Formula 1, $L_1$ and $L_2$ may be each independently selected from:

a phenylene, a pentalenylene, an indenylene, a naphthylene, an azulenylene, a heptalenylene, an indacenylene, an acenaphthylene, a fluorenylene, a spiro-fluorenylene, a benzofluorenylene, a dibenzofluorenylene, a phenalenylene, a phenanthrenylene, a fluoranthenylene, a triphenylenylene, a chrysenylene, a naphthacenylene, a picenylene, a perylenylene, a pentaphenylene, a hexacenylene, a pentacenylene, a rubicenylene, a coronenylene, an ovalenylene, a pyrrolylene, a thienylene, a furanylene, a silolylene, an imidazolylene, a pyrazolylene, a thiazolylene, an isothiazolylene, an oxazolylene, an isooxazolylene, a pyridinylene, a pyrazinylene, a pyrimidinylene, a pyridazinylene, an isoindolylene, an indolylene, an indazolylene, a purinylene, a quinolinylene, an isoquinolinylene, a benzoquinolinylene, a phthalazinylene, a naphthyridinylene, a quinoxalinylene, a quinazolinylene, a cinnolinylene, a carbazolylene, a phenanthridinylene, an acridinylene, a phenanthrolinylene, a phenazinylene, a benzimidazolylene, a benzofuranylene, a benzothienylene, a benzosilolylene, an isobenzothiazolylene, a benzooxazolylene, an isobenzooxazolylene, a triazolylene, a tetrazolylene, an oxadiazolylene, a triazinylene, a dibenzofuranylene, a dibenzothiophenylene, a benzocarbazolyene, a dibenzocarbazolyene, and a dibenzosilolylene; and a phenylene, a pentalenylene, an indenylene, a naphthylene, an azulenylene, a heptalenylene, an indacenylene, an acenaphthylene, a fluorenylene, a spiro-fluorenylene, a benzofluorenylene, a dibenzofluorenylene, a phenalenylene, a phenanthrenylene, a fluoranthenylene, a triphenylenylene, a chrysenylene, a naphthacenylene, a picenylene, a perylenylene, a pentaphenylene, a hexacenylene, a pentacenylene, a rubicenylene, a coronenylene, an ovalenylene, a pyrrolylene, a thienylene, a furanylene, a silolylene, an imidazolylene, a pyrazolylene, a thiazolylene, an isothiazolylene, an oxazolylene, an isooxazolylene, a pyridinylene, a pyrazinylene, a pyrimidinylene, a pyridazinylene, an isoindolylene, an indolylene, an indazolylene, a purinylene, a quinolinylene, an isoquinolinylene, a benzoquinolinylene, a phthalazinylene, a naphthyridinylene, a quinoxalinylene, a quinazolinylene, a cinnolinylene, a carbazolylene, a phenanthridinylene, an acridinylene, a phenanthrolinylene, a phenazinylene, a benzimidazolylene, a benzofuranylene, a benzothienylene, a benzosilolylene, an isobenzothiazolylene, a benzooxazolylene, an isobenzooxazolylene, a triazolylene, a tetrazolylene, an oxadiazolylene, a triazinylene, a dibenzofuranylene, a dibenzothiophenylene, a benzocarbazolyene, a dibenzocarbazolyene, and a dibenzosilolylene, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, a cyclopentyl, a cyclohexyl, a cycloheptyl, a cyclopentenyl, a cyclohexenyl, a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, a thienyl, a furanyl, a silolyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a carbazolyl, a phenanthridinyl, an acridinyl, a phenanthrolinyl, a phenazinyl, a benzimidazolyl, a benzofuranyl, a benzothienyl, a benzosilolyl, an isobenzothiazolyl, a benzooxazolyl, an isobenzooxazolyl, a triazolyl, a tetrazole, an oxadiazolyl, a triazinyl, a dibenzofuranyl, a dibenzothienyl, a benzocarbazolyl, a dibenzocarbazolyl, and a dibenzosilolyl, but they are not limited thereto.

In another embodiment, in Formula 1, $L_1$ and $L_2$ may be each independently any one of compounds represented by Formulae 3-1 to 3-30, but they are not limited thereto:

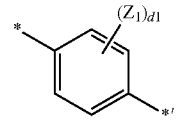

3-1

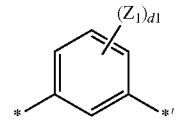

3-2

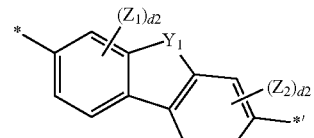

3-3

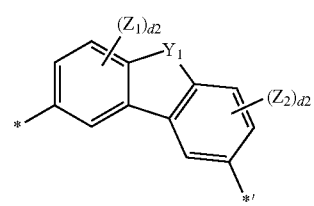

3-4

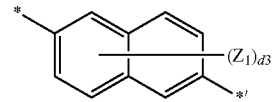

3-5

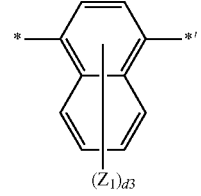

3-6

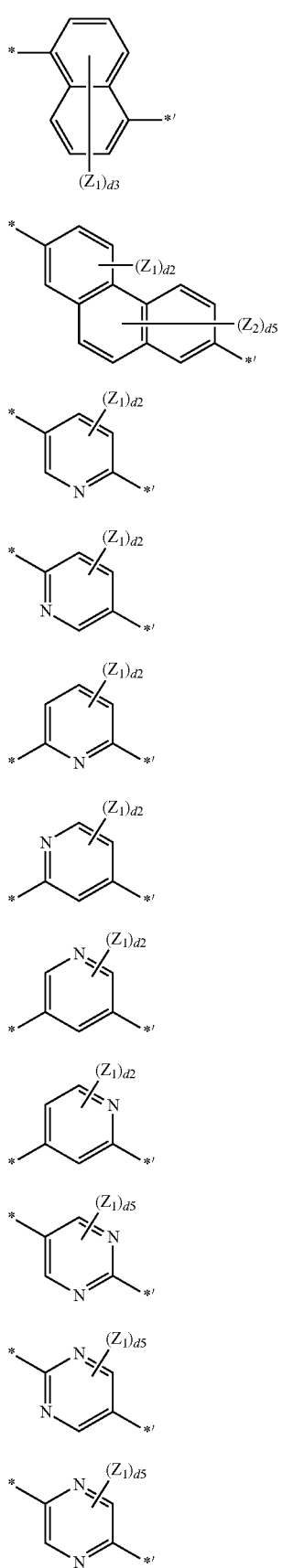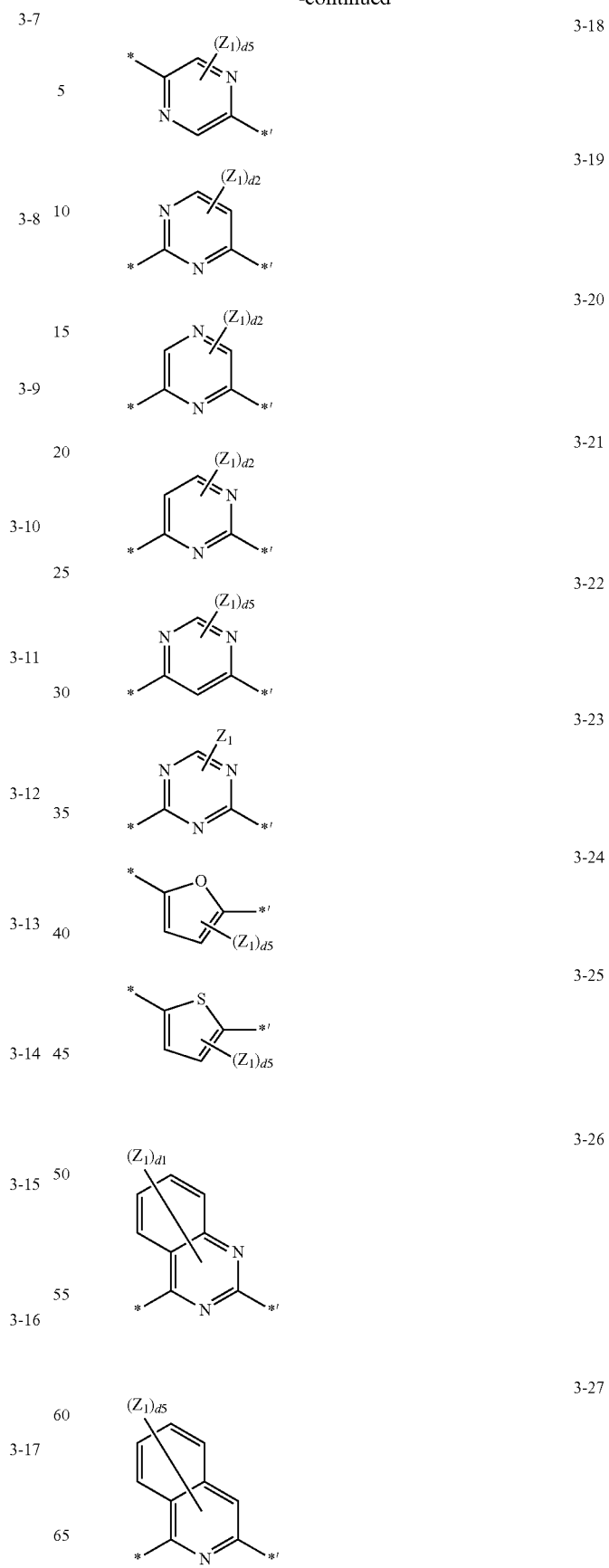

-continued 3-28

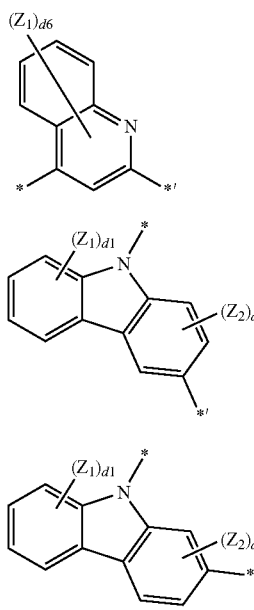

3-29

3-30 in Formulae 3-1 to 3-30, $Y_1$ may be selected from $C(Q_{31})(Q_{32})$, $N(Q_{33})$, an oxygen atom, a sulfur atom, and $Si(Q_{34})(Q_{35})$;

$Q_{31}$ to $Q_{35}$ are each independently selected from a hydrogen, a deuterium, a $C_1$-$C_{20}$ alkyl, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl;

$Z_1$ and $Z_2$ are each independently selected from a hydrogen, a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl, d1 is selected from integers of 1 to 4;
d2 is selected from integers of 1 to 3;
d3 is selected from integers of 1 to 6;
d5 is 1 or 2;
d6 is selected from integers of 1 to 5;
* and *' are each independently bonding sites to different atoms.

In another embodiment, in Formula 1, $L_1$ and $L_2$ may be each independently represented by Formulae 4-1 to 4-21, but they are not limited thereto:

4-1

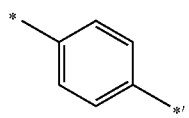

4-2

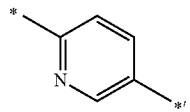

4-3

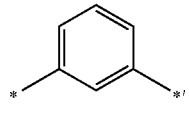

4-4

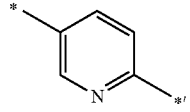

4-5

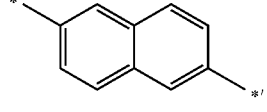

4-6

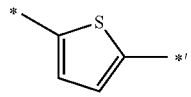

4-7

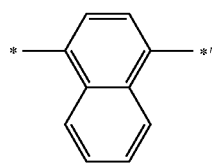

4-8

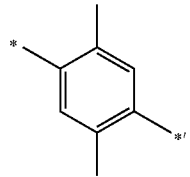

4-9

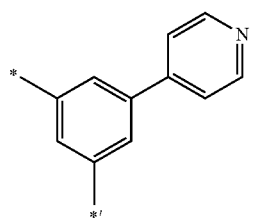

4-10

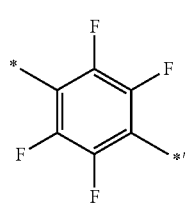

4-11

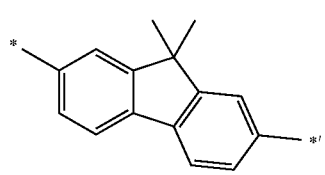

-continued

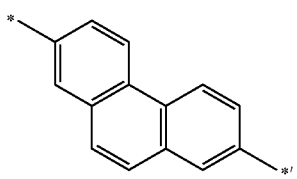
4-12

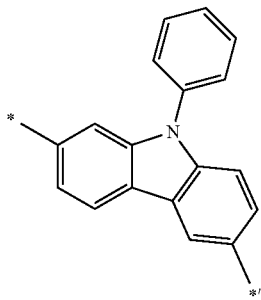
4-13

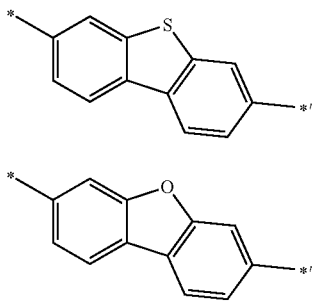
4-14

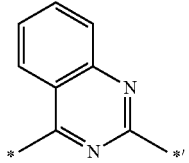
4-15

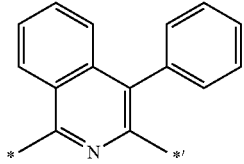
4-16

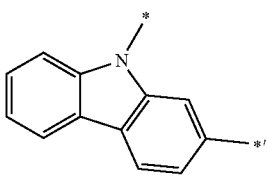
4-17

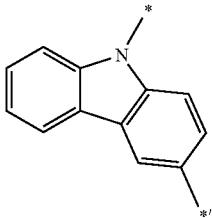
4-18

4-19

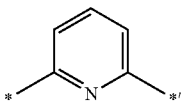
4-20

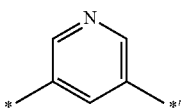
4-21 in Formulae 4-1 to 4-21,
* and *' may be each independently bonding sites to neighboring atoms.

In Formula 1, a1 represents the number of $L_1$s and may be selected from integers of 0 to 6. When a1 is an integer of 2 or greater, a plurality of $L_1$s may be the same or different. When a1 is 0, $(L_1)_{a1}$ represents a single bond.

In an embodiment, in Formula 1, a1 may be selected from integers of 0 to 3, but it is not limited thereto.

In another embodiment, in Formula 1, a1 may be an integer of 0 or 1, but a1 is not limited thereto.

In Formula 1, a2 represents the number of $L_2$s and may be selected from integers of 0 to 6. When a2 is an integer of 2 or greater, a plurality of $L_2$s may be the same or different. When a2 is 0, $(L_2)_{a2}$ represents a single bond.

In an embodiment, in Formula 1, a2 may be an integer selected from 0 to 3, but a2 is not limited thereto.

In another embodiment, in Formula 1, a2 may be an integer of 0 or 1, but a2 is not limited thereto.

In Formula 1, $R_1$ is selected from a substituted or unsubstituted $C_6$-$C_{60}$ aryl, a substituted or unsubstituted $C_1$-$C_{60}$ heteroaryl, a substituted or unsubstituted monovalent non-aromatic condensed polycyclic group, and a substituted or unsubstituted monovalent non-aromatic hetero-condensed polycyclic group, except for a substituted or unsubstituted carbazolyl;

at least one substituent for each of the substituted $C_6$-$C_{60}$ aryl, substituted $C_1$-$C_{60}$ heteroaryl, substituted monovalent non-aromatic condensed polycyclic group, and substituted monovalent non-aromatic hetero-condensed polycyclic group may be selected from:

a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, $C_1$-$C_{60}$ alkyl, $C_2$-$C_{60}$ alkenyl, $C_2$-$C_{60}$ alkynyl, alkoxy, and —Si($Q_1$)($Q_2$)($Q_3$);

a $C_1$-$C_{60}$ alkyl, a $C_2$-$C_{60}$ alkenyl, a $C_2$-$C_{60}$ alkynyl, and a $C_1$-$C_{60}$ alkoxy, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid and a salt thereof, a phosphoric acid and a salt thereof, $C_3$-$C_{10}$ cycloalkyl, $C_3$-$C_{10}$ heterocycloalkyl, $C_3$-$C_{10}$ cycloalkenyl, $C_3$-$C_{10}$ heterocycloalkenyl, $C_6$-$C_{60}$ aryl, $C_6$-$C_{60}$ aryloxy, $C_6$-$C_{60}$ arylthio, $C_1$-$C_{60}$ heteroaryl, a non-aromatic condensed polycyclic group, and a non-aromatic hetero-condensed polycyclic group;

a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group; and a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group;

$Q_1$ to $Q_3$ may be each independently selected from a $C_1$-$C_{60}$ alkyl, a $C_6$-$C_{60}$ aryl, a $C_1$-$C_{60}$ heteroaryl, a monovalent non-aromatic condensed polycyclic group, and a monovalent non-aromatic hetero-condensed polycyclic group.

In an embodiment, in Formula 1, $R_1$ may be a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, a thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a dibenzofuranyl, a dibenzothiophenyl, a benzocarbazolyl, and a dibenzocarbazolyl; and a phenyl, a pentalenyl, an indenyl, a naphthyl, an azulenyl, a heptalenyl, an indacenyl, an acenaphthyl, a fluorenyl, a spires-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, a thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a benzofuranyl, dibenzothiophenyl, a benzocarbazolyl, and a dibenzocarbazolyl, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, —Si($Q_1$)($Q_2$)($Q_3$), a halogen atom substituted $C_1$-$C_{20}$ alkyl, a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a carbazolyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a dibenzofuranyl, dibenzothiophenyl, a benzocarbazolyl, and a dibenzocarbazolyl; and $Q_1$ to $Q_3$ may be each independently selected from a $C_1$-$C_{20}$ alkyl, a phenyl, a naphthyl, and a pyridinyl, but they are not limited thereto.

In another embodiment, in Formula 1, $R_1$ may be selected from a phenyl, a naphthyl, a fluorenyl, a phenanthrenyl, an anthracenyl, a triphenylenyl, a pyrenyl, a chrysenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, a quinolinyl, an isoquinolinyl, phenanthridinyl, an acridinyl, a phenanthrolinyl, a benzimidazolyl, a benzofuranyl, benzothiophenyl, a benzooxazolyl, a triazolyl, a tetrazolyl, a triazinyl, a dibenzofuranyl, and a dibenzothiophenyl; and a phenyl, a naphthyl, a fluorenyl, a phenanthrenyl, an anthracenyl, a triphenylenyl, a pyrenyl, a chrysenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, a quinolinyl, an isoquinolinyl, phenanthridinyl, an acridinyl, a phenanthrolinyl, a benzimidazolyl, a benzofuranyl, benzothiophenyl, a benzooxazolyl, a triazolyl, a tetrazolyl, a triazinyl, a dibenzofuranyl, and a dibenzothiophenyl, each substituted with at least one selected from a deuterium, —F, —Cl, —Br, —I, a cyano, a nitro, a methyl, an ethyl, an n-propyl, a tert-butyl, a methoxy, an ethoxy, a tert-butoxy, —Si($CH_3$)$_3$, —Si(Ph)$_3$, —$CF_3$, a phenyl, a naphthyl, a fluorenyl, a phenanthrenyl, an anthracenyl, a triphenylenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a quinolinyl, an isoquinolinyl, a naphthyridinyl, a quinoxalinyl, a quinazolinyl, a carbazolyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a dibenzofuranyl, and a dibenzothiophenyl, but it is not limited thereto.

In another embodiment, in Formula 1, $R_1$ may be selected from a phenyl, a naphthyl, a fluorenyl, a phenanthrenyl, pyridinyl, a pyrazinyl, a pyrimidinyl, a quinolinyl, an isoquinolinyl, and a triazinyl;

a phenyl, a naphthyl, a fluorenyl, a phenanthrenyl, a pyridinyl, a pyrazinyl, a pyrimidinyl, a quinolinyl, an isoquinolinyl and a triazinyl, each substituted with at least one selected from a deuterium, —F, —Cl, —Br, —I, a cyano, a nitro, methyl, methoxy, —Si($CH_3$)$_3$, —Si(Ph)$_3$, —$CF_3$, a phenyl, a naphthyl, a fluorenyl, a carbazolyl, a pyridinyl, a pyrazinyl, a pyrimidinyl, a quinolinyl, an isoquinolinyl, and a triazinyl.

In another embodiment, in Formula 1, $R_1$ may be any one group selected from Formulae 5-1 to 5-34, but it is not limited thereto:
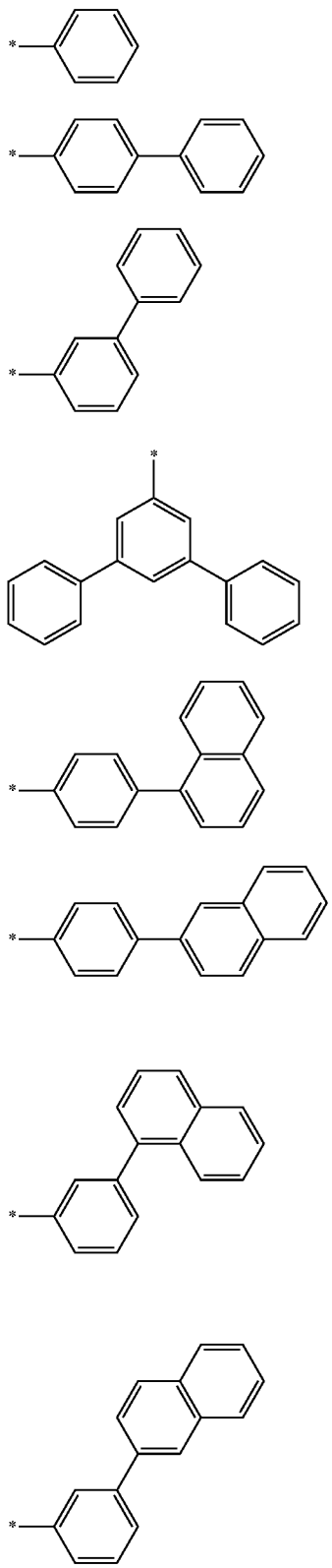
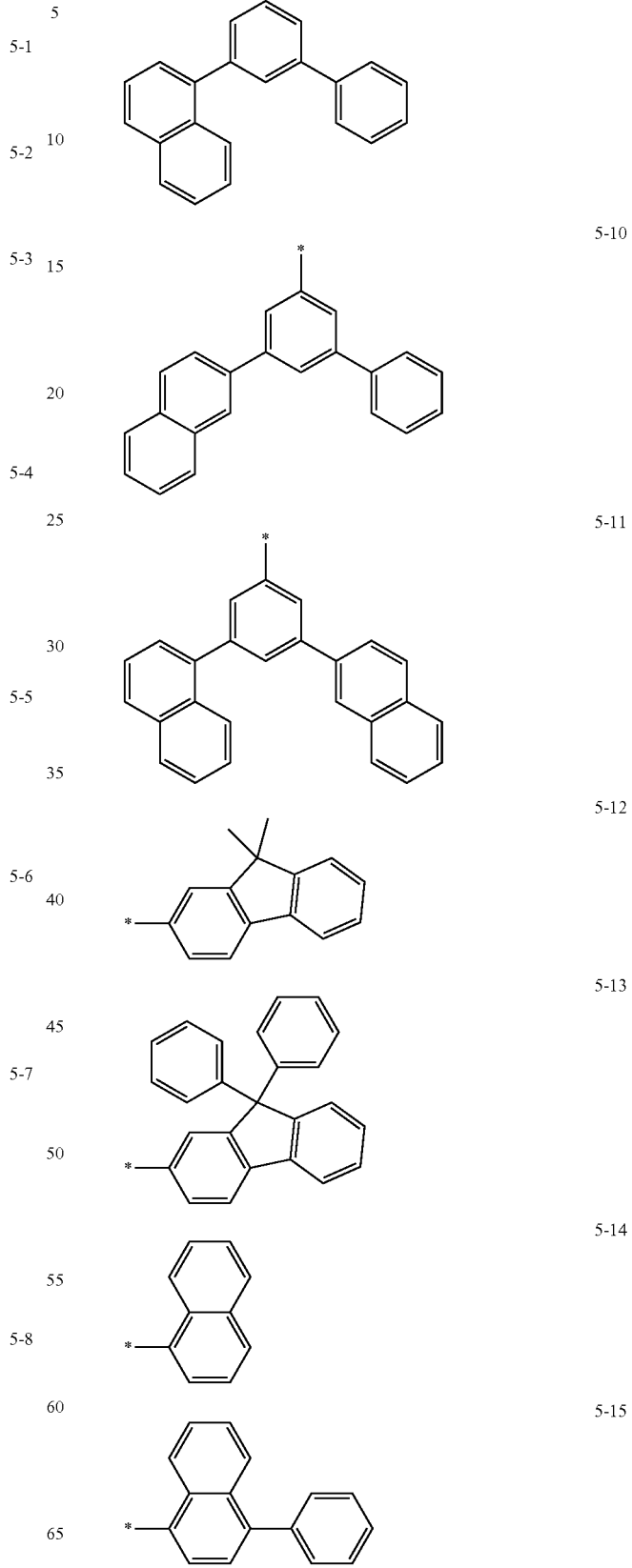

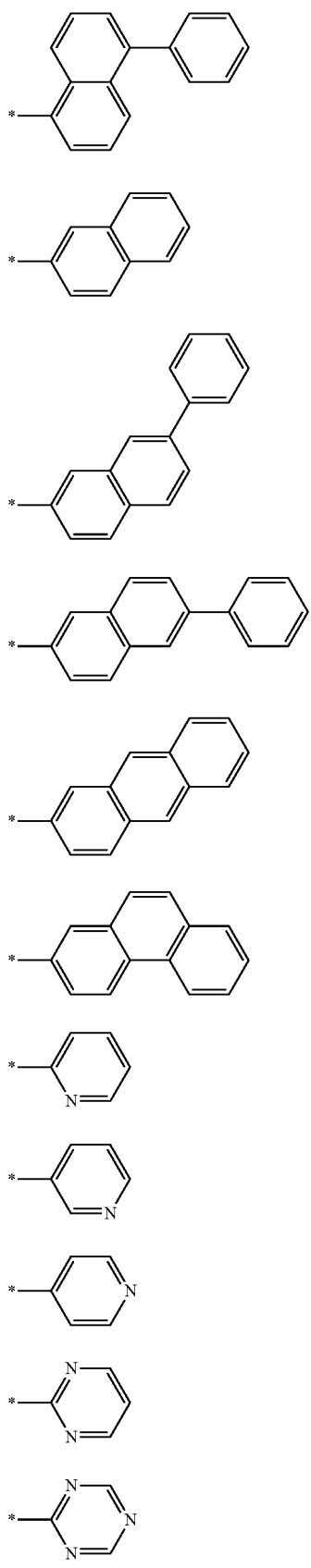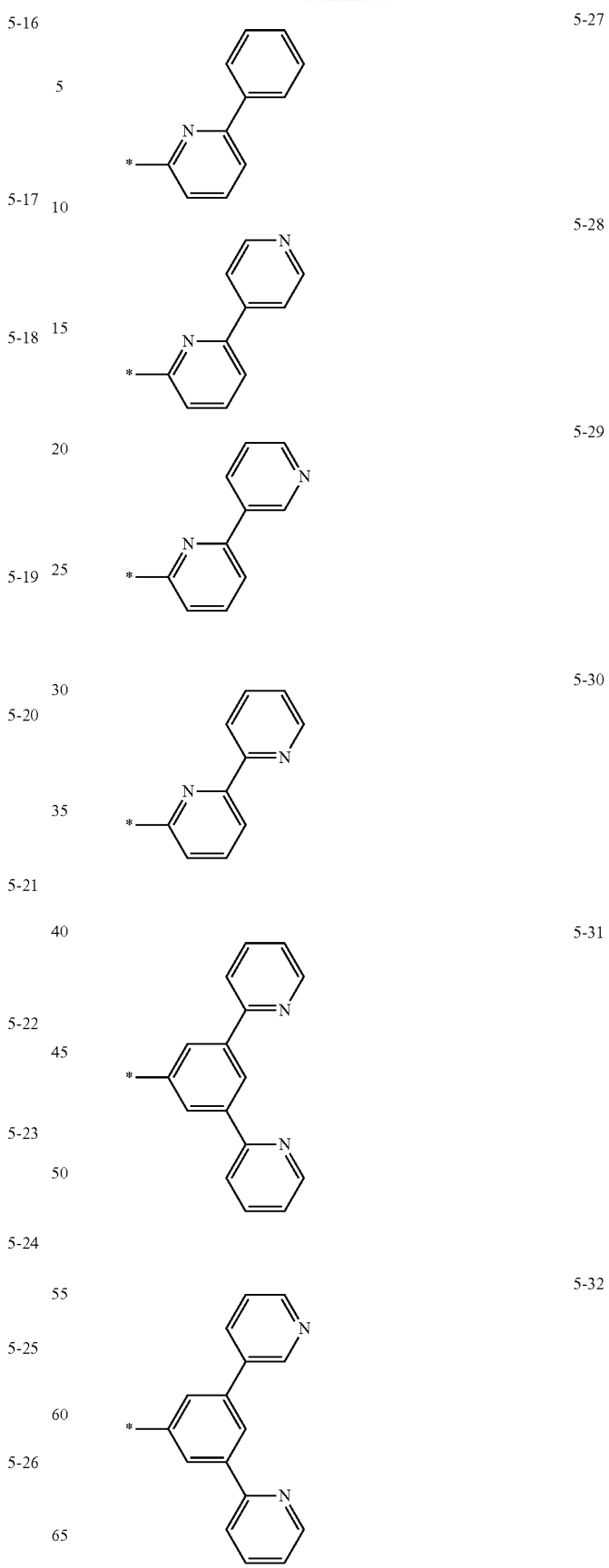

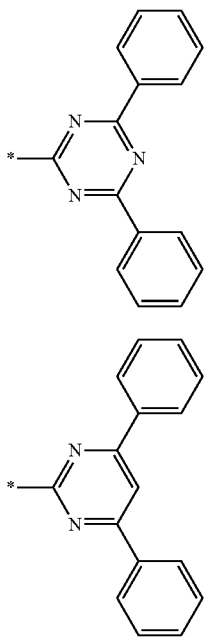

5-33

5-34 in Formulae 5-1 to 5-34,
* is a bonding site to a neighboring atom.

In Formula 1, $R_2$ is selected from a substituted or unsubstituted $C_1$-$C_{60}$ alkyl, a substituted or unsubstituted $C_6$-$C_{60}$ aryl, a substituted or unsubstituted $C_1$-$C_{60}$ heteroaryl, a substituted or unsubstituted monovalent non-aromatic condensed polycyclic group, and a substituted or unsubstituted monovalent non-aromatic hetero-condensed polycyclic group;

at least one substituent for each of the substituted $C_1$-$C_{60}$ alkyl, substituted $C_6$-$C_{60}$ aryl, substituted $C_1$-$C_{60}$ heteroaryl, substituted monovalent non-aromatic condensed polycyclic group, and substituted monovalent non-aromatic hetero-condensed polycyclic group may be selected from:

a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy and —Si($Q_1$)($Q_2$)($Q_3$);

a $C_1$-$C_{60}$ alkyl, a $C_2$-$C_{60}$ alkenyl, a $C_2$-$C_{60}$ alkynyl, and a $C_1$-$C_{60}$ alkoxy, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group;

a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group; and a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group;

$Q_1$ to $Q_3$ may be each independently selected from a $C_1$-$C_{60}$ alkyl, a $C_6$-$C_{60}$ aryl, a $C_1$-$C_{60}$ heteroaryl, a monovalent non-aromatic condensed polycyclic group, and a monovalent non-aromatic hetero-condensed polycyclic group.

In an embodiment, in Formula 1, $R_2$ may be selected from a methyl, an ethyl, an n-propyl, an iso-propyl, an n-butyl, an iso-butyl, a tert-butyl, an n-pentyl, an n-hexyl, an n-heptyl, an n-octyl, a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a carbazolyl, a dibenzofuranyl, a dibenzothiophenyl, a benzocarbazolyl, and a dibenzocarbazolyl; and a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a carbazolyl, a dibenzofuranyl, dibenzothiophenyl, a benzocarbazolyl, and a dibenzocarbazolyl, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, —Si($Q_1$)($Q_2$)($Q_3$), a halogen atom substituted $C_1$-$C_{20}$ alkyl, a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a carbazolyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a dibenzofuranyl, dibenzothiophenyl, a benzocarbazolyl, and a dibenzocarbazolyl; and $Q_1$ to $Q_3$ may be each independently selected from a $C_1$-$C_{20}$ alkyl, a phenyl, a naphthyl, and a pyridinyl, but they are not limited thereto.

In another embodiment, in Formula 1, $R_2$ may be selected from a methyl, an ethyl, an n-propyl, an iso-propyl, an n-butyl, an iso-butyl, a tert-butyl, a phenyl, a naphthyl, a fluorenyl, a phenanthrenyl, an anthracenyl, a triphenylenyl, a pyrenyl, a chrysenyl, a pyrrolyl, a thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, a quinolinyl, an isoquinolinyl, a phenanthridinyl, an acridinyl, a phenanthrolinyl, a benzimidazolyl, a benzofuranyl, benzothiophenyl, a benzooxazolyl, a triazolyl, a tetrazolyl, a triazinyl, a carbazolyl, a dibenzofuranyl, and a dibenzothiophenyl; and a phenyl, a naphthyl, a fluorenyl, a phenanthrenyl, an anthracenyl, a triphenylenyl, a pyrenyl, a chrysenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, a quinolinyl, an isoquinolinyl, a phenanthridinyl, an acridinyl, a phenanthrolinyl, a benzimidazolyl, a benzofuranyl, benzothiophenyl, a benzooxazolyl, a triazolyl, a tetrazolyl, a triazinyl, a carbazolyl, a dibenzofuranyl, and a dibenzothiophenyl, each substituted with at least one selected from a deuterium, —F, —Cl, —Br, —I, a cyano, a nitro, a methyl, an ethyl, an n-propyl, a tert-butyl, a methoxy, an ethoxy, a tert-butoxy, —Si(CH$_3$)$_3$, —Si(Ph)$_3$, —CF$_3$, a phenyl, a naphthyl, a fluorenyl, a phenanthrenyl, an anthracenyl, a triphenylenyl, a pyrrolyl, a thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a quinolinyl, an isoquinolinyl, a naphthyridinyl, a quinoxalinyl, a quinazolinyl, a carbazolyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a dibenzofuranyl, and a dibenzothiophenyl, but it is not limited thereto.

In another embodiment, in Formula 1, $R_2$ may be selected from a methyl, an ethyl, an n-propyl, an iso-propyl, an n-butyl, a phenyl, a naphthyl, a fluorenyl, a phenanthrenyl, a pyridinyl, a pyrazinyl, a pyrimidinyl, a quinolinyl, an isoquinolinyl, a triazinyl, a phenanthrolinyl, a dibenzofuranyl, and a dibenzothiophenyl; and a phenyl, a naphthyl, a fluorenyl, a phenanthrenyl, a pyridinyl, a pyrazinyl, a pyrimidinyl, a quinolinyl, an isoquinolinyl, a triazinyl, a phenanthrolinyl, a dibenzofuranyl, and a dibenzothiophenyl, each substituted with at least one selected from a deuterium, —F, —Cl, —Br, —I, a cyano, a nitro, a methyl, a methoxy, —Si(CH$_3$)$_3$, —Si(Ph)$_3$, —CF$_3$, a phenyl, a naphthyl, a fluorenyl, a carbazolyl, a pyridinyl, a pyrazinyl, a pyrimidinyl, a quinolinyl, an isoquinolinyl and a triazinyl, but it is not limited thereto.

In another embodiment, in Formula 1, $R_2$ may be a group selected from a methyl, an ethyl, and Formulae 5-1 to 5-38, but it is not limited thereto:

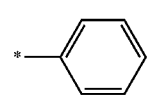

5-1

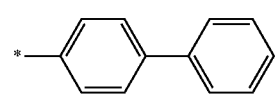

5-2

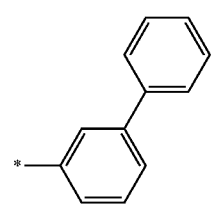

5-3

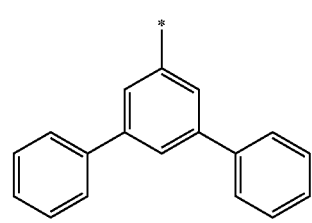

5-4

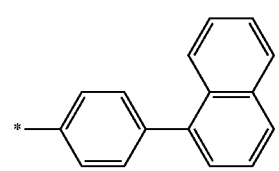

5-5

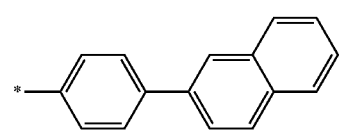

5-6

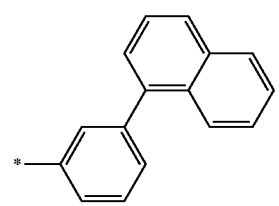

5-7

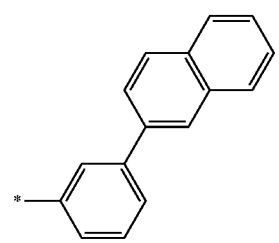

5-8

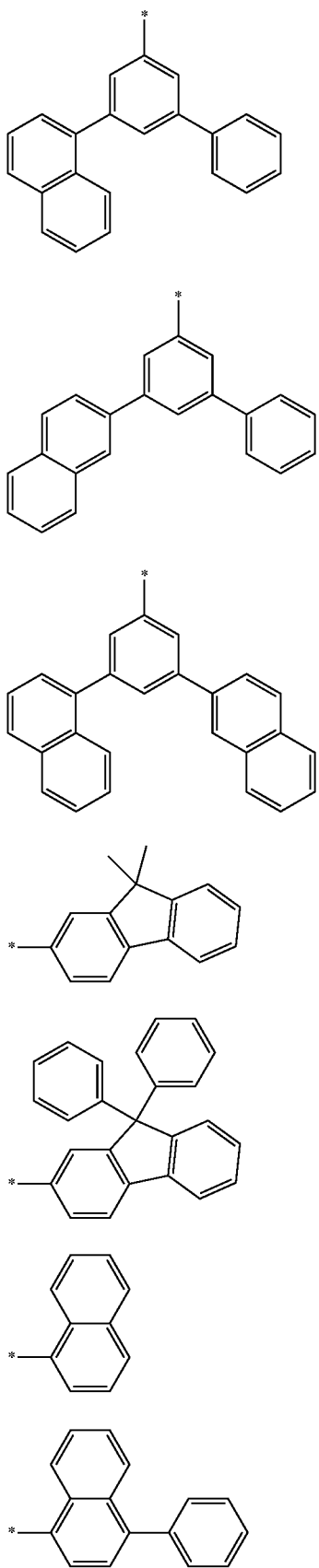
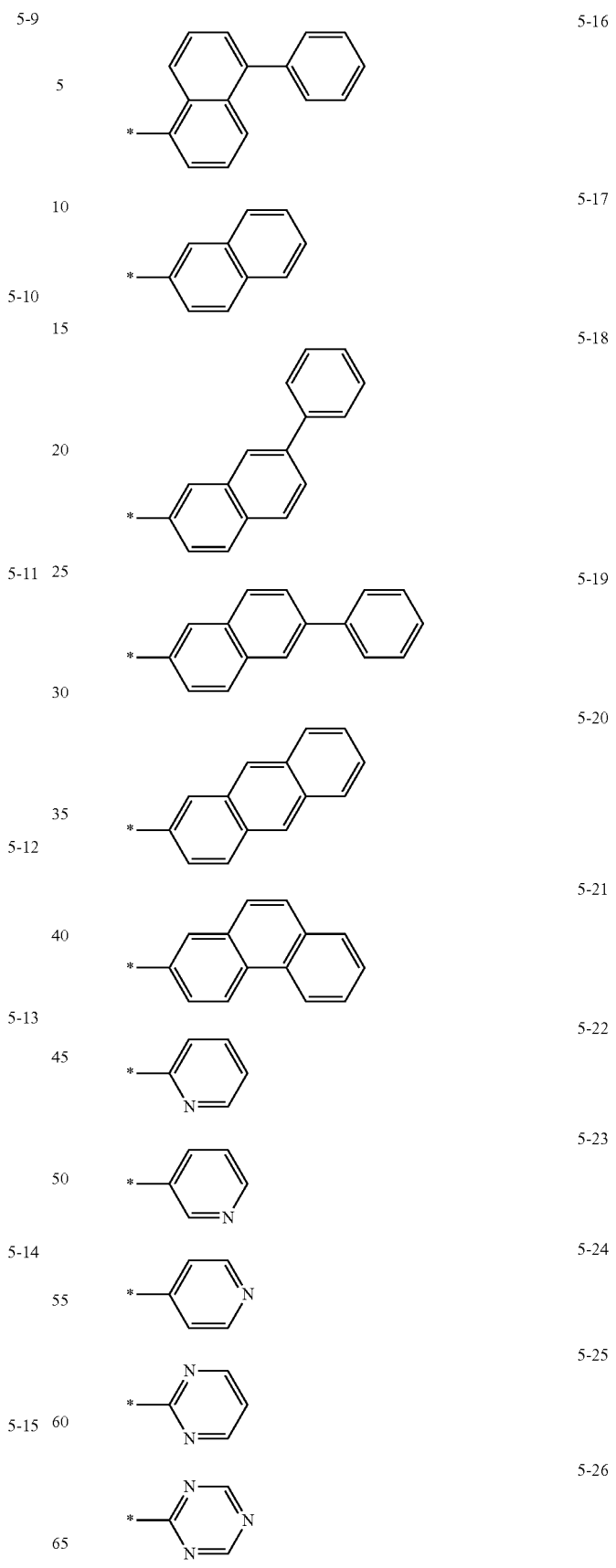

5-27 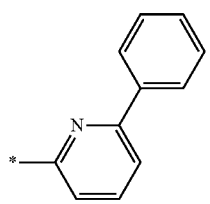

5-28 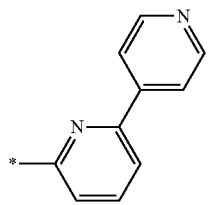

5-29 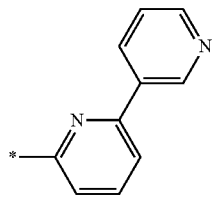

5-30 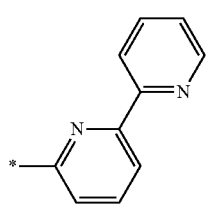

5-31 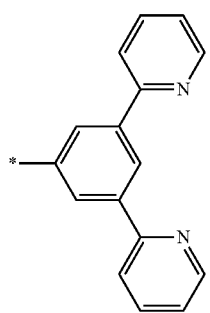

5-32 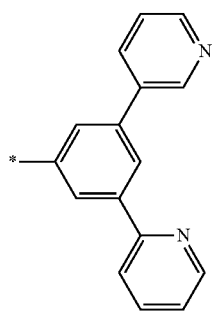

5-33 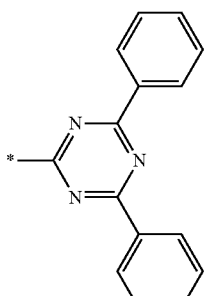

5-34 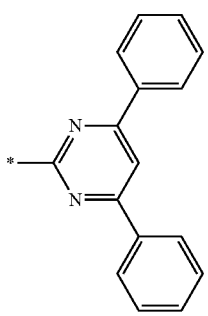

5-35 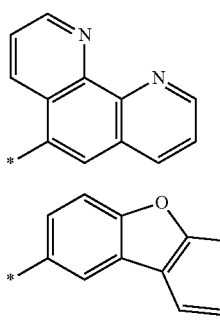

5-36 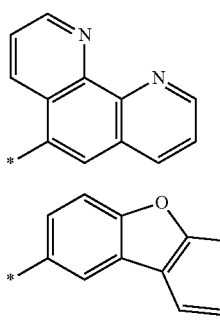

5-37 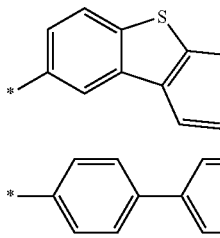

5-38 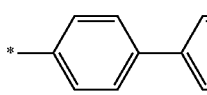

in Formulae 5-1 to 5-38,

* is a bonding site to a neighboring atom.

In Formula 1, $R_3$ and $R_4$ are each independently selected from a hydrogen, a deuterium, —F, —Cl, —Br, —I, a cyano, a nitro, a substituted or unsubstituted $C_1$-$C_{60}$ alkyl, a substituted or unsubstituted $C_6$-$C_{60}$ aryl, a substituted or unsubstituted $C_1$-$C_{60}$ heteroaryl, a substituted or unsubstituted monovalent non-aromatic condensed polycyclic group, and a substituted or unsubstituted monovalent non-aromatic hetero-condensed polycyclic group;

at least one substituent for each of the substituted $C_1$-$C_{60}$ alkyl, substituted $C_6$-$C_{60}$ aryl, substituted $C_1$-$C_{60}$ heteroaryl, substituted monovalent non-aromatic condensed polycyclic group and substituted monovalent non-aromatic hetero-condensed polycyclic group may be selected from:

a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, and —Si($Q_1$)($Q_2$)($Q_3$);

a $C_1$-$C_{60}$ alkyl, a $C_2$-$C_{60}$ alkenyl, a $C_2$-$C_{60}$ alkynyl, and a $C_1$-$C_{60}$ alkoxy, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group;

a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group; and a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_1$-$C_{10}$ heterocycloalkyl, a $C_3$-$C_{10}$ cycloalkenyl, a $C_1$-$C_{10}$ heterocycloalkenyl, a $C_6$-$C_{60}$ aryl, a $C_6$-$C_{60}$ aryloxy, a $C_6$-$C_{60}$ arylthio, a $C_1$-$C_{60}$ heteroaryl, a non-aromatic condensed polycyclic group, and a non-aromatic hetero-condensed polycyclic group; and $Q_1$ to $Q_3$ may be each independently selected from a $C_1$-$C_{60}$ alkyl, a $C_6$-$C_{60}$ aryl, a $C_1$-$C_{60}$ heteroaryl, a monovalent non-aromatic condensed polycyclic group, and a monovalent non-aromatic hetero-condensed polycyclic group.

In an embodiment, in Formula 1, $R_3$ and $R_4$ may be each independently selected from a hydrogen, a deuterium, —F, —Cl, —Br, —I, a cyano, a nitro, and a $C_1$-$C_{20}$ alkyl;

a $C_1$-$C_{20}$ alkyl substituted with at least one selected from a deuterium, —F, —Cl, —Br, —I, a cyano, a nitro, a $C_6$-$C_{60}$ aryl, a $C_1$-$C_{60}$ heteroaryl, a monovalent non-aromatic condensed polycyclic group, and a monovalent non-aromatic hetero-condensed polycyclic group;

a $C_6$-$C_{60}$ aryl, a $C_1$-$C_{60}$ heteroaryl, a monovalent non-aromatic condensed polycyclic group, and a monovalent non-aromatic hetero-condensed polycyclic group; and a $C_6$-$C_{60}$ aryl, a $C_1$-$C_{60}$ heteroaryl, a monovalent non-aromatic condensed polycyclic group, and a monovalent non-aromatic hetero-condensed polycyclic group, each substituted with at least one selected from a deuterium, —F, —Cl, —Br, —I, a cyano, a nitro, a $C_1$-$C_{20}$ alkyl, a $C_6$-$C_{60}$ aryl, a $C_1$-$C_{60}$ heteroaryl, a monovalent non-aromatic condensed polycyclic group, and a monovalent non-aromatic hetero-condensed polycyclic group, but they are not limited thereto.

In another embodiment, in Formula 1, $R_3$ and $R_4$ may be each independently selected from:

a hydrogen, a deuterium, —F, —Cl, —Br, —I, a cyano, a nitro, a methyl, an ethyl, an n-propyl, an iso-propyl, an n-butyl, and a tert-butyl;

a methyl, an ethyl, an n-propyl, an iso-propyl, an n-butyl, and a tert-butyl, each substituted with at least one selected from a deuterium, —F, a cyano, and a nitro;

a phenyl, a naphthyl, a fluorenyl, and a pyridinyl; and a phenyl, a naphthyl, a fluorenyl, and a pyridinyl, each substituted with at least one selected from a deuterium, —F, a cyano, a nitro, methyl, a phenyl, a naphthyl, and a pyridinyl, but they are not limited thereto.

In Formula 1, b1 represents the number of $R_1$s and may be selected from integers of 1 to 3. When $R_1$ is 2 or greater, a plurality of $R_1$s may be the same or different.

In an embodiment, in Formula 1, b1 may be an integer of 1, but it is not limited thereto.

In Formula 1, b3 represents the number of $R_3$s and may be selected from integers of 1 to 3. When b3 is an integer that is 2 or greater, a plurality of $R_3$s may be the same or different.

In Formula 1, b4 represents the number of $R_4$s and may be selected from integers of 1 to 4. When b4 is an integer that is 2 or greater, a plurality of $R_4$s may be the same or different.

In Formula 1, c1 and c2 each represent the number of CNs and may be an integer selected from 0 to 3. However, in Formula 1, a sum of c1 and c2 may be an integer that is 1 or greater.

In an embodiment, in Formula 1, c1 and c2 may be each independently an integer of 0 or 1, and the sum of c1 and c2 may be an integer that is 1 or greater, but they are not limited thereto.

In another embodiment, in Formula 1, c1 is an integer of 0 and c2 is an integer of 1, but they are not limited thereto.

In Formula 1, d1 represents the number of moiety represented by

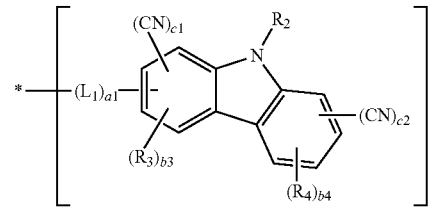

wherein, * is a bonding site to a neighboring atom and d1 may be selected from integers of 1 to 3.

In an embodiment, in Formula 1, d1 may be an integer of 1 or 2, but it is not limited thereto.

For example, the triazine-based compound represented by Formula 1 may be represented by Formula 1A, but the compound is not limited thereto:

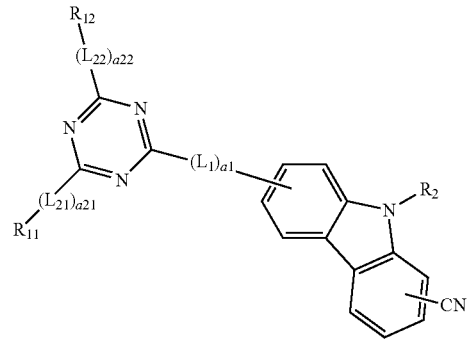

<Formula 1A> in Formula 1A, descriptions of $L_1$, a1, and $R_2$ are as described above;

descriptions of $L_{21}$ and $L_{22}$ are the same as the description of $L_2$;

descriptions of a21 and a22 are the same as the description of a2; and descriptions of $R_{11}$ and $R_{12}$ are the same as the description of $R_1$.

In another embodiment, when the triazine-based compound represented by Formula 1 is represented by Formula 1A, $L_1$, $L_{21}$ and $L_{22}$ in Formula 1A may be each independently represented by any one group selected from Formulae 4-1 to 4-21; a1, a21 and a22 may be each independently an integer of 0 or 1; and $R_{11}$ and $R_{12}$ may be each independently a group selected from Formulae 5-1 to 5-34; and $R_2$ may be any one selected from a methyl, an ethyl, and Formulae 5-1 to 5-34, but they are not limited thereto.

In another embodiment, the triazine-based compound represented by Formula 1 may be represented by any one of Formulae 1B and 1C, but it is not limited thereto:

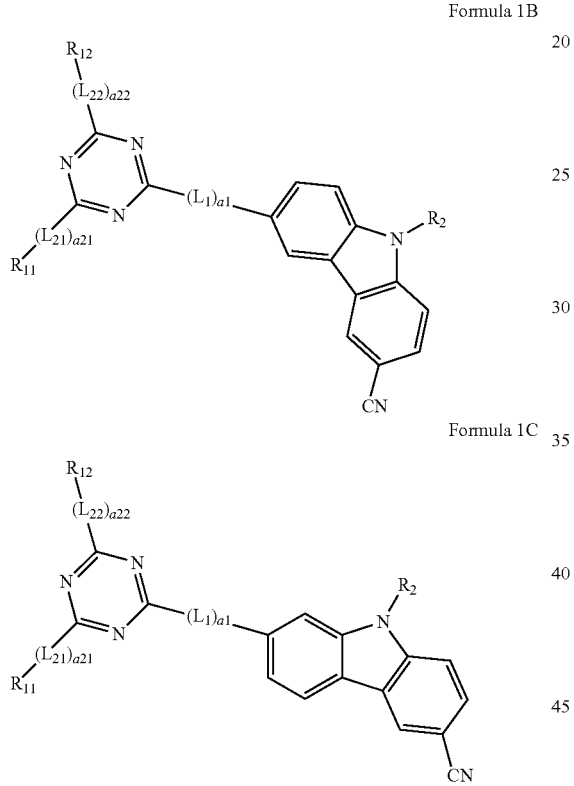

Formula 1B

Formula 1C in Formula 1B and 1C, descriptions of $L_1$, a1, and $R_2$ are as described herein;

descriptions of $L_{21}$ and $L_{22}$ are the same as the description of $L_2$;

descriptions of a21 and a22 are the same as the description of a2; and descriptions of $R_{11}$ and $R_{12}$ are the same as the description of $R_1$.

In another embodiment, when the triazine-based compound represented by Formula 1 is represented by any one of Formulae 1B and 1C, $L_1$, $L_{21}$ and $L_{22}$ of Formulae 1B and 1C may be each independently represented by any one group selected from Formulae 4-1 to 4-21; a1, a21, and a22 may be each independently an integer of 0 or 1; $R_{11}$ and $R_{12}$ may be each independently any one group selected from Formulae 5-1 to 5-34; and $R_2$ may be any one group selected from a methyl, an ethyl, and Formulae 5-1 to 5-34, but they are not limited thereto.

In another embodiment, the triazine-based compound represented by Formula 1 may be selected from Compounds 1 to 95, but the compound is not limited thereto:

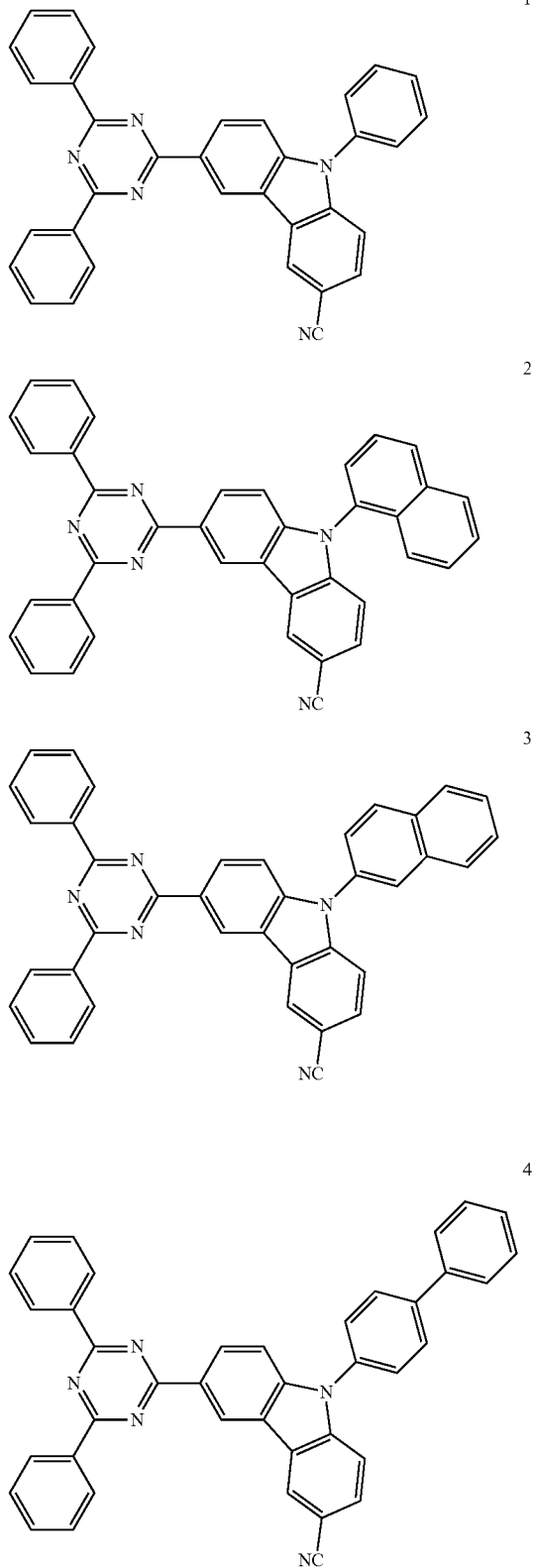

5
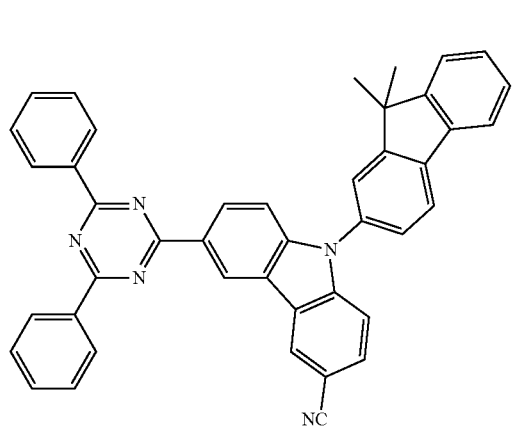
6
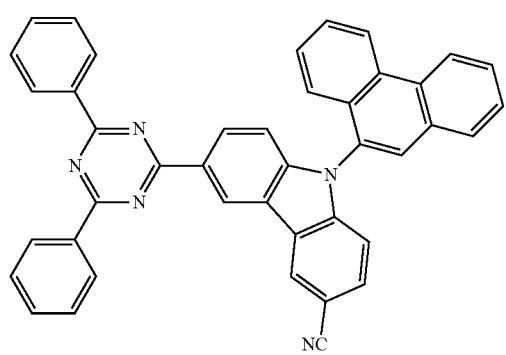
7
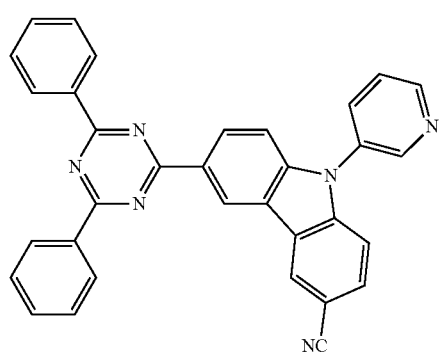
8
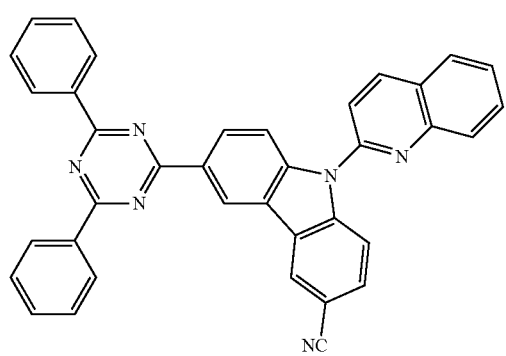
9
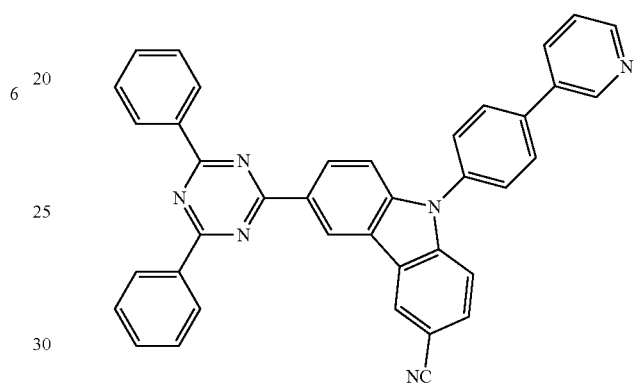
10
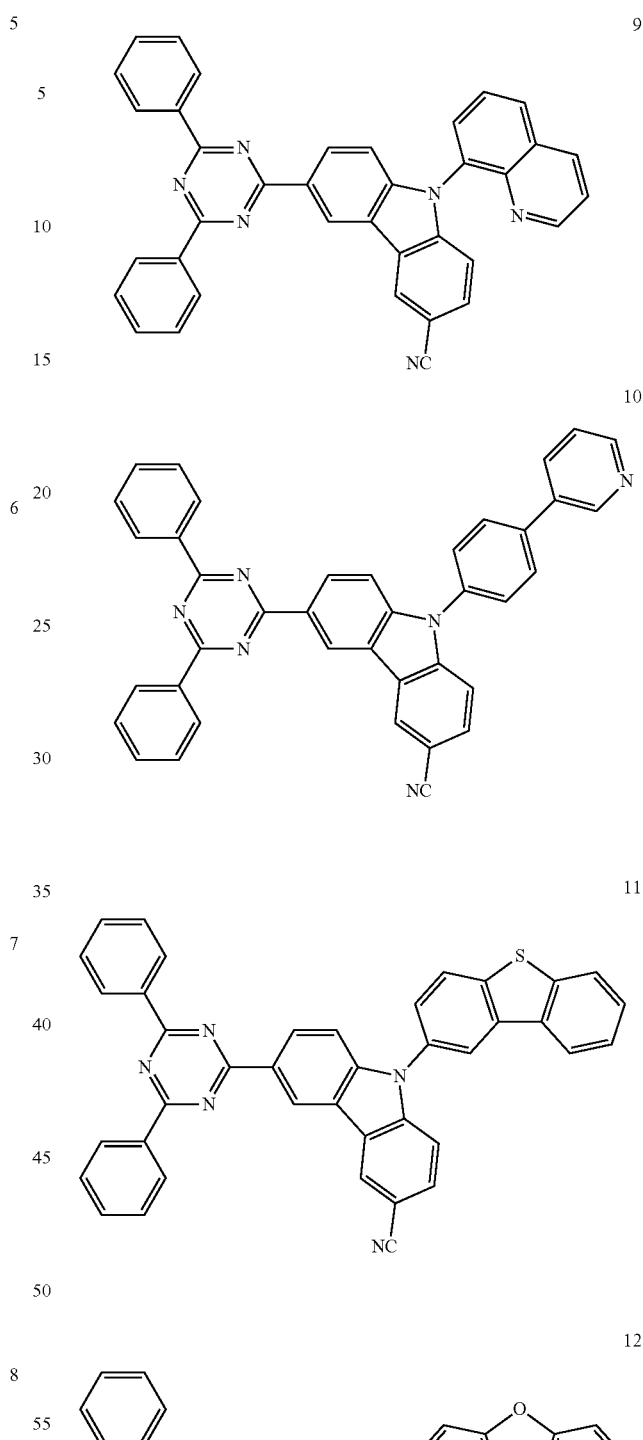
11
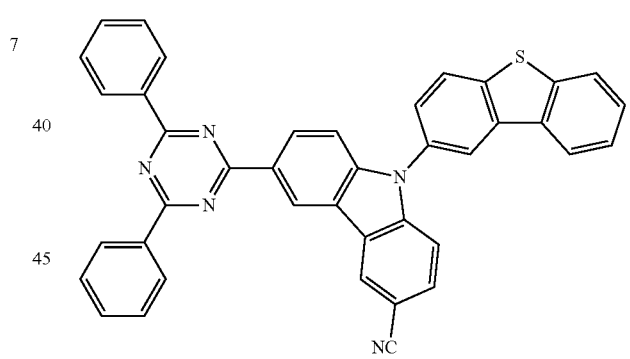
12
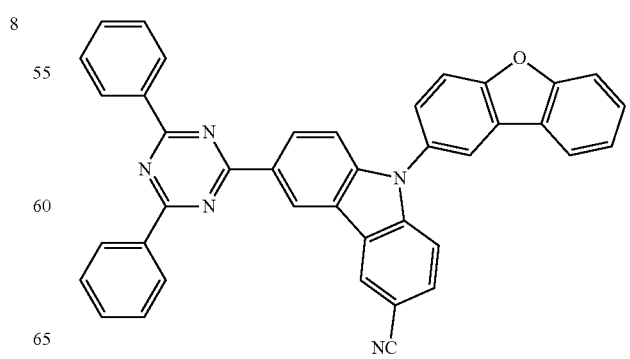

13
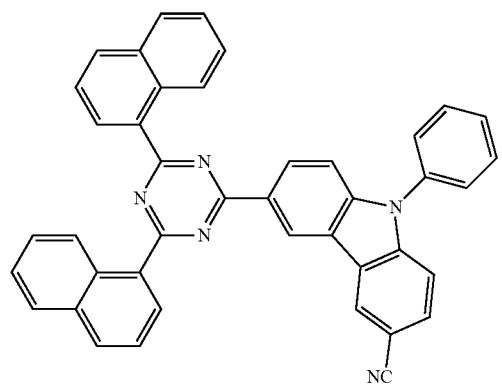
14
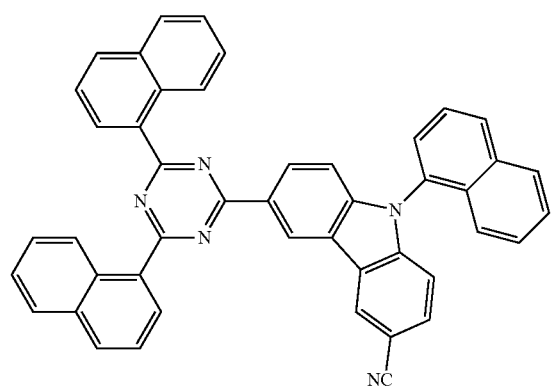
15
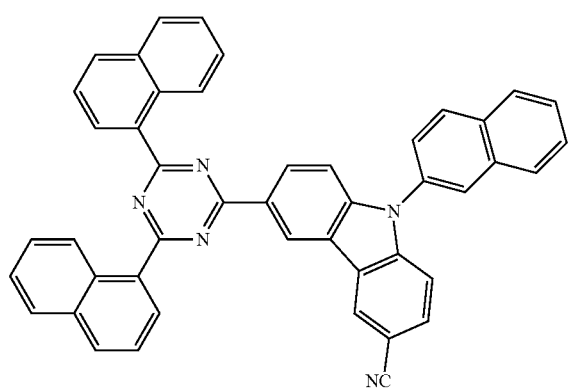
16
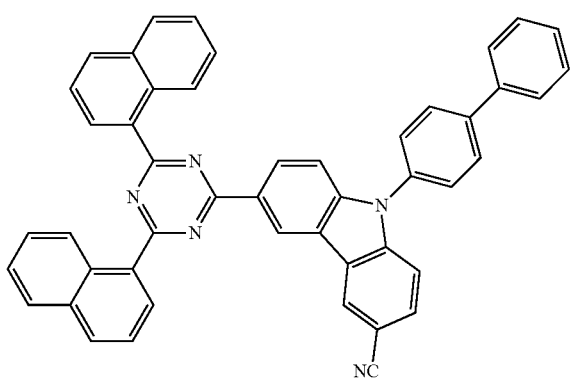
17
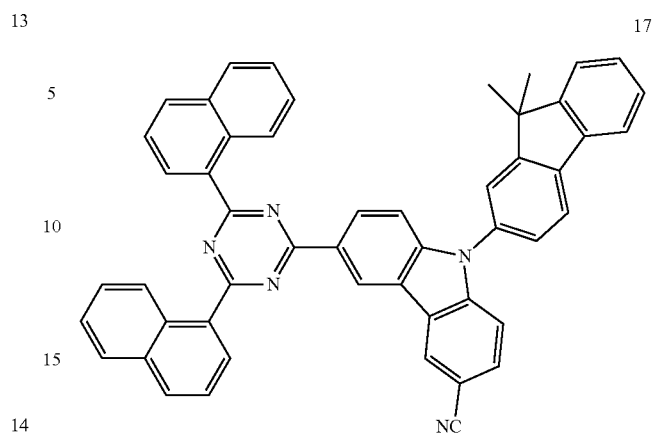
18
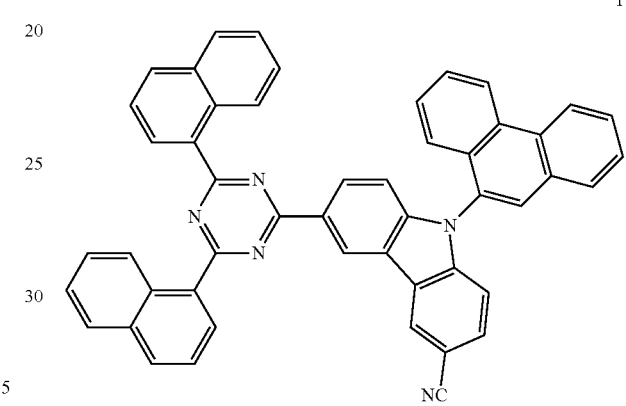
19
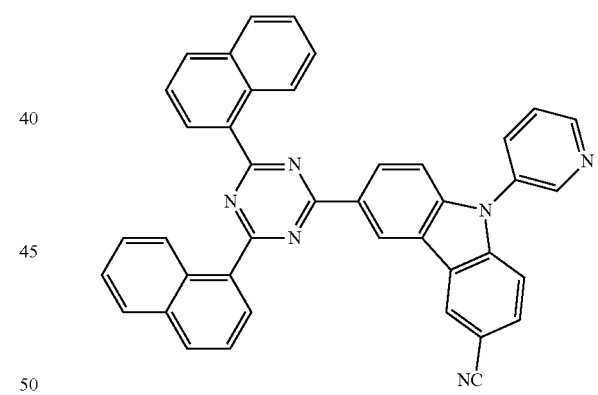
20
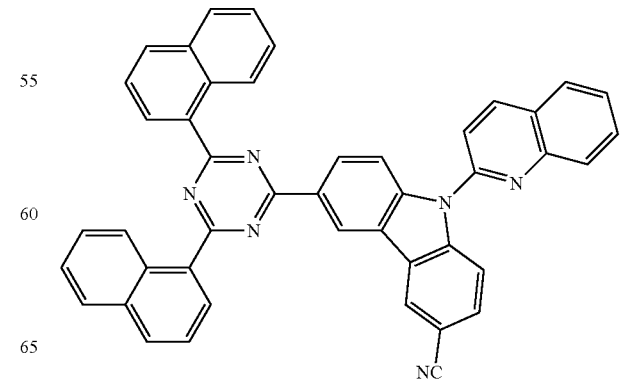

21
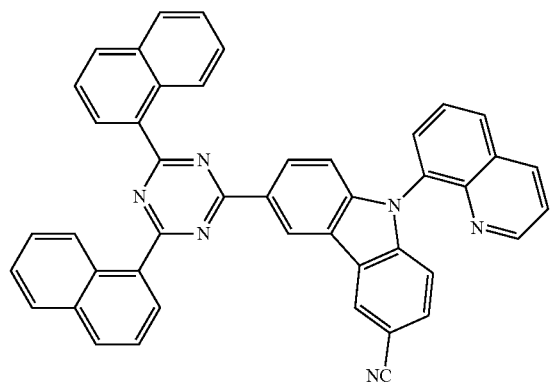
22
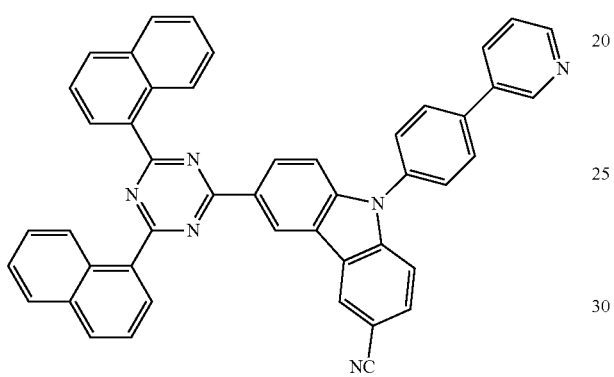
23
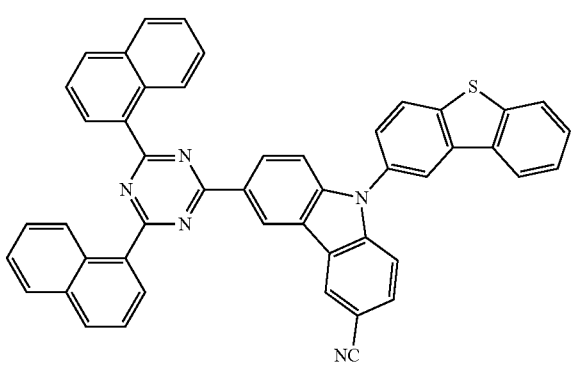
24
25
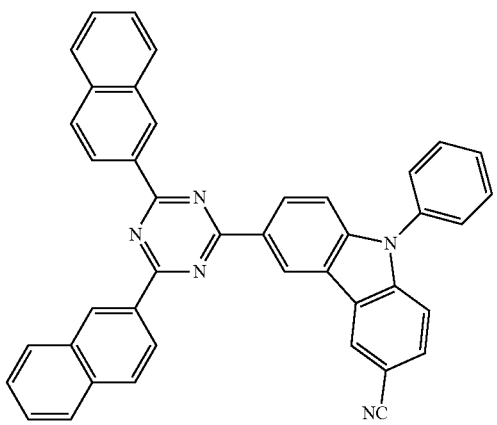
26
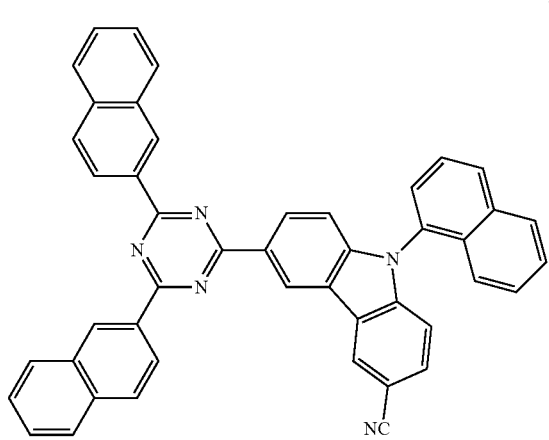
27
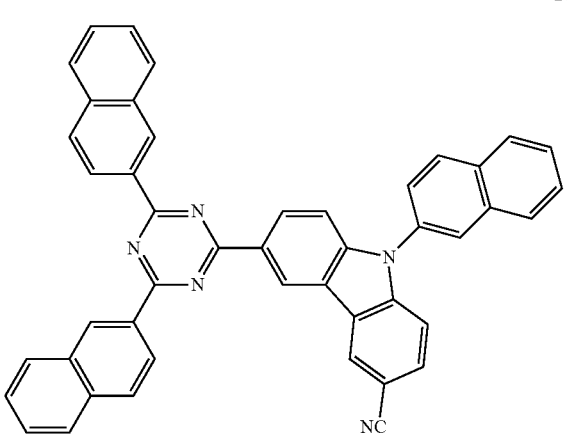

28
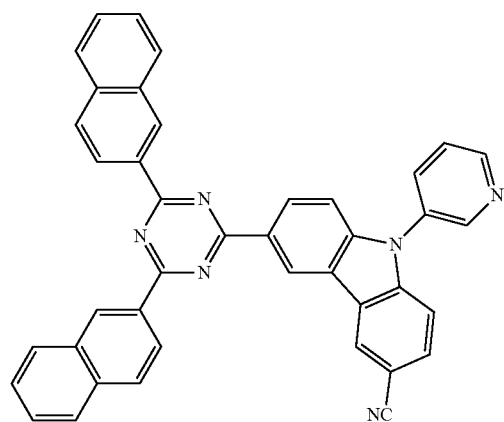
31
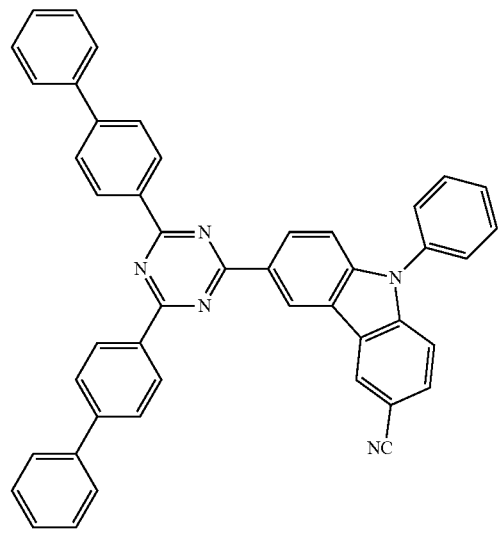
29
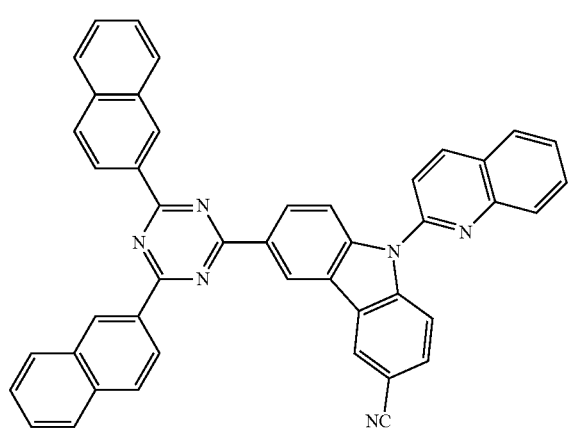
32
30
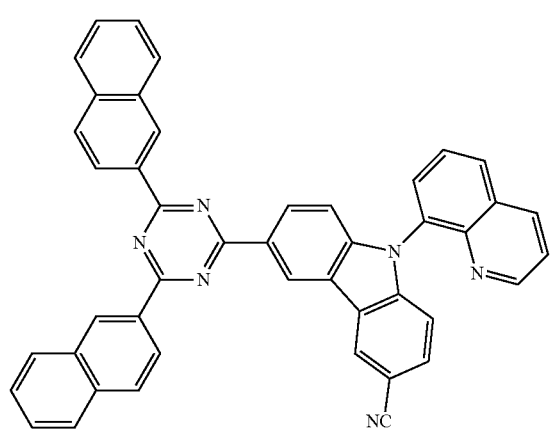
33
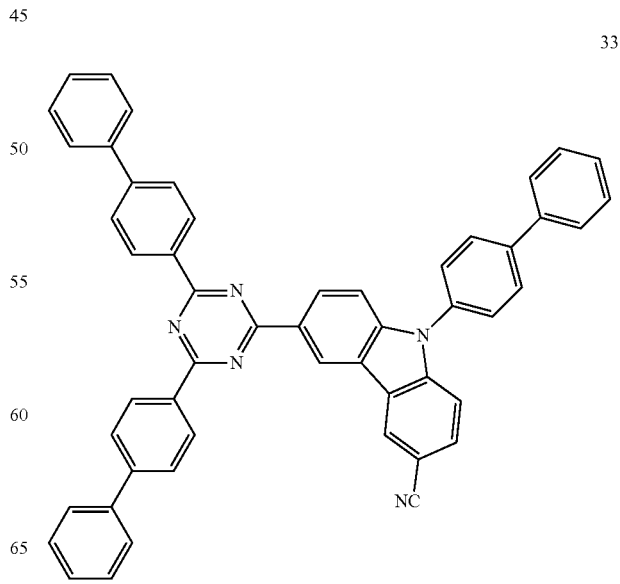

34
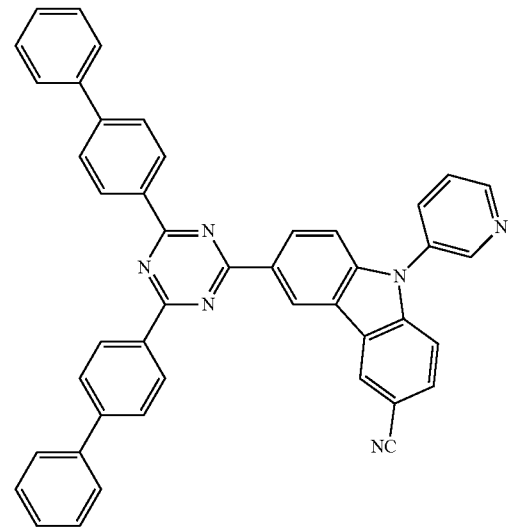
35
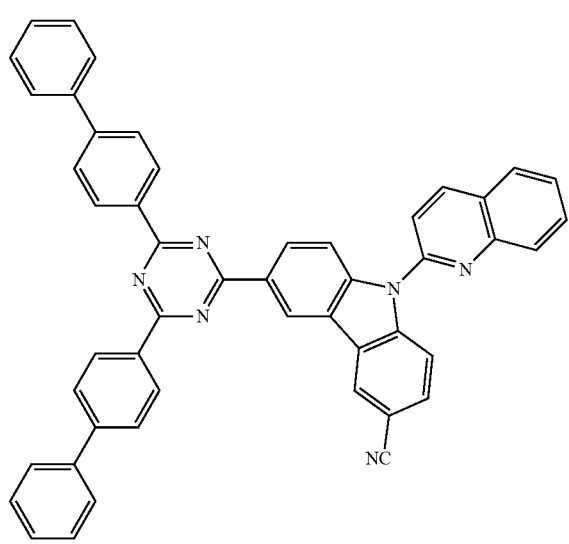
36
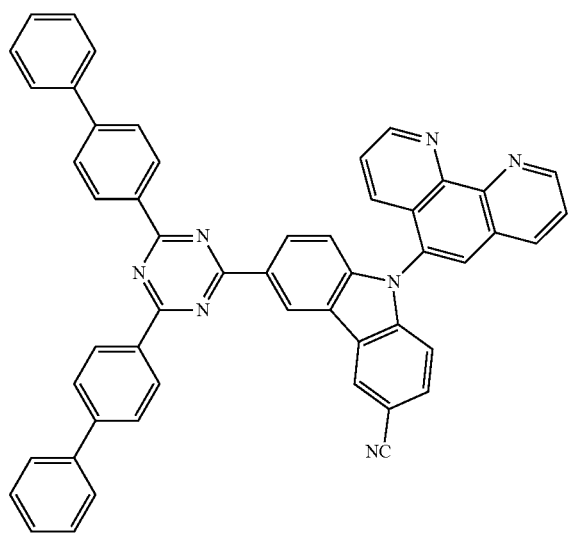
37
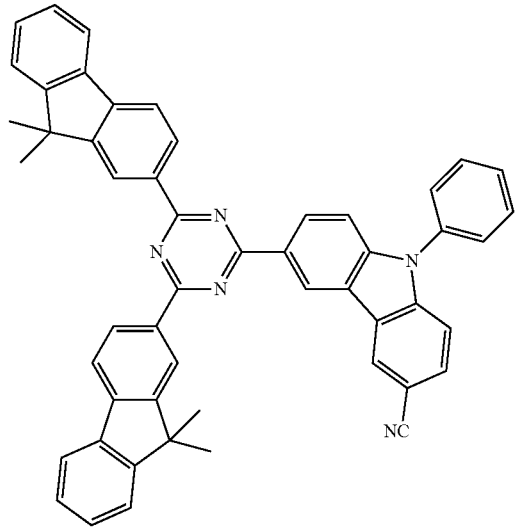
38
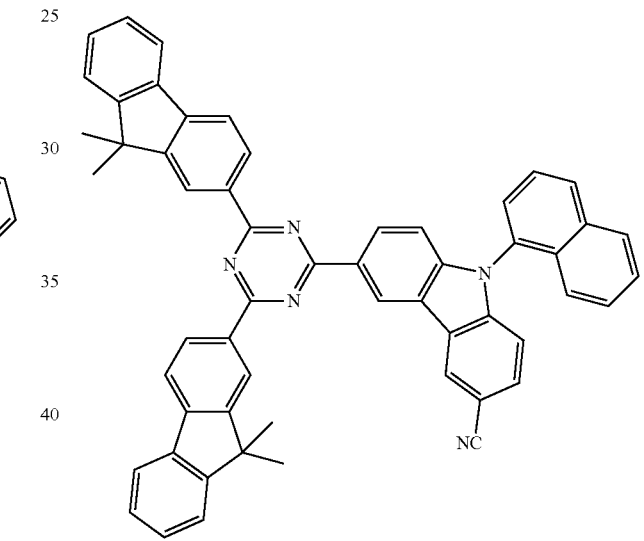
39
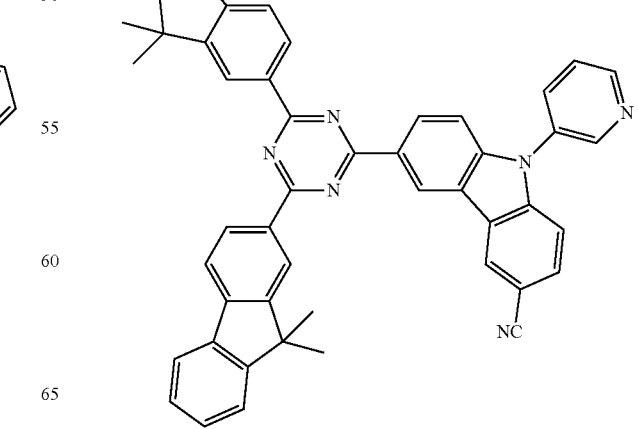

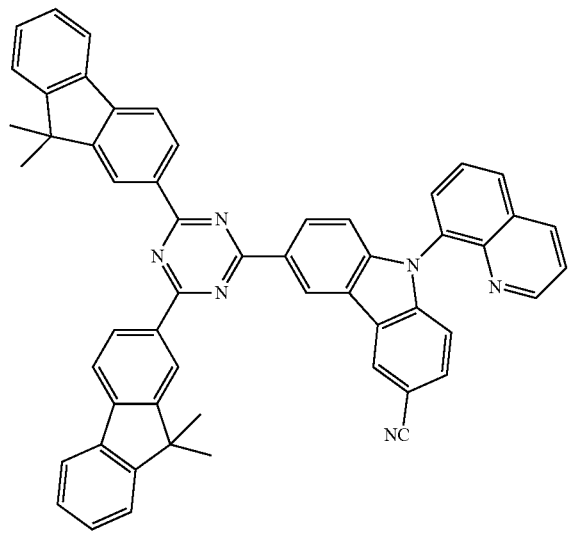
40
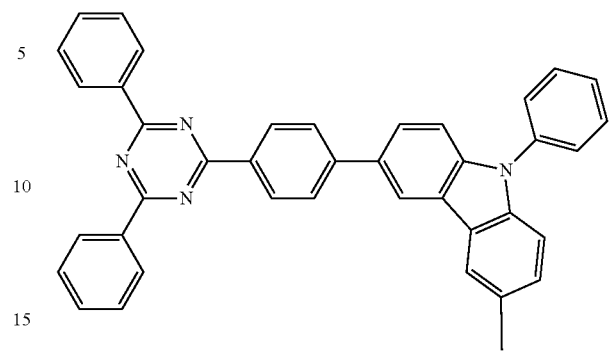
43
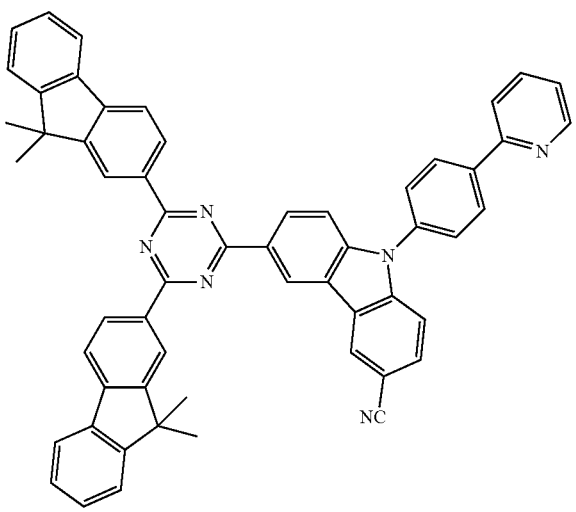
41
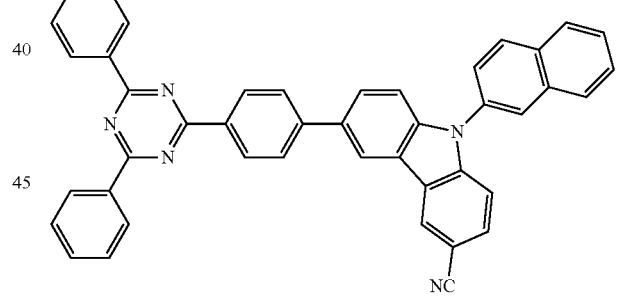
44
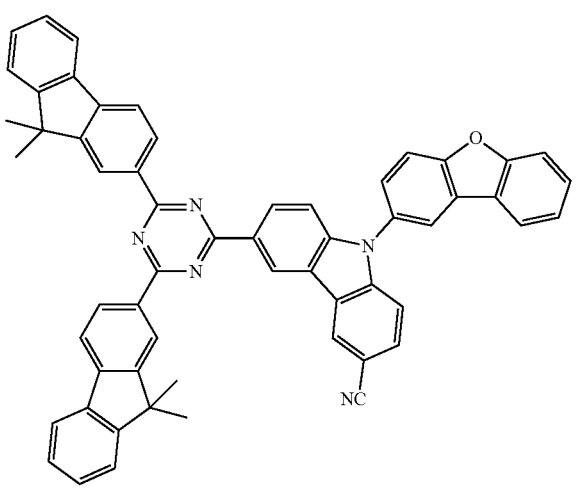
42
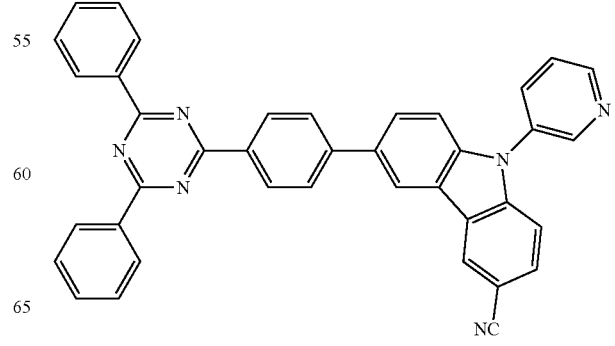
45
46

-continued
47
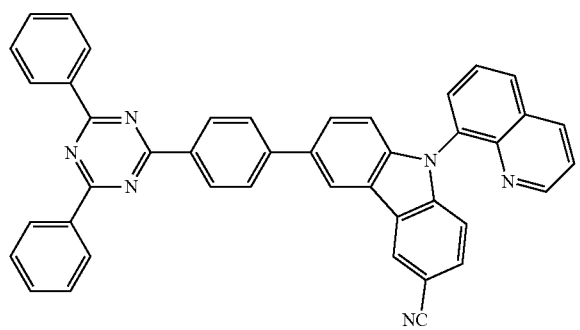
48
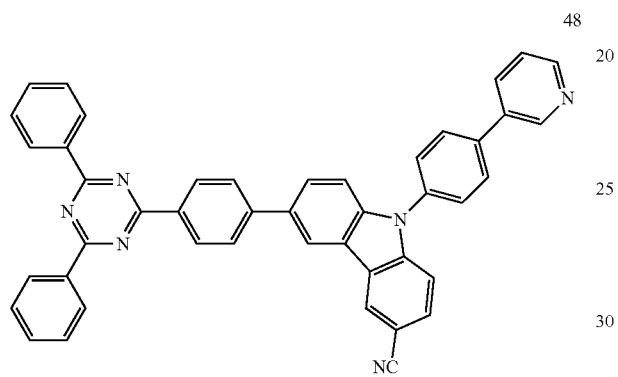
49
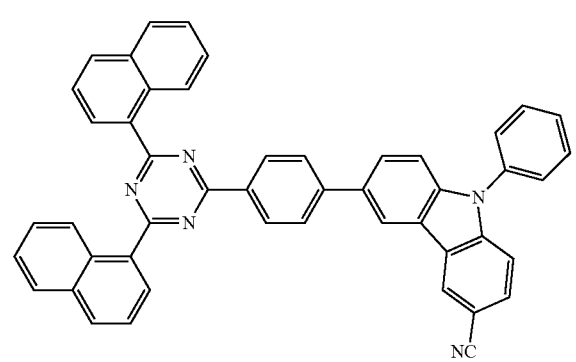
50
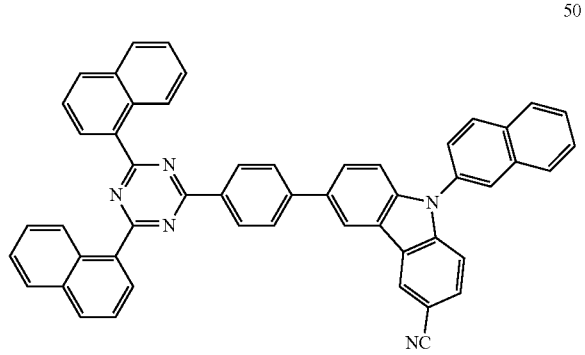
-continued
51
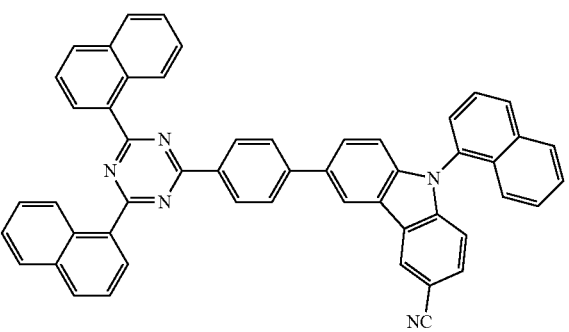
52
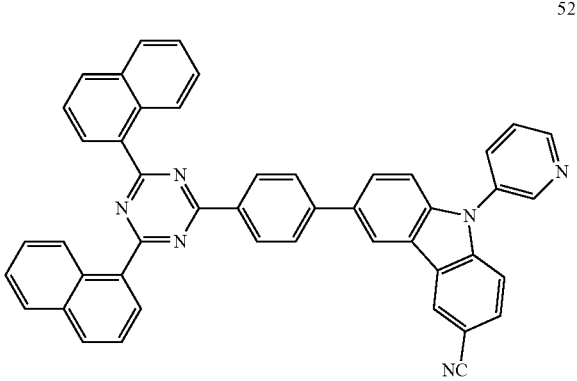
53
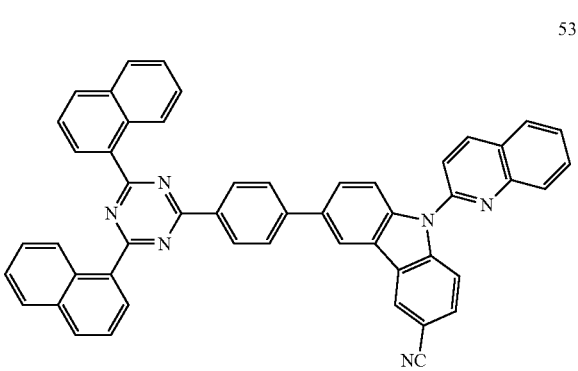
54
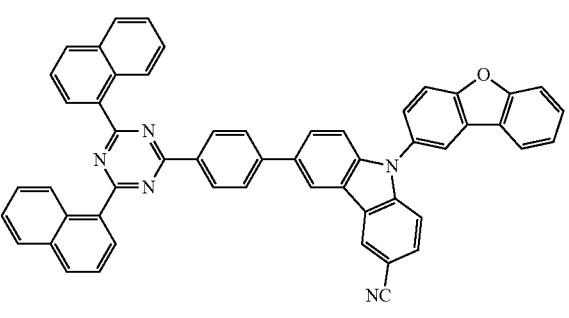

55
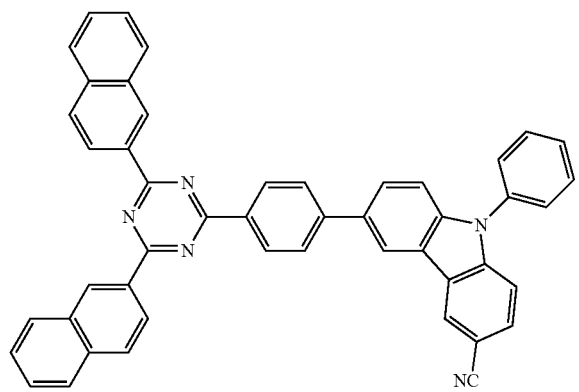
56
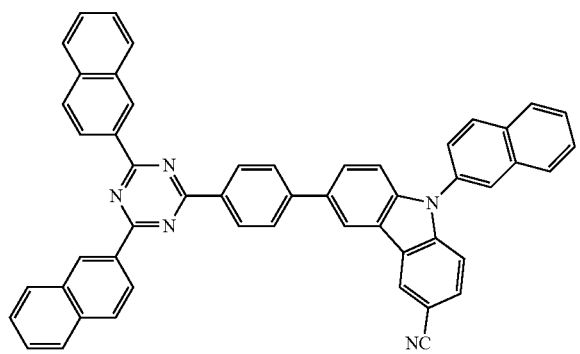
57
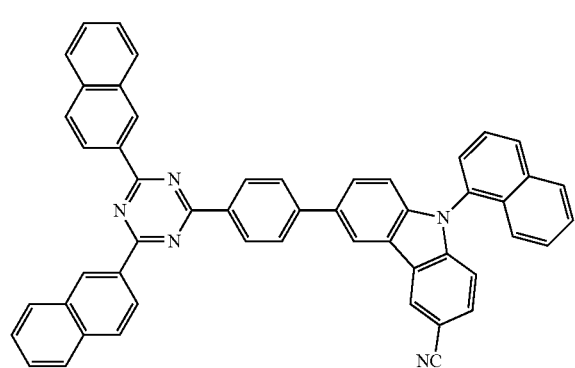
58
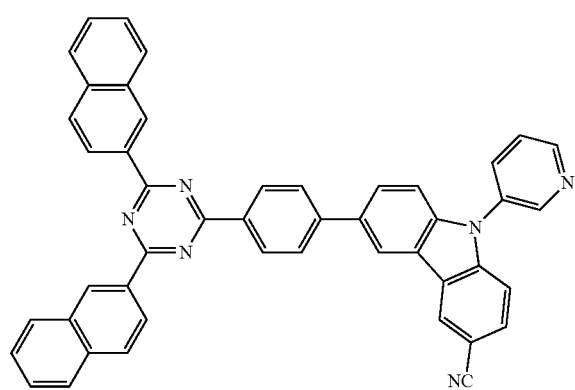
59
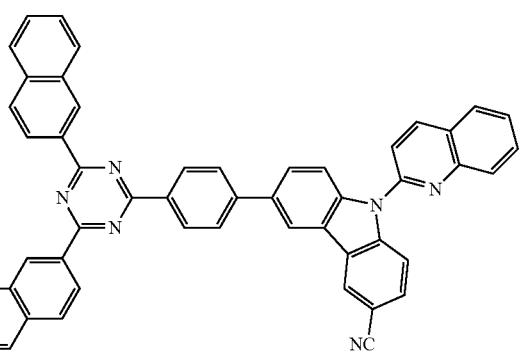
60
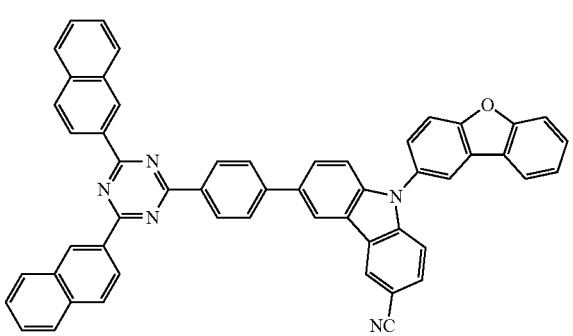
61
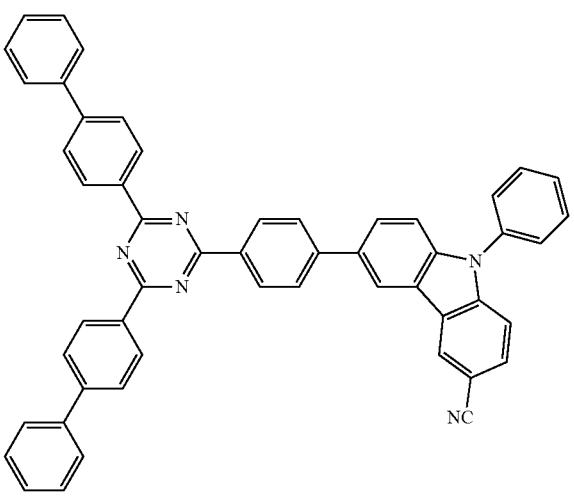

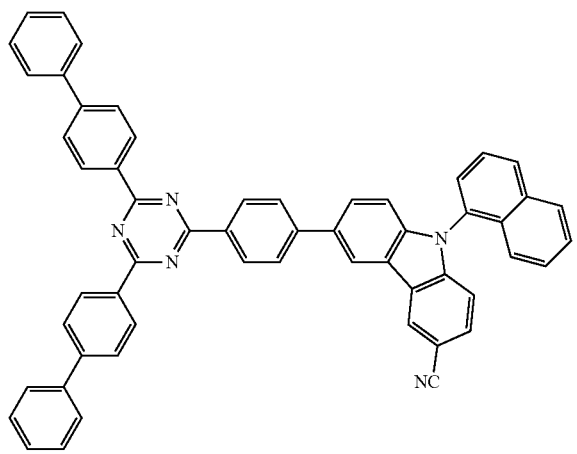
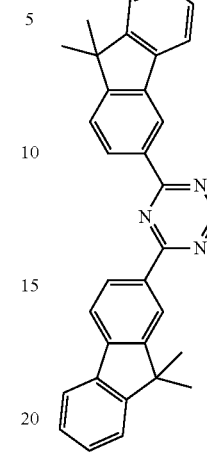
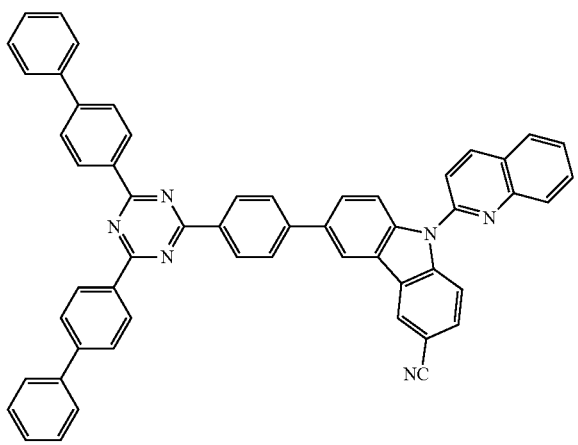
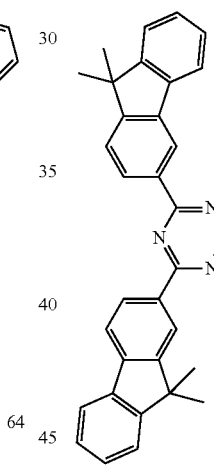
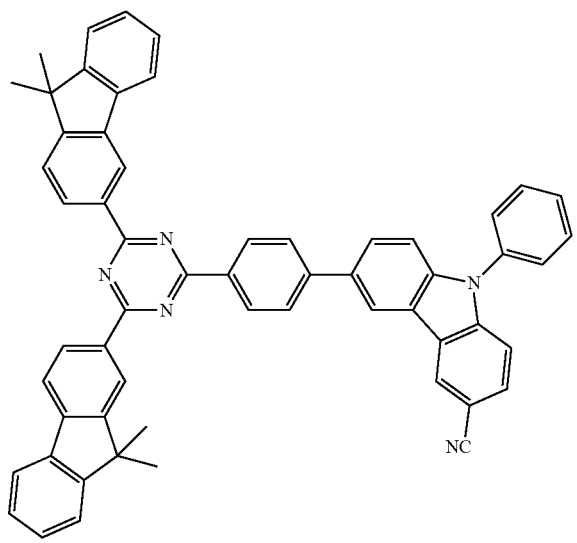
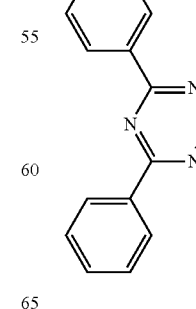

68
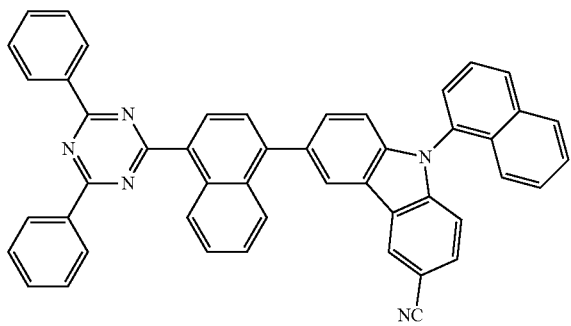
69
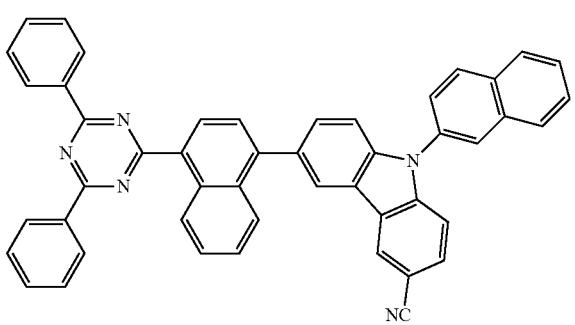
70
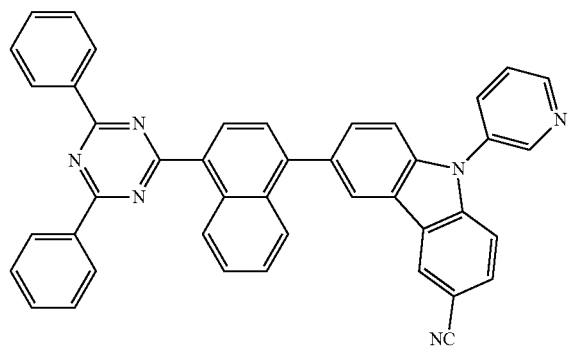
71
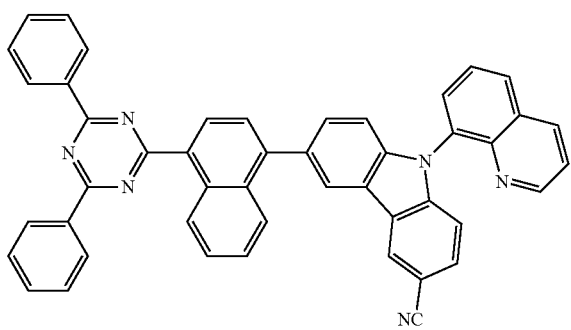
72
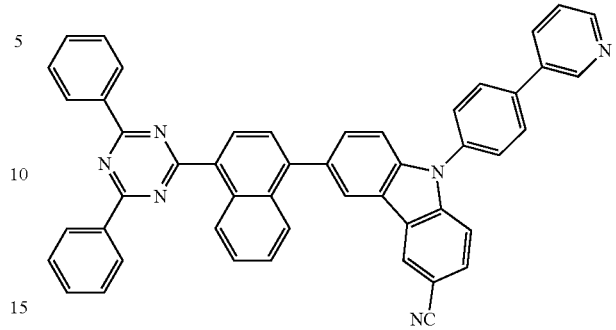
73
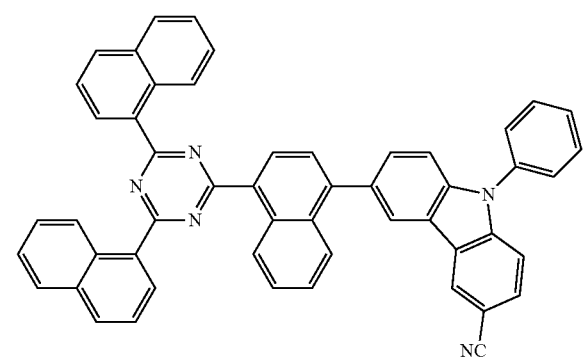
74
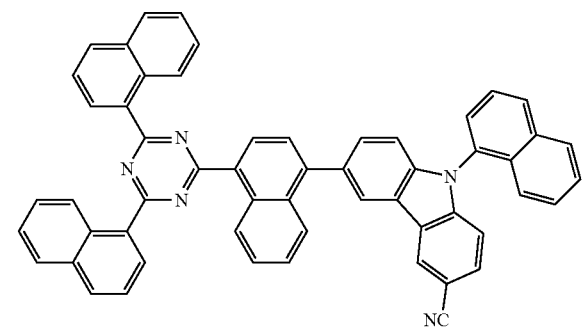
75
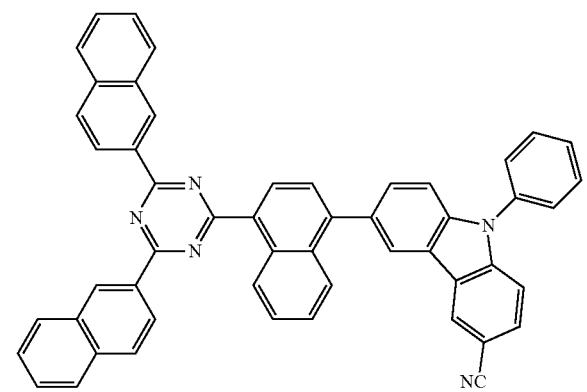

76
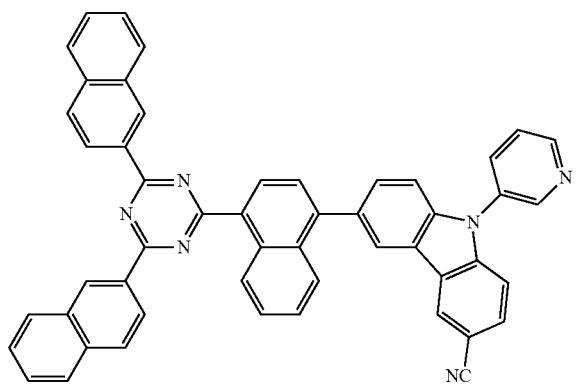
77
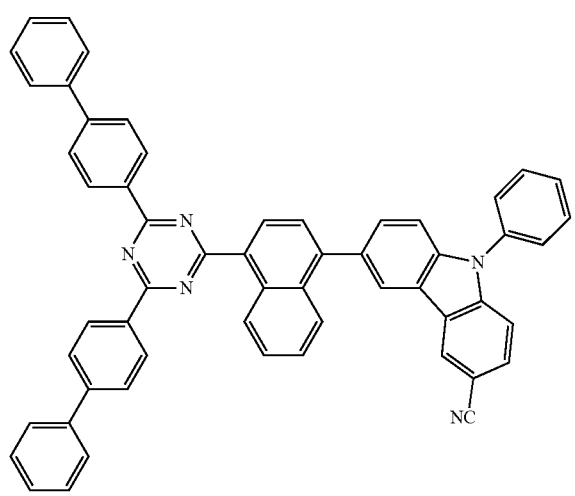
78
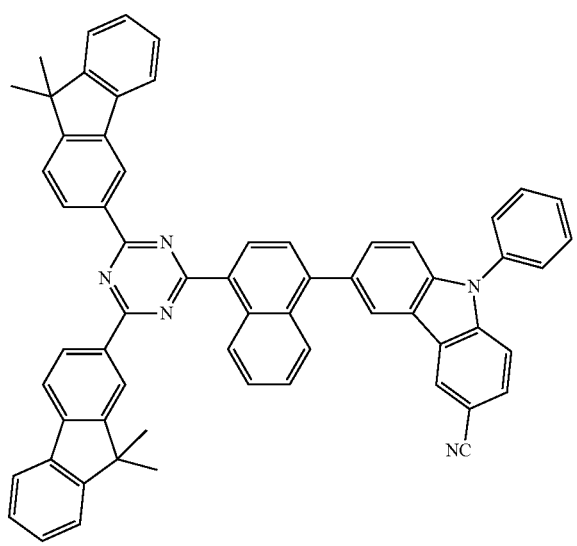
79
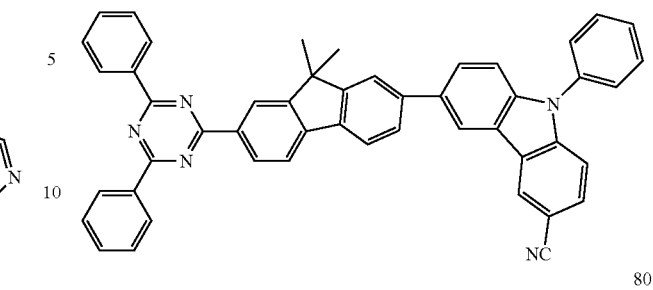
80
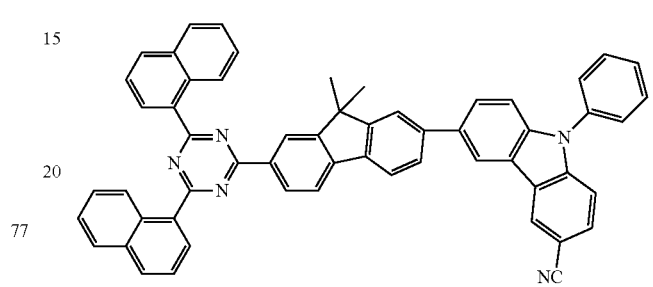
81
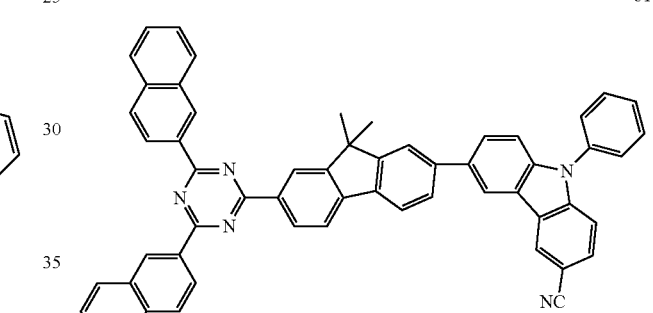
82
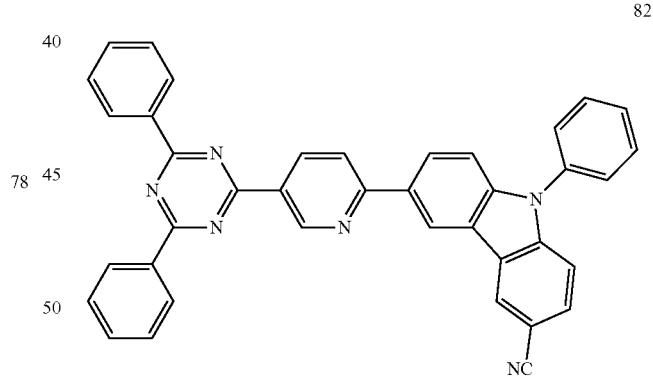
83
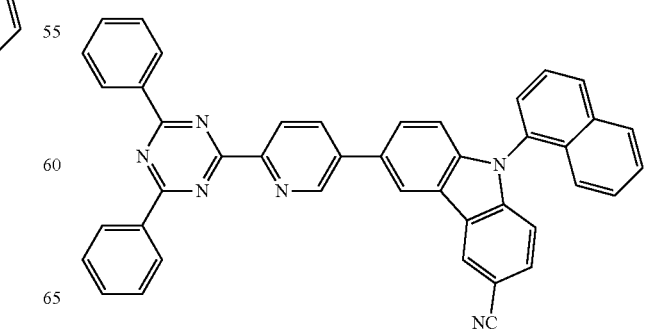

-continued
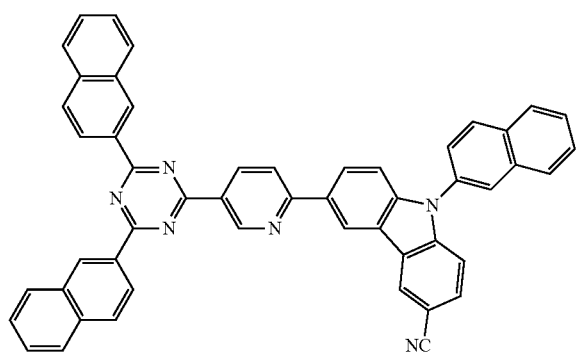
84
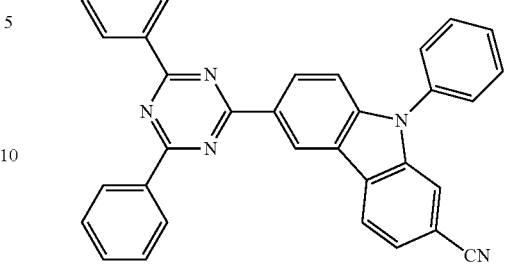
88
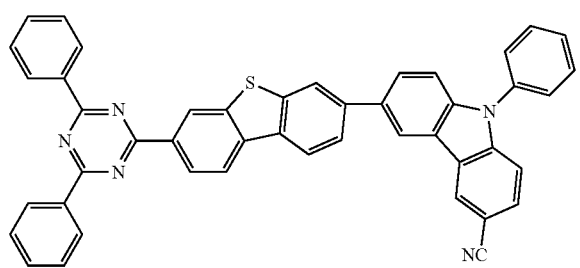
85
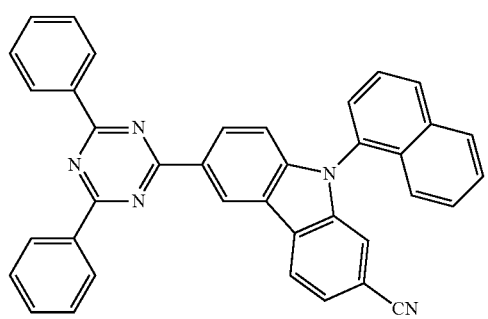
89
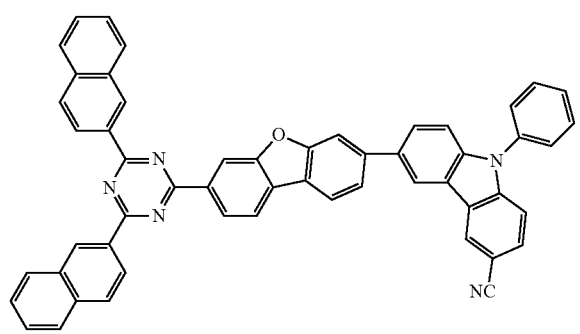
86
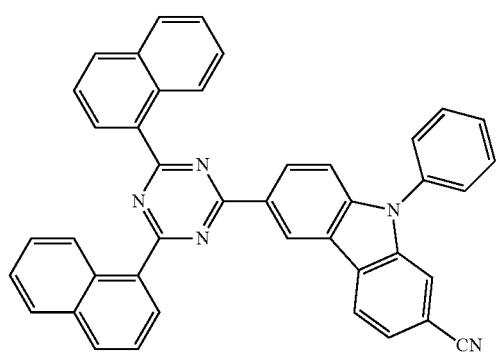
90
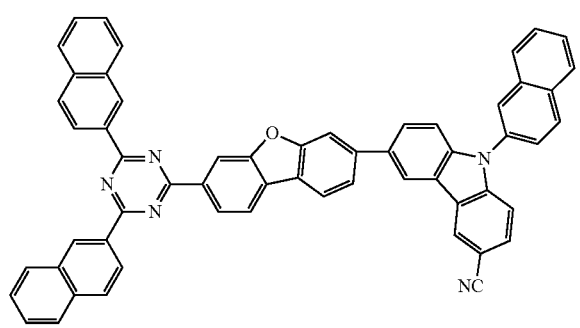
87
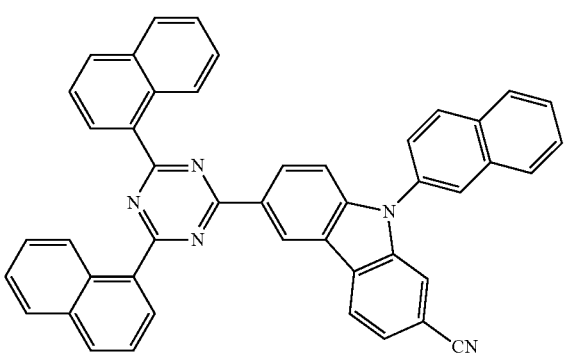
91

92

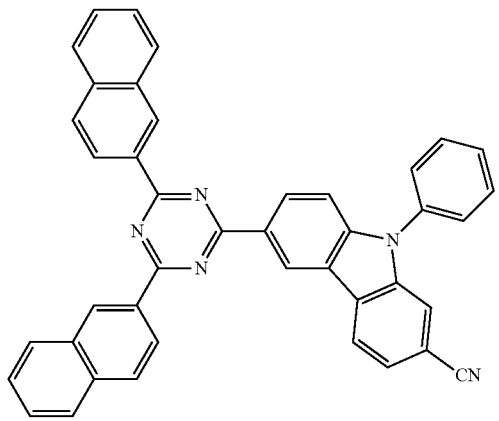

93

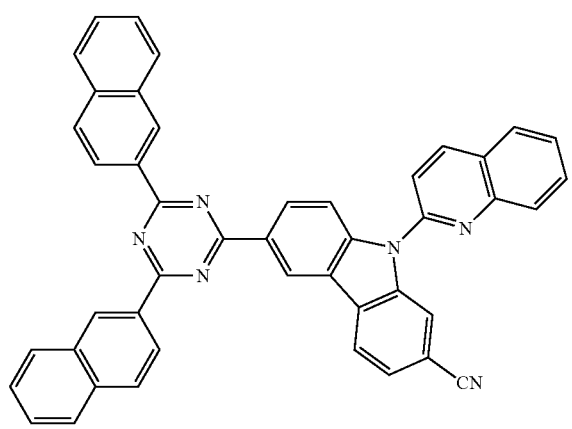

94

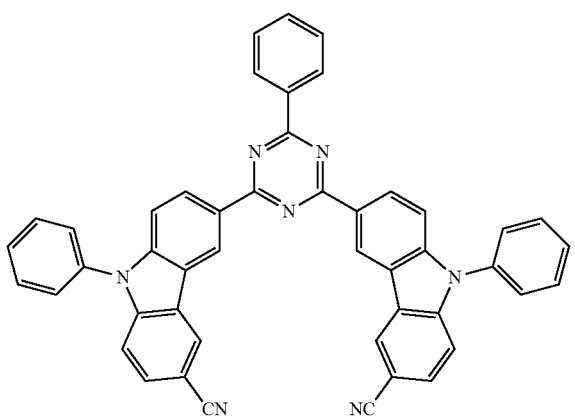

95

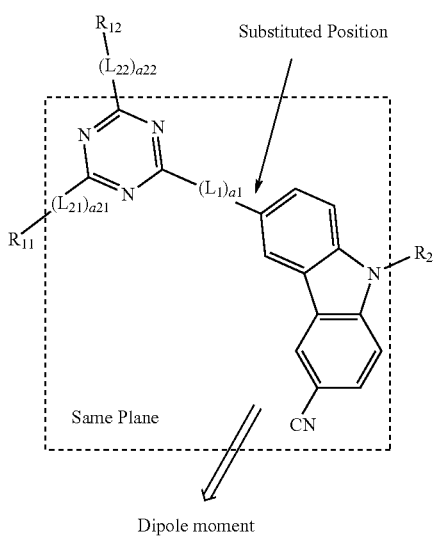

In the triazine-based compound represented by Formula 1, carbon numbers 1 to 4 of a carbazole substituent may bind to a triazine core, thereby connecting the triazine core and the carbazole substituent into a conjugated structure. Accordingly, the triazine-based compound may have the triazine core and the carbazole substituent located on the same plane as illustrated in Formula 1'. Thus, the carbazole substituent in the triazine-based compound may function as a good electron donor.

The triazine-based compound represented by Formula 1 necessarily includes a "carbazole" substituent that is necessarily substituted with a "cyano (CN)".

The triazine-based compound represented by Formula 1 has at least one CN substituted therein as illustrated in Formula 1'. Due to the CN, a large dipole moment is generated in the direction of the arrow illustrated in Formula 1' and thus, a nitrogen atom in the CN may form a coordinate bond with another metal ion included in the electron-injecting layer. Accordingly, an organic light-emitting device including the triazine-based compound represented by Formula 1 may effectively increase electron injection from the cathode into the emission layer.

Carbon number 6 of the carbazole ring may easily form a radical. However, as illustrated in Formula 1', CN may be a substitutent on carbon number 6 of the carbazole ring such that the triazine-based compound represented by Formula 1 may be electrically stable.

Also, because the triazine-based compound represented by Formula 1 includes the "carbazole-based ring" that is "necessarily" substituted with the "CN", an intermolecular bonding force may be enhanced. Accordingly, an organic light-emitting device including the triazine-based compound represented by Formula 1 above may have a long lifespan.

Accordingly, an organic light-emitting device including the triazine-based compound represented by Formula 1 may have low driving voltage, high efficiency, high brightness, and long lifespan.

The triazine-based compound represented by Formula 1 may be synthesized by using (utilizing) a suitable organic synthesis method. A synthesis method of the triazine-based compound may be obvious to one of ordinary skill in the art in view of the following embodiments.

The triazine-based compound of Formula 1 may be used (utilized) between a pair of electrodes of an organic light-emitting device. For example, the triazine-based compound may be included in an electron transport region, for example, in an electron transport layer (ETL). Accordingly, an organic light-emitting device according to an embodiment of the present invention includes: a first electrode; a second electrode facing the first electrode; and an organic layer that is disposed between the first and second electrodes and includes an emission layer, wherein the organic layer includes at least one triazine-based compound represented by Formula 1 described above.

The expression "(an organic layer) includes at least one triazine-based compound" used herein includes a case in which "(an organic layer) includes one kind of triazine-based compound of Formula 1, and a case in which (an organic layer) includes two or more different kinds of triazine-based compounds of Formula 1".

For example, the organic layer may include only Compound 1 as the triazine-based compound. In this regard, Compound 1 may exist in an ETL of the organic light-emitting device. In another embodiment of the present invention, the organic layer may include Compound 1 and Compound 2 as the triazine-based compounds. In this regard, Compound 1 and Compound 2 may exist in the same layer (for example, Compound 1 and Compound 2 may both exist in the ETL, or different layers (for example, Compound 1 may exist in an emission layer and Compound 2 may exist in the ETL).

The organic layer may include i) a hole transport region that is disposed between the first electrode and the emission layer, and includes at least one selected from a hole injection layer, a hole transport layer, a buffer layer, and an electron blocking layer, and ii) an electron transport region that is disposed between the emission layer and the second electrode, and includes at least one selected from a hole blocking layer, an electron transport layer, and an electron injection layer. The electron transport region may include a triazine-based compound represented by Formula 1. For example, the electron transport region may include an electron transport layer including the triazine-based compound represented by Formula 1.

The expression "organic layer" used herein refers to a single layer and/or a plurality of layers disposed between the first and second electrodes of an organic light-emitting device. A material of the "organic layer" is not limited to an organic material.

The drawing is a schematic view of an organic light-emitting device 10 according to an embodiment of the present invention. The organic light-emitting device 10 includes a first electrode 110, an organic layer 150, and a second electrode 190.

Hereinafter, the structure of an organic light-emitting device and a method of manufacturing an organic light-emitting device according to an embodiment of the present invention will be described with reference to the drawing.

In the drawing, a substrate may be additionally disposed under the first electrode 110 or above the second electrode 190. The substrate may be a glass substrate or a transparent plastic substrate, each with excellent mechanical strength, thermal stability, transparency, surface smoothness, ease of handling, and water repellency.

The first electrode 110 may be formed by depositing or sputtering a material for forming the first electrode 110 on the substrate. When the first electrode 110 is an anode, the material for the first electrode 110 may be selected from materials with a high work function for an easy hole injection. The first electrode 110 may be a reflective electrode, a semi-transmissive electrode, or a transmissive electrode. The material for the first electrode 110 may be a transparent and highly conductive material, and examples of such a material are indium tin oxide (ITO), indium zinc oxide (IZO), tin oxide ($SnO_2$), and zinc oxide (ZnO). When the first electrode 110 is a semi-transmissive electrode or a reflective electrode, a material for forming the first electrode 110 may include at least one selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure, or a multi-layer structure including two or more layers. For example, the first electrode 110 may have a three-layered structure of ITO/Ag/ITO, but the structure of the first electrode 120 is not limited thereto.

The organic layer 150 is disposed on the first electrode 110. The organic layer 150 may include an emission layer.

The organic layer 150 may further include a hole transport region disposed between the first electrode 110 and the emission layer, and an electron transport region disposed between the emission layer and the second electrode 190.

The hole transport region may include at least one selected from a hole injection layer (HIL), a hole transport layer (HTL), a buffer layer, and an electron blocking layer (EBL); and the electron transport region may include at least one selected from a hole blocking layer (HBL), an electron transport layer (ETL), and an electron injection layer (EIL), but the hole transport region and the electron transport region are not limited thereto.

The hole transport region may have a single-layered structure formed of a single material, a single-layered structure formed of different materials, or a multi-layered structure having a plurality of layers formed of different materials.

For example, the hole transport region may have a single-layered structure formed of different materials, or a structure of HIL/HTL, a structure of HIL/HTL/buffer layer, a structure of HIL/buffer layer, a structure of HTL/buffer layer, or a structure of HIL/HTL/EBL, wherein layers of each structure are sequentially stacked from the first electrode 110 in the stated order, but are not limited thereto.

When the hole transport region includes an HIL, the HIL may be formed on the first electrode 110 by using (utilizing) various suitable methods, such as vacuum deposition, spin coating, casting, a Langmuir-Blodgett (LB) method, ink-jet printing, laser-printing, or laser-induced thermal imaging.

When an HIL is formed by vacuum deposition, for example, the vacuum deposition may be performed at a deposition temperature of about 100 to about 500° C., at a vacuum degree of about $10^{-8}$ to about $10^{-3}$ torr, and at a deposition rate of about 0.01 to about 100 Å/sec in consideration of a compound for an HIL to be deposited, and the structure of an HIL to be formed.

When an HIL is formed by spin coating, the spin coating may be performed at a coating rate of about 2000 rpm to about 5000 rpm, and at a temperature of about 80° C. to 200° C. in consideration of a compound for a hole injection layer to be deposited, and the structure of an HIL to be formed.

When the hole transport region includes an HTL, the HTL may be formed on the first electrode 110 or the HIL by using (utilizing) various suitable methods, such as vacuum deposition, spin coating, casting, an LB method, ink-jet printing, laser-printing, or laser-induced thermal imaging. When the HTL is formed by vacuum deposition or spin coating, deposition and coating conditions for the HTL may be determined by referring to the deposition and coating conditions for the HIL.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), phenylamine(4,4',4"-tris(N-carbazolyl)triphenylamine)), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201 below, and a compound represented by Formula 202 below:

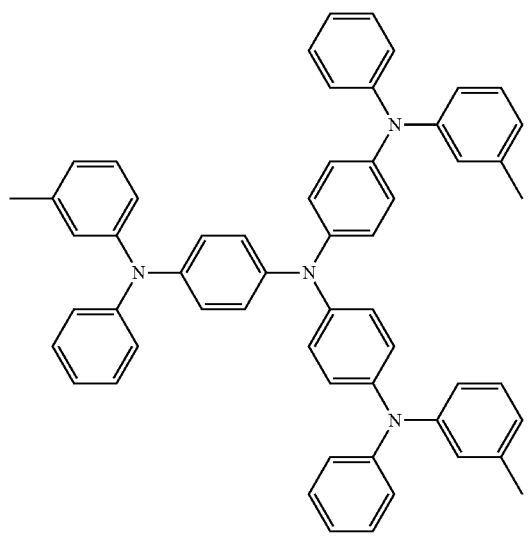

m-MTDATA

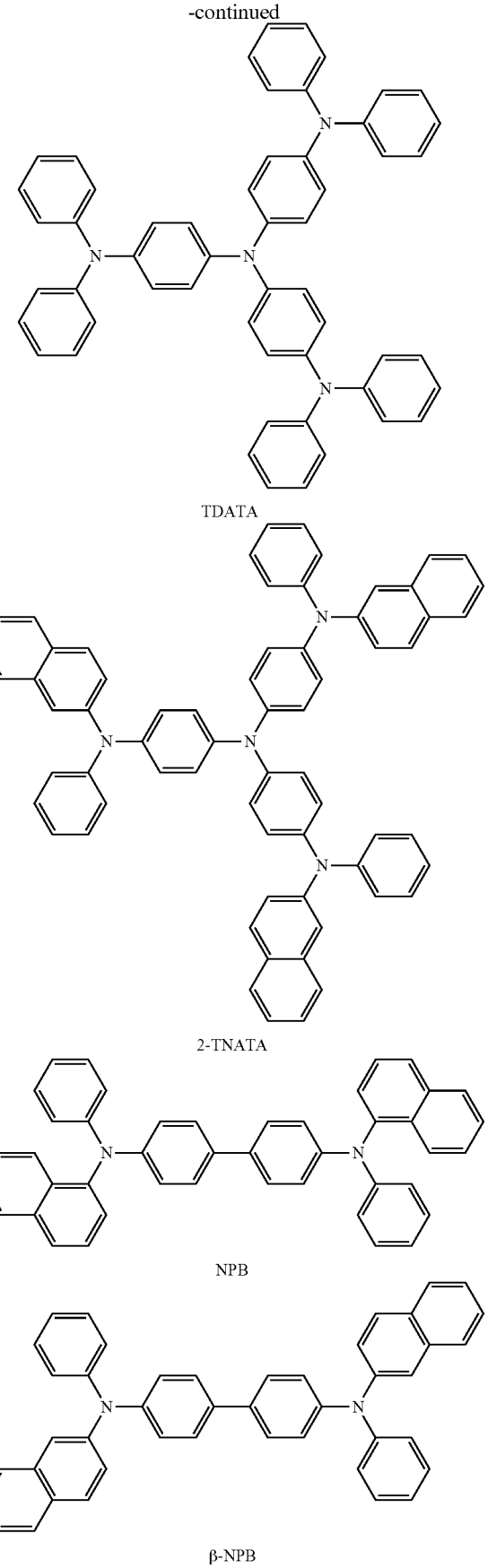

TDATA

2-TNATA

NPB

β-NPB

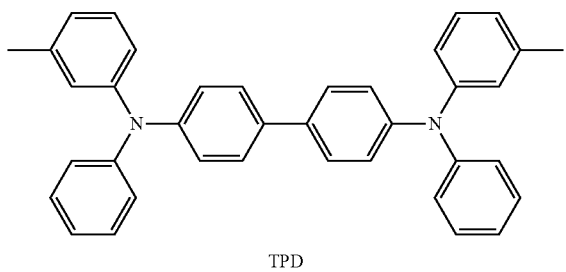
TPD

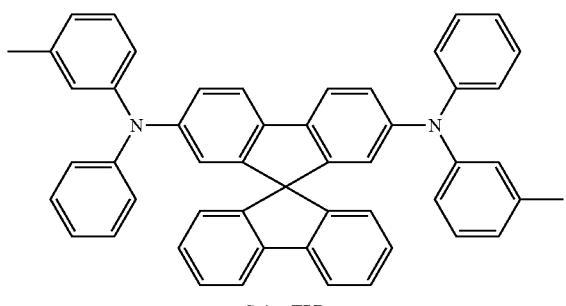
Spiro-TPD

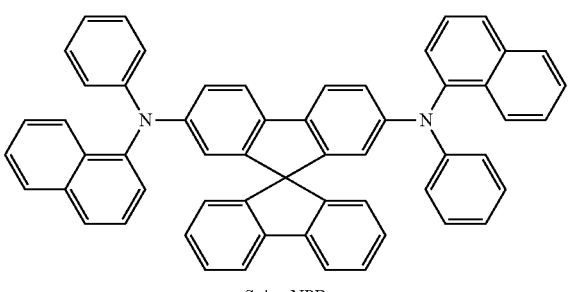
Spiro-NPB

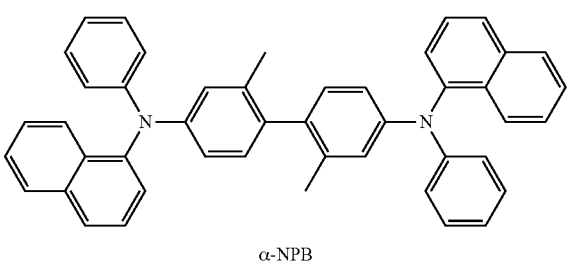
α-NPB

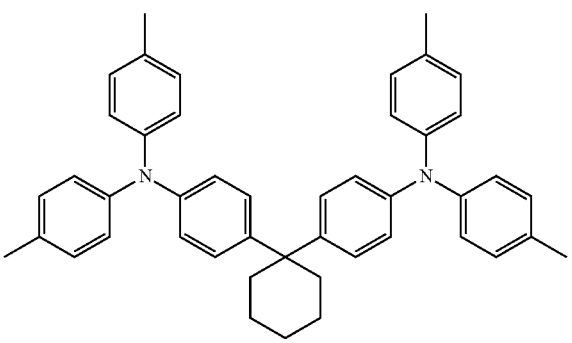
TAPC

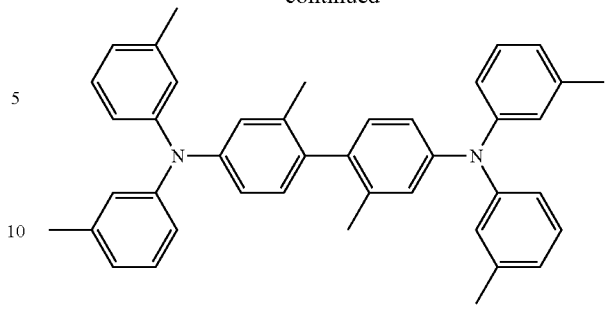
HMTPD

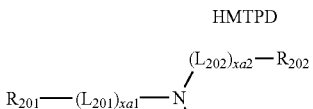
Formula 201

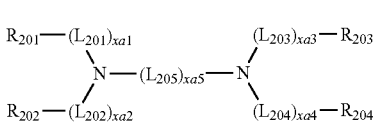
Formula 202

In Formula 201 and 202,
descriptions of $L_{201}$ to $L_{205}$ are each independently the same as the description of $L_1$;
xa1 to xa4 are each independently selected from 0, 1, 2, and 3;
xa5 is selected from 1, 2, 3, 4, and 5; and
$R_{201}$ to $R_{204}$ are each independently the same as the description of $R_2$.

For example, in Formulae 201 and 202,
$L_{201}$ to $L_{205}$ may be each independently selected from:
a phenylene, a naphthylene, a fluorenylene, a spirofluorenylene, benzofluorene, dibenzofluorene, a phenanthrenylene, anthracenylene, pyrenylene, a chrysenylene, a pyridinylene, a pyrazinylene, a pyrimidinylene, a pyridazinylene, a quinolinylene, an isoquinolinylene, a quinoxalinylene, a quinazolinylene, a carbazolylene, and a triazinylene; and
a phenylene, a naphthylene, a fluorenylene, a spirofluorenylene, a benzofluorenylene, a dibenzofluorenylene, a phenanthrenylene, anthracenylene, pyrenylene, a chrysenylene, a pyridinylene, a pyrazinylene, a pyrimidinylene, a pyridazinylene, a quinolinylene, an isoquinolinylene, a quinoxalinylene, a quinazolinylene, a carbazolylene, and a triazinylene, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, an isoindolyl, a quinolinyl, an isoquinolinyl, a quinoxalinyl, a quinazolinyl, a carbazolyl, and a triazinyl;
xa1 to xa4 may be each independently 0, 1, or 2;
xa5 may be 1, 2, or 3;
$R_{201}$ to $R_{205}$ may be each independently selected from,
a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl; and a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, a phenyl, a naphthyl, an azulenyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl.

The compounds represented by Formula 201 may be represented by Formula 201A:

Formula 201A

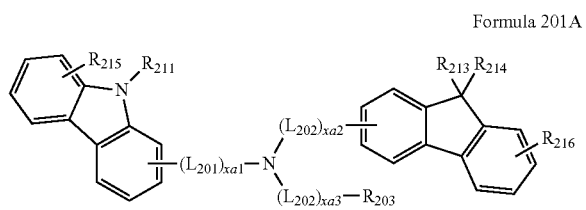

For example, the compound represented by Formula 201 may be represented by Formula 201A-1, but it is not limited thereto:

Formula 201A-1

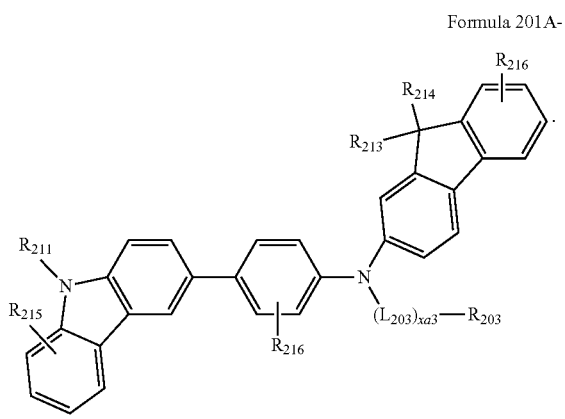

The compound represented by Formula 202 may be represented by Formula 202A, but it is not limited thereto:

Formula 202A

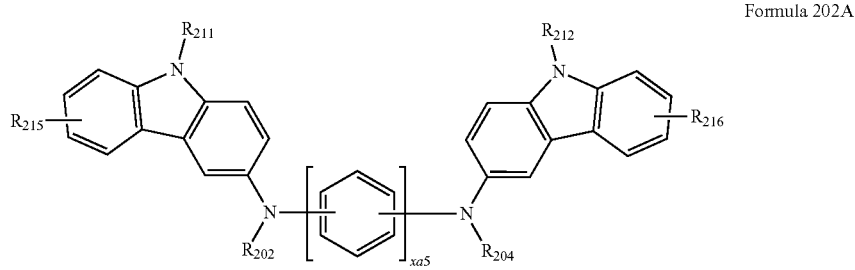

In Formula 201A, 201A-1, and 202A, descriptions of $L_{201}$ to $L_{203}$, xa1 to xa3, xa5, and $R_{202}$ to $R_{204}$ are as described above; descriptions of $R_{211}$ are the same as the description of $R_{203}$; and $R_{213}$ to $R_{216}$ may be each independently selected from a hydrogen, a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_2$-$C_{60}$ heteroaryl, a non-aromatic condensed polycyclic group, and a non-aromatic hetero-condensed polycyclic group.

For example, in Formula 201A, 201A-1, and 202A, $L_{201}$ to $L_{203}$ may be each independently selected from:

a phenylene, a naphthylene, a fluorenylene, a spiro-fluorenylene, a benzofluorenylene, a dibenzofluorenylene, a phenanthrenylene, anthracenylene, pyrenylene, a chrysenylene, a pyridinylene, a pyrazinylene, a pyrimidinylene, a pyridazinylene, a quinolinylene, an isoquinolinylene, a quinoxalinylene, a quinazolinylene, a carbazolylene, and a triazinylene; and a phenylene, a naphthylene, a fluorenylene, a spiro-fluorenylene, a benzofluorenylene, a dibenzofluorenylene, a phenanthrenylene, anthracenylene, pyrenylene, a chrysenylene, a pyridinylene, a pyrazinylene, a pyrimidinylene, a pyridazinylene, a quinolinylene, an isoquinolinylene, a quinoxalinylene, a quinazolinylene, a carbazolylene, and a triazinylene, each independently substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl;

xa1 to xa3 may be each independently 0 or 1;

$R_{203}$, $R_{211}$, and $R_{212}$ are each independently selected from:

a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl; and a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, $C_1$-$C_{20}$ alkyl, $C_1$-$C_{20}$ alkoxy, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl;

$R_{213}$ and $R_{214}$ are each independently selected from:

a $C_1$-$C_{20}$ alkyl and a $C_1$-$C_{20}$ alkoxy;

a $C_1$-$C_{20}$ alkyl and a $C_1$-$C_{20}$ alkoxy, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl and a triazinyl;

a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl; and a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl;

$R_{215}$ and $R_{216}$ are each independently selected from, a hydrogen, a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl and a $C_1$-$C_{20}$ alkoxy;

a $C_1$-$C_{20}$ alkyl and a $C_1$-$C_{20}$ alkoxy, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl;

a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, and a triazinyl; and a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, a phenyl, a naphthyl, a fluorenyl, a spires-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl; and xa5 is 1 or 2.

In Formulae 201A and 201A-1, $R_{213}$ and $R_{214}$ may bind to each other to form a saturated or unsaturated ring.

The compounds represented by Formula 201 and Formula 202 may include Compounds HT1 to HT20, but they are not limited thereto.

HT1

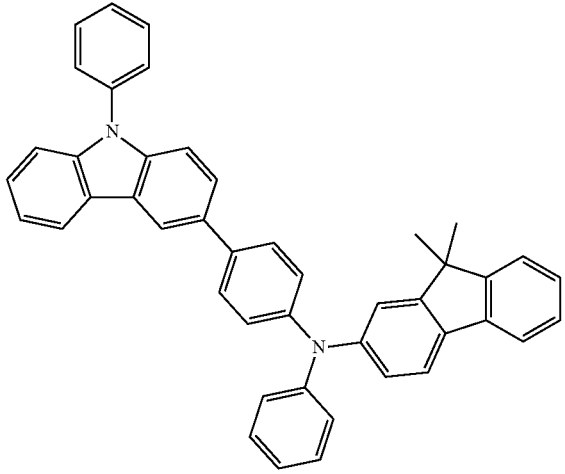

HT2

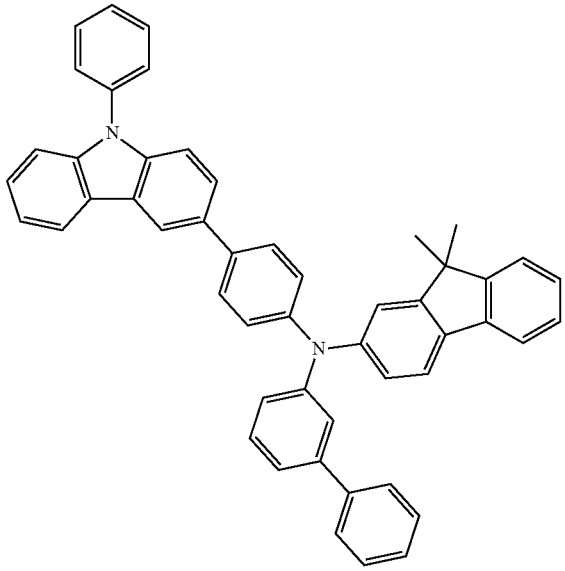

HT3
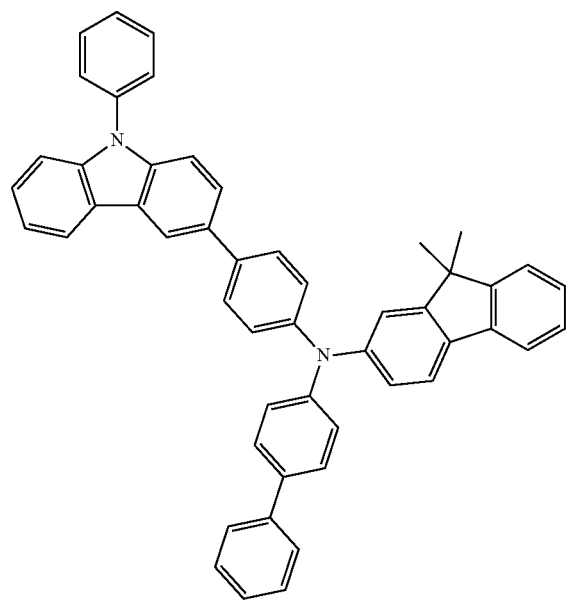
HT5
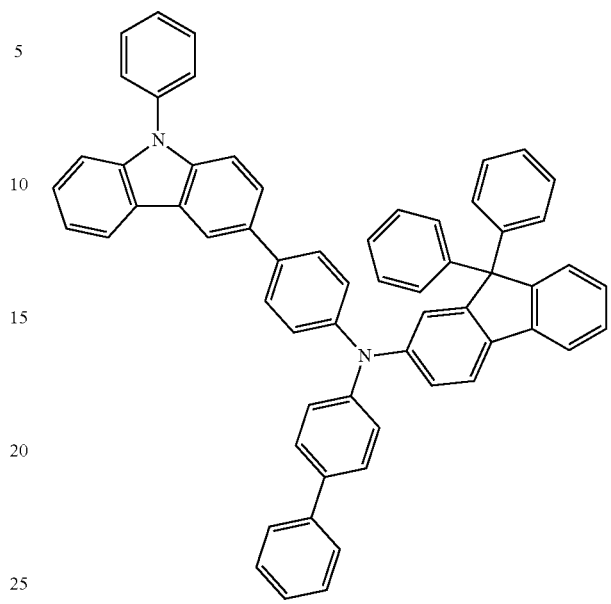
HT4
HT6

HT7
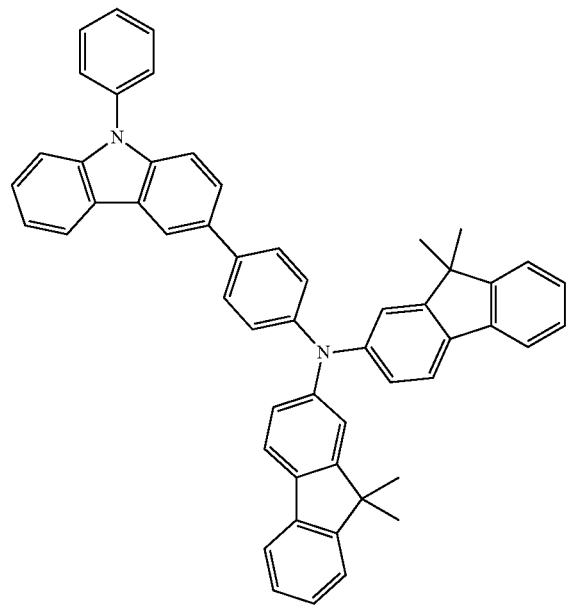
HT9
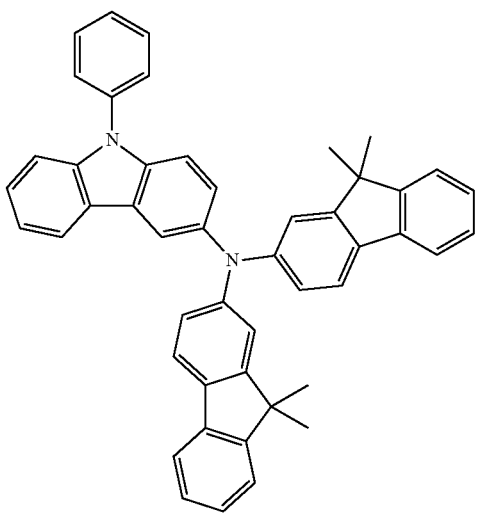
HT8
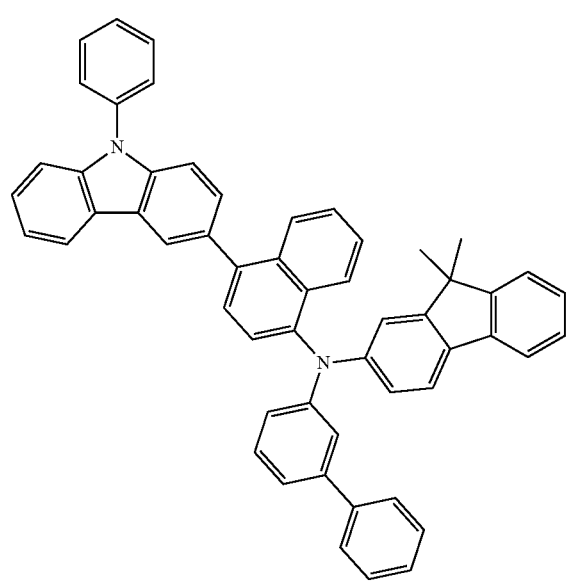
HT10
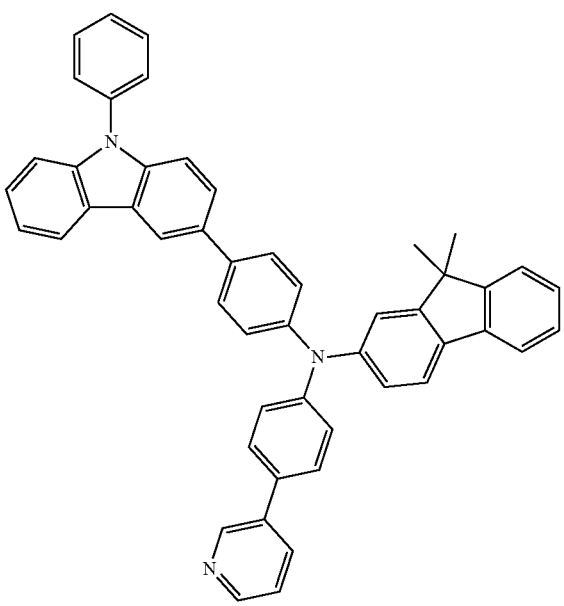

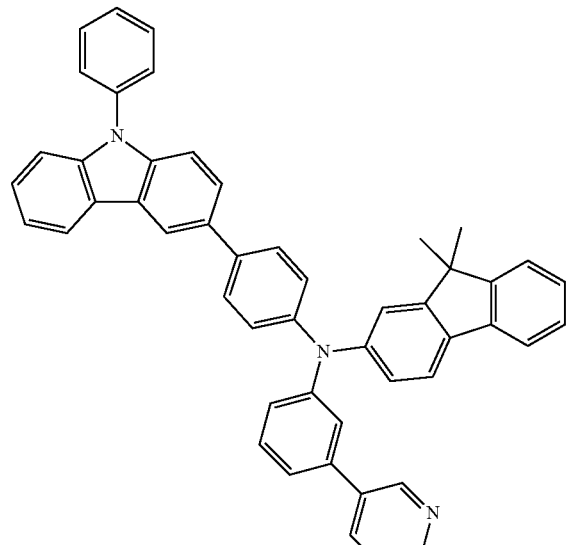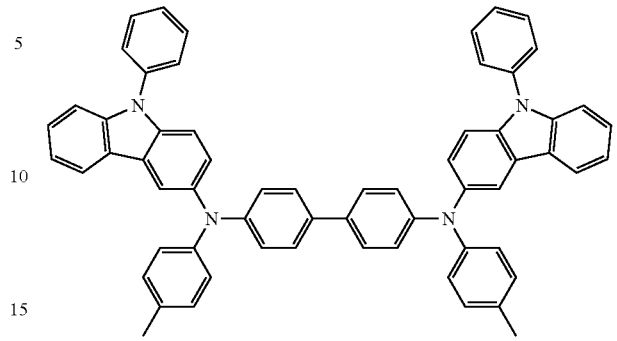

HT18

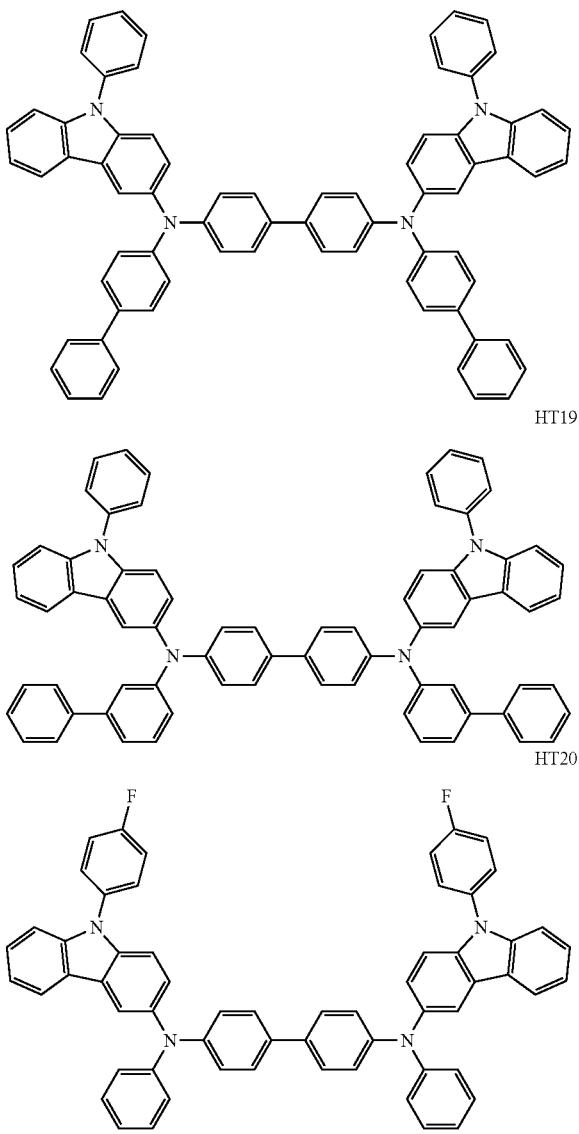

HT19

HT20

A thickness of the hole transport region may be in a range of about 100 Å to about 10000 Å, for example, about 100 Å to about 1000 Å. When the hole transport region includes an HIL and an HTL, a thickness of the HIL may be in a range of about 100 Å to about 10000 Å, for example, about 100 Å to about 1000 Å, and a thickness of the HTL may be in a range of about 50 Å to about 2000 Å, for example, about 100 Å to about 1500 Å. In one embodiment, when the thicknesses of the hole transport region, the HIL, and the HTL are within these ranges, satisfactory hole transporting characteristics are obtained without a substantial increase in driving voltage.

The hole transport region may further include, in addition to these materials, a charge-generating material for the improvement of conductive properties. The charge-generating material may be homogeneously or non-homogeneously dispersed in the hole transport region.

The charge-generating material may be, for example, a p-dopant. The p-dopant may be one of a quinone derivative, a metal oxide, and a cyano group-containing compound, but is not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and Compound HT-D1 illustrated below, but are not limited thereto.

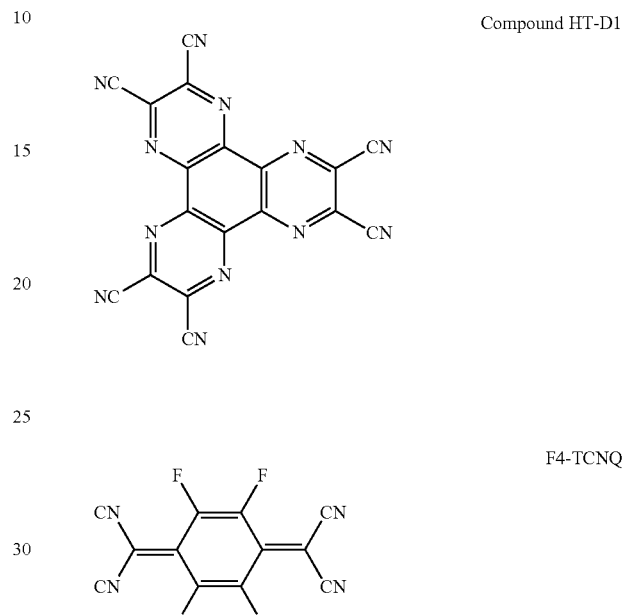

Compound HT-D1

F4-TCNQ

The hole transport region may further include, in addition to the HIL and the HTL, at least one selected from a buffer layer and an EBL. The buffer layer may compensate for an optical resonance distance according to a wavelength of light emitted from the EML, and thus, a light-emission efficiency of an organic light-emitting device may be improved. For a material of the buffer layer, materials of the hole transport region may be used (utilized). The EBL reduces or prevents injection of electrons from the electron transport region.

An EML is formed on the first electrode 110 or the hole transport region by using (utilizing) various suitable methods, such as vacuum deposition, spin coating, casting, an LB method, ink-jet printing, laser-printing, or laser-induced thermal imaging. When the EML is formed by vacuum deposition or spin coating, deposition and coating conditions for the EML may be determined by referring to the deposition and coating conditions for the HIL.

When the organic light-emitting device 10 is a full color organic light-emitting device, the EML may be patterned into a red EML, a green EML, and a blue EML, according to a sub-pixel. In some embodiments, the EML may have a stacked structure of a red EML, a green EML, and a blue EML, or may include a red-light emission material, a green-light emission material, and a blue-light emission material, which are mixed with each other in a single layer, to emit white light.

The EML may include a host and a dopant.

The host may include at least one selected from TPBi, TBADN, AND (also referred to as "DNA"), CBP, CDBP, and TCP:

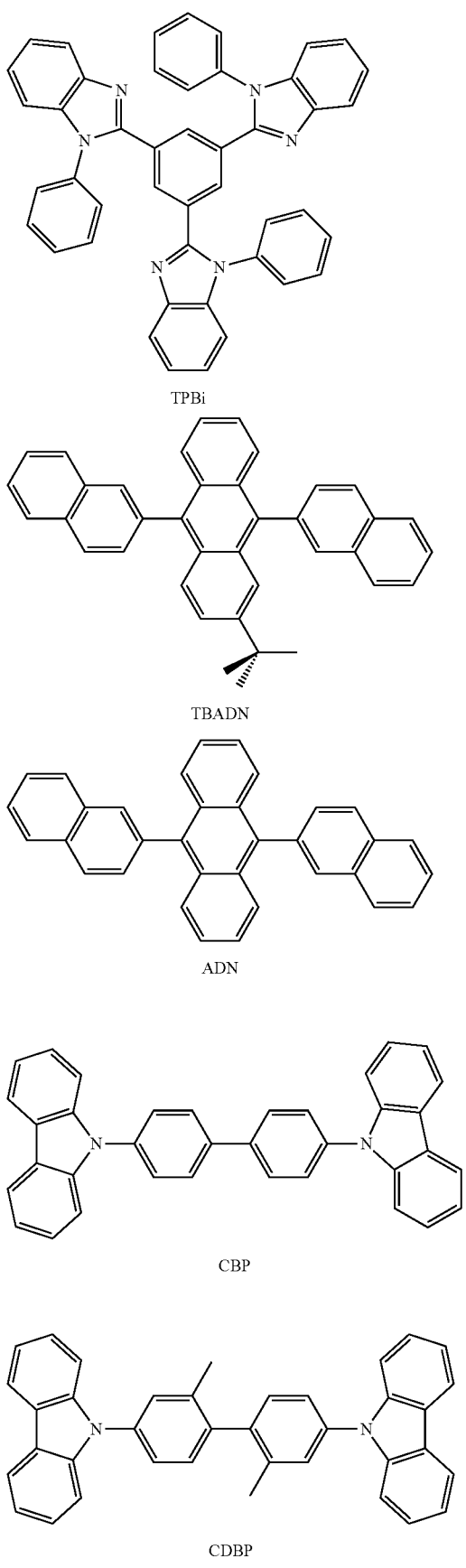

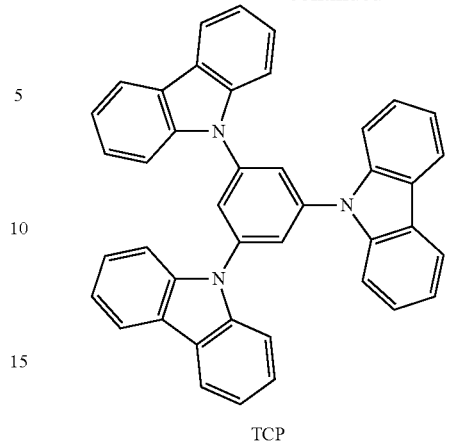

According to another embodiment of the present invention, the host may include a compound represented by Formula 301 below.

$$Ar_{301}\text{-}[(L_{301})_{xb1}\text{-}R_{301}]_{xb2} \qquad \text{Formula 301}$$

in Formula 301,

Ar$_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_2$-$C_{60}$ heteroaryl, a non-aromatic condensed polycyclic group, a non-aromatic hetero-condensed polycyclic group, and —Si(Q$_{301}$)(Q$_{302}$)(Q$_{303}$) (wherein, Q$_{301}$ to Q$_{303}$ may be each independently selected from a hydrogen, a $C_1$-$C_{60}$ alkyl, a $C_2$-$C_{60}$ alkenyl, a $C_6$-$C_{60}$ aryl, and a $C_2$-$C_{60}$ heteroaryl);

Description of L$_{301}$ may be the same as the description of L$_{201}$;

R$_{301}$ may be selected from:

a $C_1$-$C_{20}$ alkyl and a $C_1$-$C_{20}$ alkoxy;

a $C_1$-$C_{20}$ alkyl and a $C_1$-$C_{20}$ alkoxy, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl;

a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazole, and a triazinyl; and a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, and a triazinyl;

xb1 may be selected from 0, 1, 2, and 3;
xb2 may be selected from 1, 2, 3, and 4.
For example, in Formula 301,
$L_{301}$ may be selected from:
a phenylene, a naphthylene, a fluorenylene, a spiro-fluorenylene, a benzofluorenylene, a dibenzofluorenylene, a phenanthrenylene, anthracenylene, pyrenylene, and a chrysenylene; and a phenylene, a naphthylene, a fluorenylene, a spiro-fluorenylene, a benzofluorenylene, a dibenzofluorenylene, a phenanthrenylene, anthracenylene, pyrenylene, and a chrysenylene, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, a phenyl, a naphthyl, a fluorenyl, a spiro-fluorenyl, a benzofluorenyl, a dibenzofluorenyl, a phenanthrenyl, an anthracenyl, a pyrenyl, and a chrysenyl;

In one embodiment, $R_{301}$ may be selected from:
a $C_1$-$C_{20}$ alkyl and a $C_1$-$C_{20}$ alkoxy;
a $C_1$-$C_{20}$ alkyl and a $C_1$-$C_{20}$ alkoxy, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a phenyl, a naphthyl, a fluorenyl, a spiro-fluorenyl, a benzofluorenyl, a dibenzofluorenyl, a phenanthrenyl, an anthracenyl, a pyrenyl, and a chrysenyl;

a phenyl, a naphthyl, a fluorenyl, a spiro-fluorenyl, a benzofluorenyl, a dibenzofluorenyl, a phenanthrenyl, an anthracenyl, a pyrenyl and a chrysenyl; and a phenyl, a naphthyl, a fluorenyl, a spiro-fluorenyl, a benzofluorenyl, a dibenzofluorenyl, a phenanthrenyl, an anthracenyl, a pyrenyl, and a chrysenyl, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, $C_1$-$C_{20}$ alkyl, $C_1$-$C_{20}$ alkoxy, a phenyl, a naphthyl, a fluorenyl, a spiro-fluorenyl, a benzofluorenyl, a dibenzofluorenyl, a phenanthrenyl, an anthracenyl, a pyrenyl, and a chrysenyl, but they are not limited thereto.

For example, the host may include a compound represented by Formula 301A:

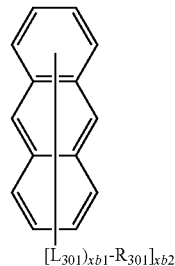

Formula 301A

Substituents of Formula 301A are already described above.

The compound represented by Formula 301 may include at least one of Compounds H1 to H42, but is not limited thereto:

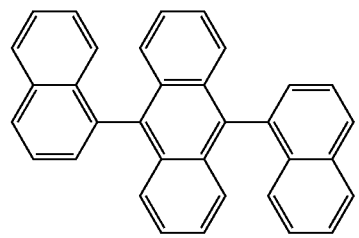

H1

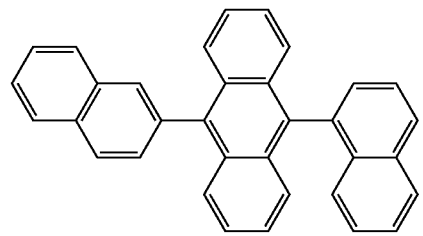

H2

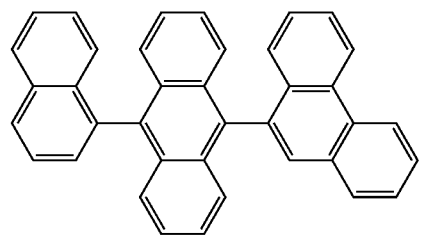

H3

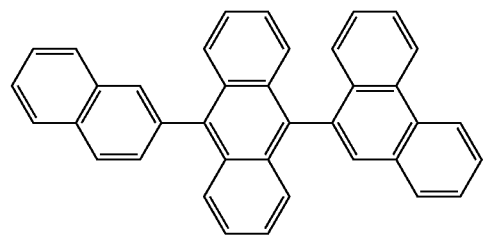

H4

-continued
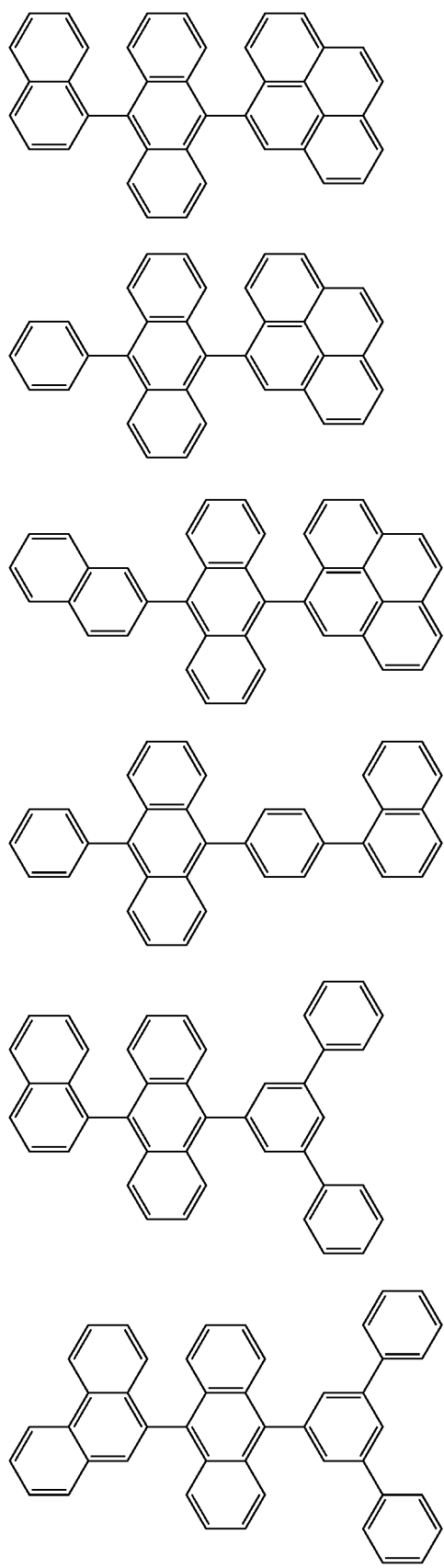
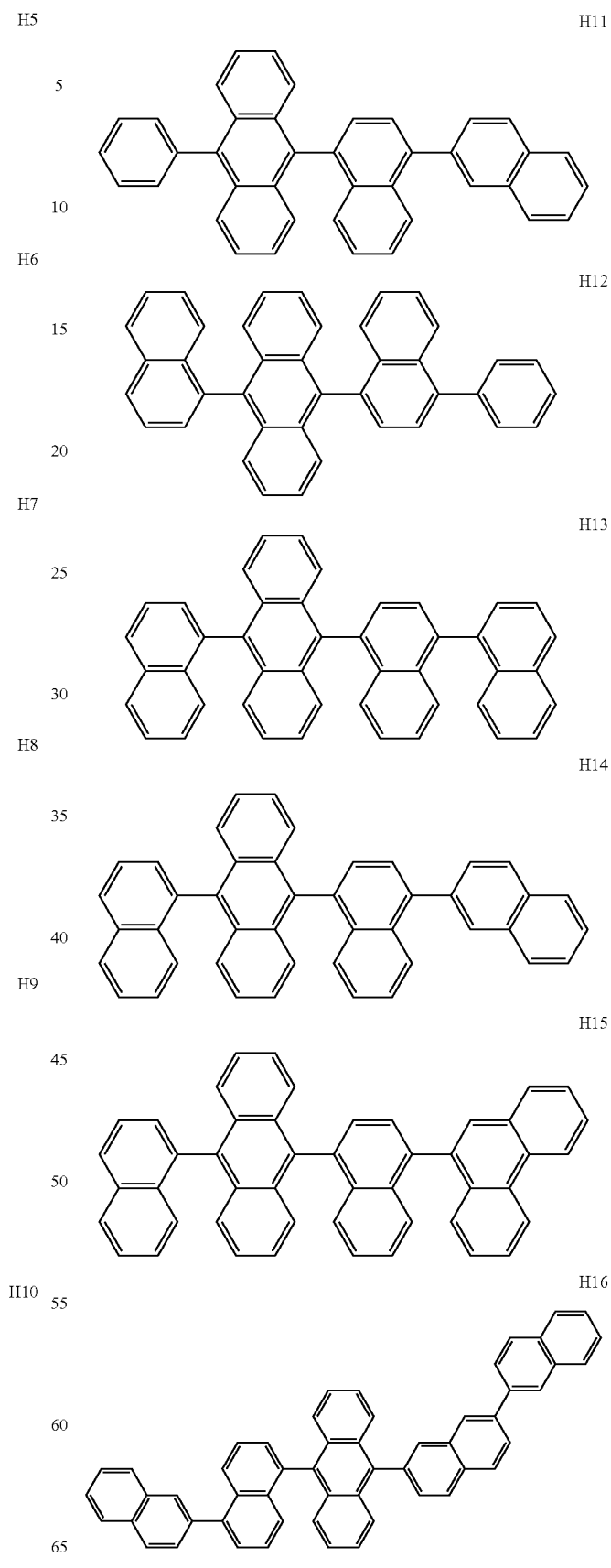

H17
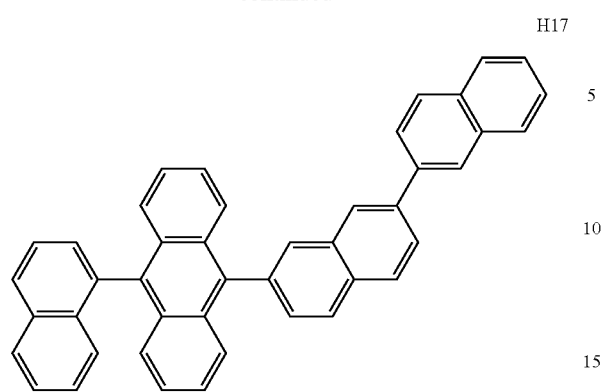
H18
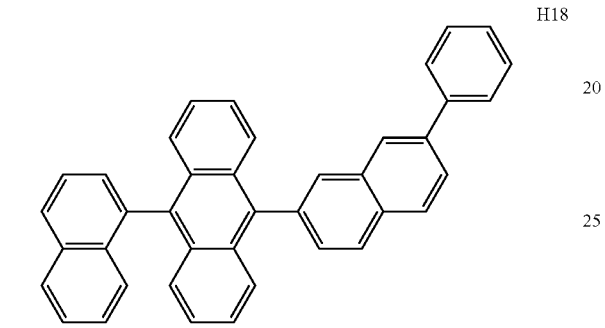
H19
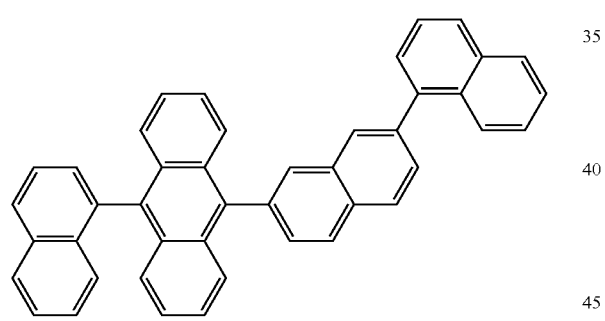
H20
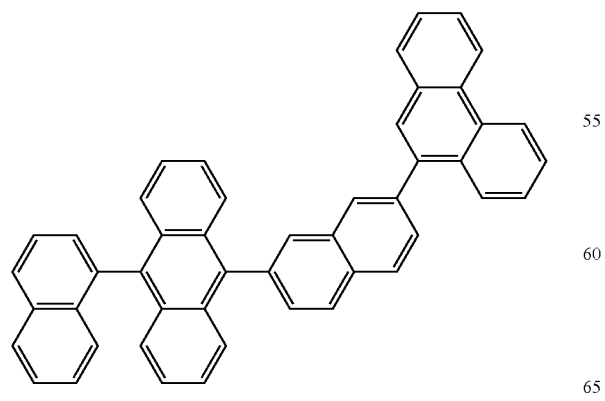
H21
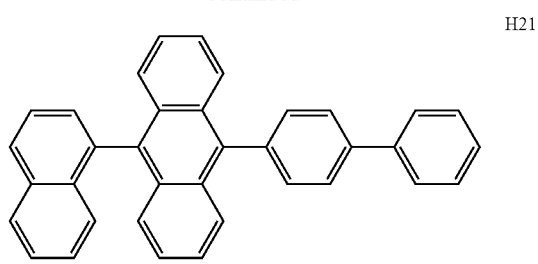
H22
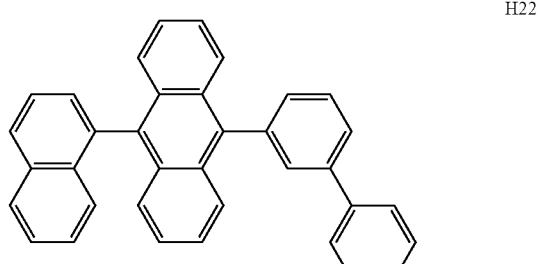
H23
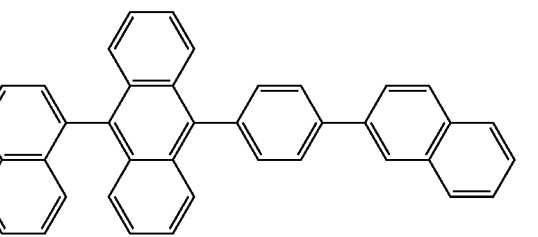
H24
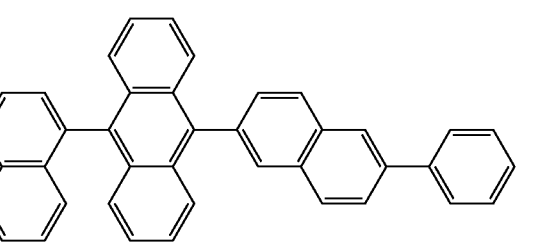
H25
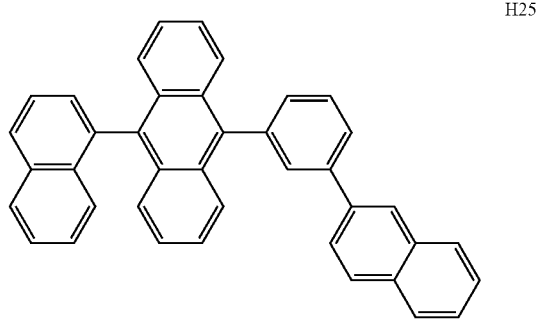

-continued
H26
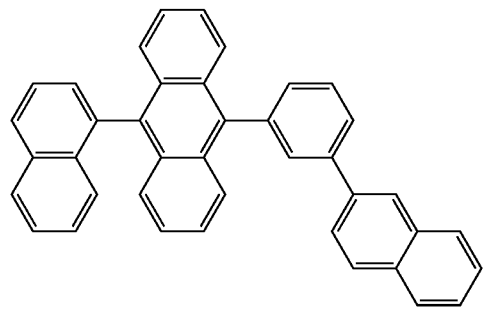
H27
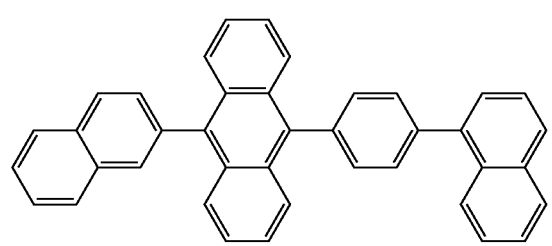
H28
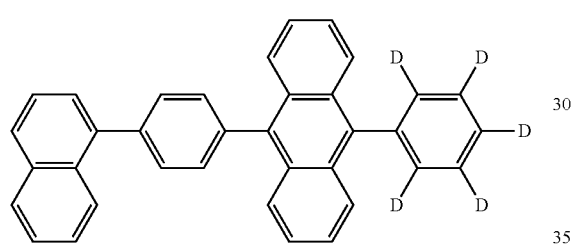
H29
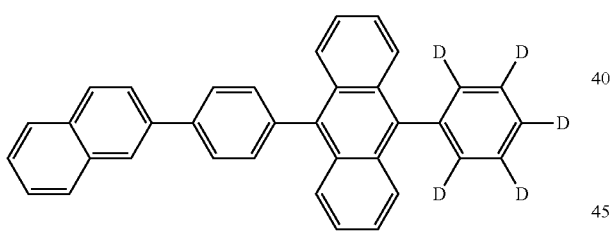
H30
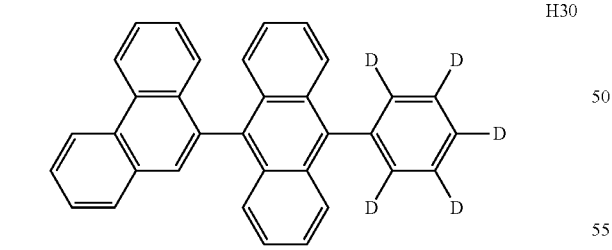
H31
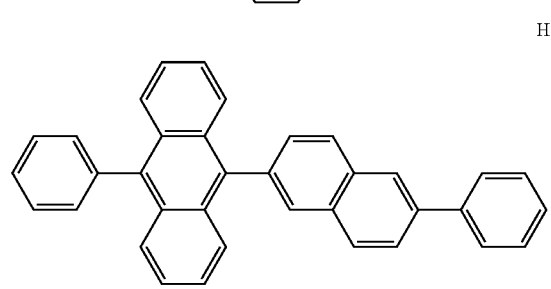
-continued
H32
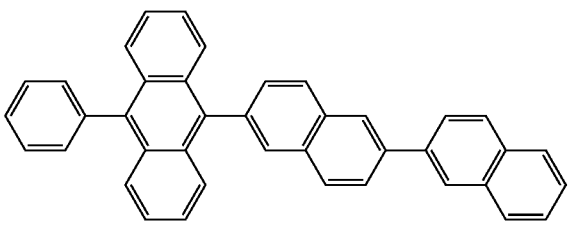
H33
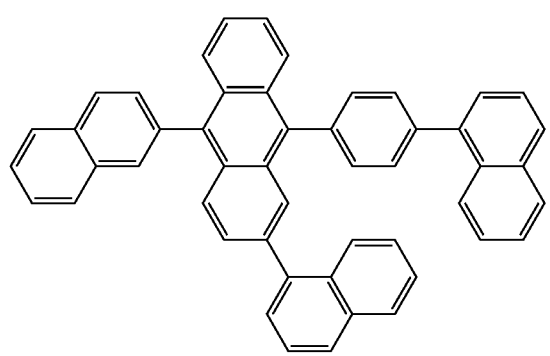
H34
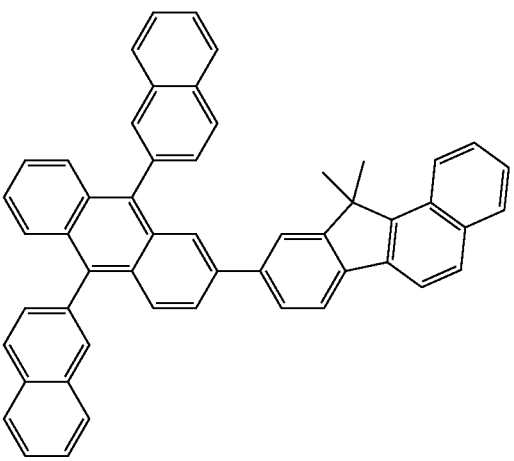
H35
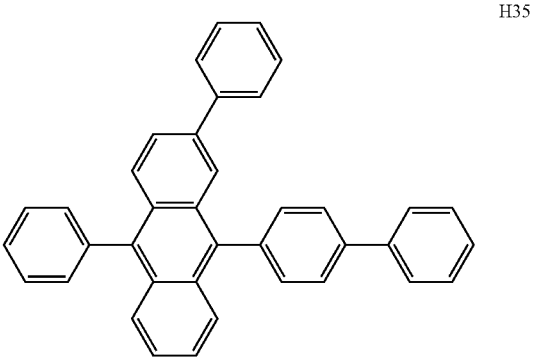

85
-continued
H36
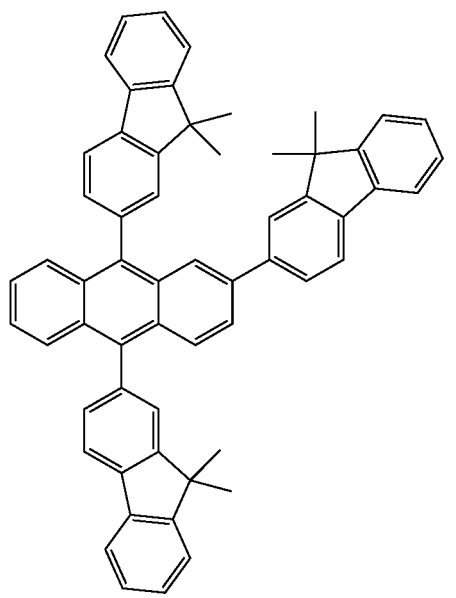
H37
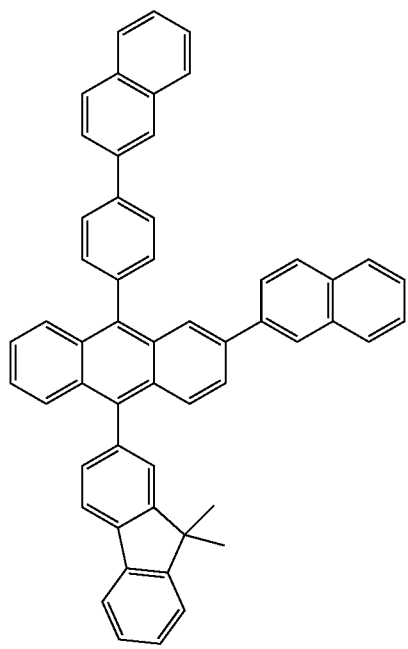
H38
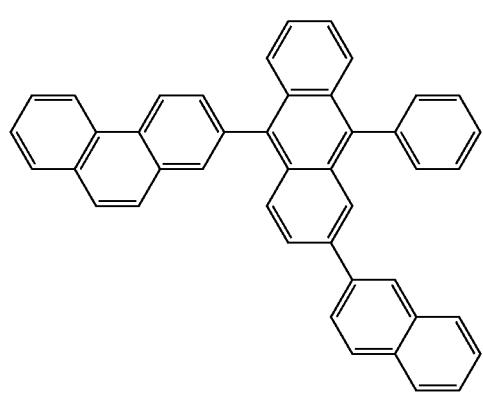
86
-continued
H39
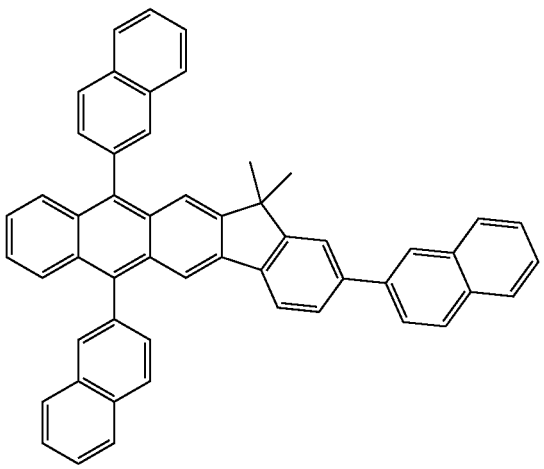
H40
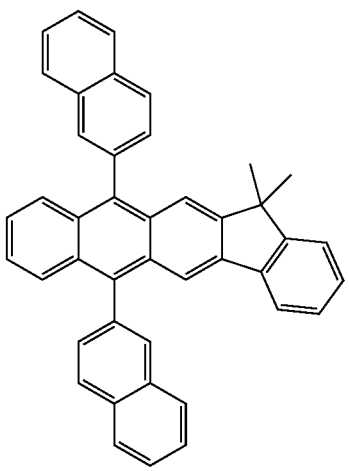
H41
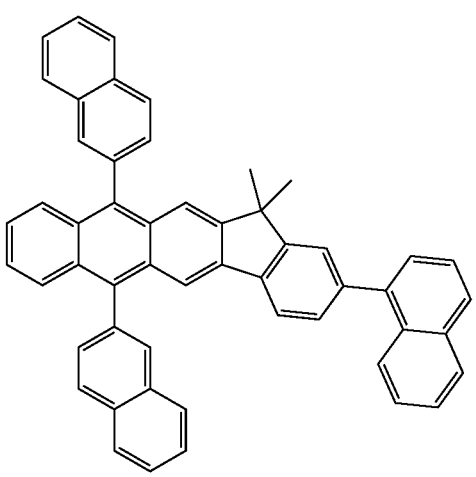

H42
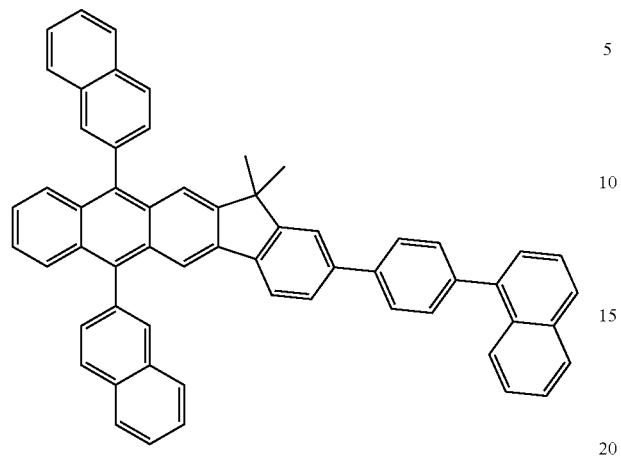
According to another embodiment of the present invention, the host may include at least one selected from Compounds H43 to H49 below, but are not limited thereto:
H43
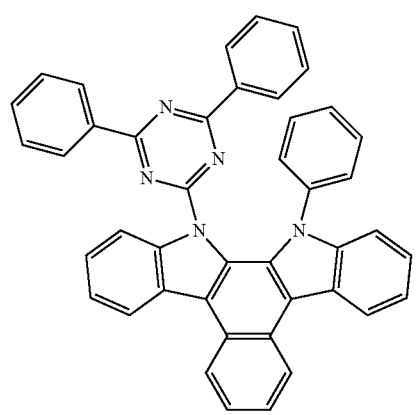
H44
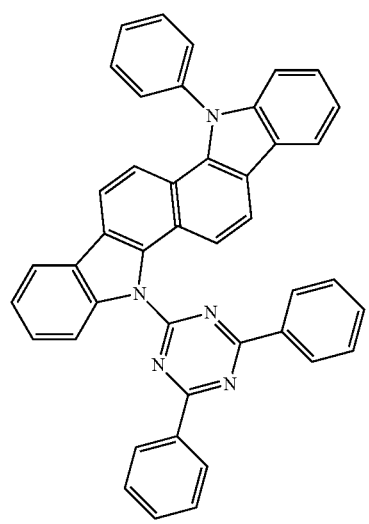
H45
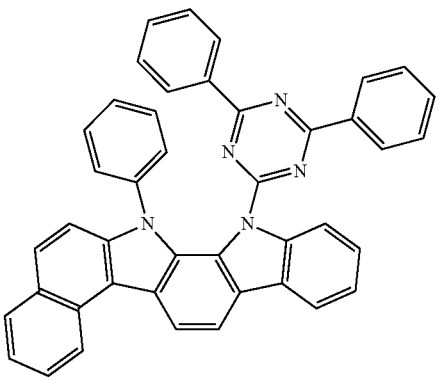
H46
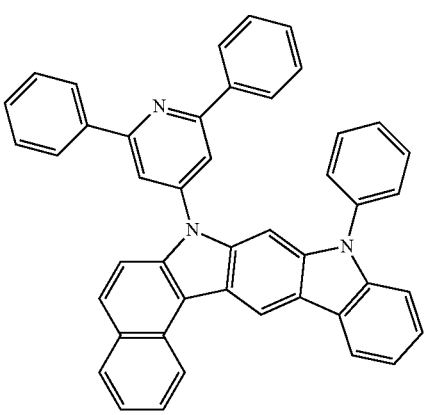
H47
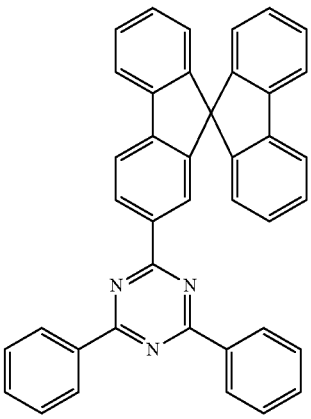
H48
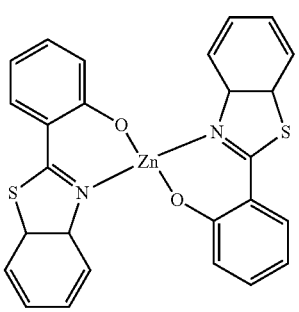

H49

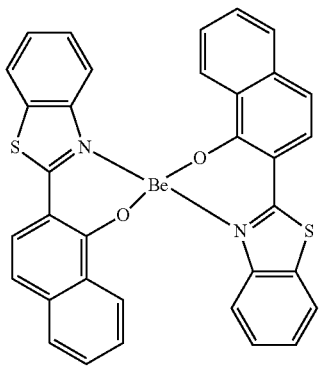

The dopant may be at least one selected from a fluorescent dopant and a phosphorescent dopant.

The phosphorescent dopant may include an organometallic complex represented by Formula 401 below:

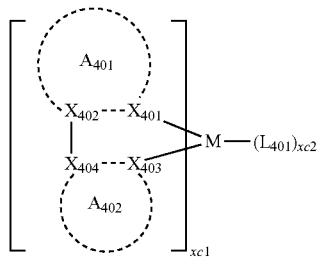

Formula 401 wherein in Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently a nitrogen atom or a carbon atom;

$A_{401}$ and $A_{402}$ rings may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrol, a substituted or unsubstituted thiopene, a substituted or unsubstituted furan, a substituted or unsubstituted imidazole, a substituted or unsubstituted pyrrazole, a substituted or unsubstituted thiazole, a substituted or unsubstituted isothiazole, a substituted or unsubstituted oxazole, a substituted or unsubstituted isooxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline a substituted or unsubstituted carbazolyl, a substituted or unsubstituted benzoimidazole, a substituted or unsubstituted benzofuran, a substituted or unsubstituted benzothiopene, a substituted or unsubstituted isobenzothiopene, a substituted or unsubstituted benzooxazole, a substituted or unsubstituted isobenzooxazole, a substituted or unsubstituted triazole, a substituted or unsubstituted oxadiazole, a substituted or unsubstituted triazine, a substituted or unsubstituted dibenzofuran, and a substituted or unsubstituted dibenzothiopene;

at least one substituent for each of the substituted benzene, substituted naphthalene, substituted fluorene, substituted spiro-fluorene, substituted indene, substituted pyrrol, substituted thiopene, substituted furan, substituted imidazole, substituted pyrrazole, substituted thiazole, substituted isothiazole, substituted oxazole, substituted isooxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzoimidazole, substituted benzofuran, substituted benzothiopene, substituted isobenzothiopene, substituted benzooxazole, substituted isobenzooxazole, substituted triazole, substituted oxadiazole, substituted triazine, substituted dibenzofuran, and substituted dibenzothiopene may be selected from:

a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, and a $C_1$-$C_{60}$ alkoxy;

a $C_1$-$C_{60}$ alkyl, a $C_2$-$C_{60}$ alkenyl, a $C_2$-$C_{60}$ alkynyl, and a $C_1$-$C_{60}$ alkoxy, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_2$-$C_{60}$ heteroaryl, a non-aromatic condensed polycyclic, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_2$-$C_{60}$ heteroaryl, and a non-aromatic condensed polycyclic group;

a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_2$-$C_{60}$ heteroaryl and non-aromatic condensed polycyclic group, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_2$-$C_{60}$ heteroaryl, non-aromatic condensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$) and —B($Q_{426}$)($Q_{427}$);

$L_{401}$ is an organic ligand;

xc1 is 1, 2, or 3;

xc2 is 0, 1, 2, or 3.

$L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propandionate, 2,2,6,6-tetramethyl-3,5-heptandionate, or hexafluoroacetonate), a carboxylic acid ligand (for example, picolinate, dimethyl-3-pyrazolecarboxylate, or benzoate), a carbon mono-oxide ligand, an isonitrile ligand, a cyano ligand, and a phosphorous ligand (for example, phosphine and phosphite), but is not limited thereto.

When $A_{401}$ in Formula 401 has two or more substituents, the substituents of $A_{401}$ may bind to each other to form a saturated or unsaturated ring.

When $A_{401}$ in Formula 402 has two or more substituents, the substituents of $A_{402}$ may bind to each other to form a saturated or unsaturated ring.

When xc1 in Formula 401 is two or more, a plurality of ligands,

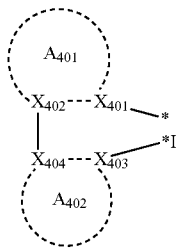

in Formula 401, may be identical or different. When xc1 in Formula 401 is two or more, $A_{401}$ and $A_{402}$ may be respectively directly connected to $A_{401}$ and $A_{402}$ of other neighboring ligands with or without a linker (for example, a $C_1$-$C_5$ alkylene group, or —N(R')— (wherein R' may be a $C_1$-$C_{10}$ alkyl group or a $C_6$-$C_{20}$ aryl group), or —C(=O)—) therebetween.

The phosphorescent dopant may include at least one selected from Compounds PD1 to PD74 below, but is not limited thereto:

PD1
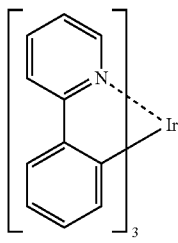

PD2
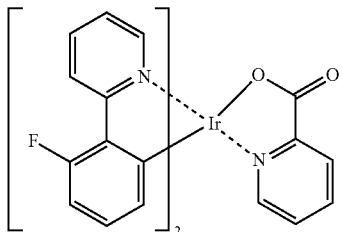

PD3
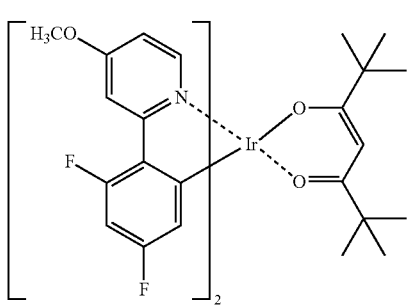

PD4
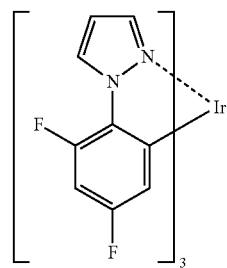

PD5
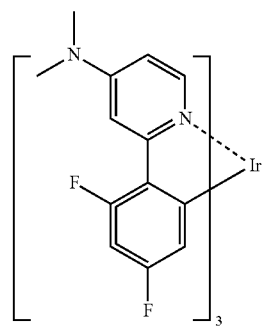

PD6
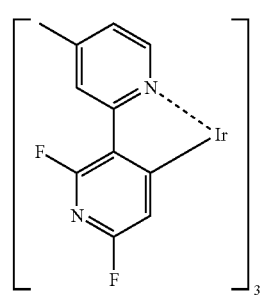

PD7
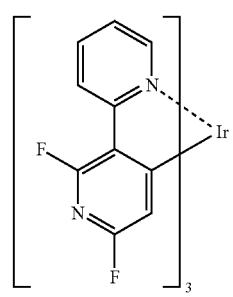

PD8
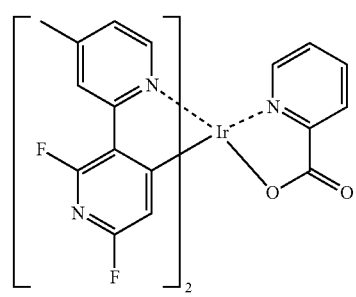

-continued
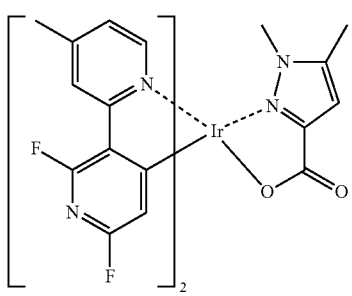
PD9
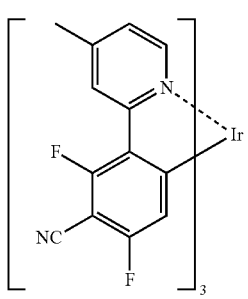
PD10
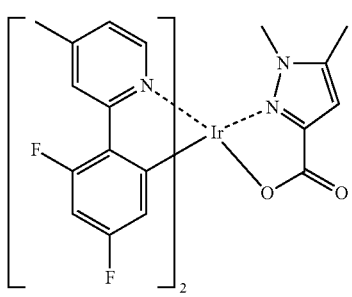
PD11
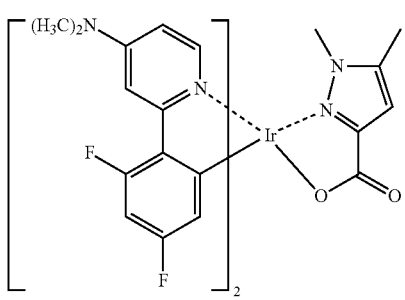
PD12
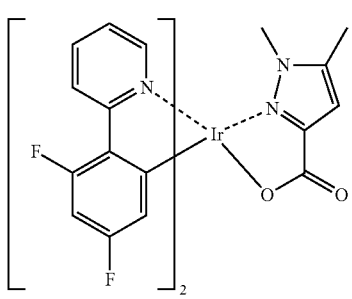
PD13
-continued
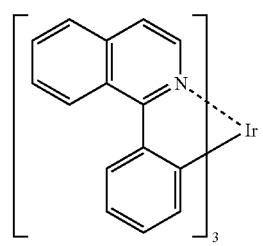
PD14
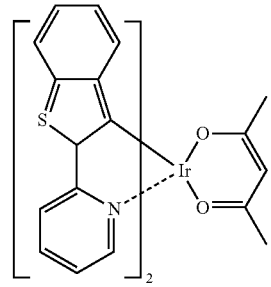
PD15
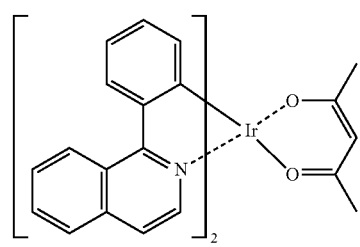
PD16
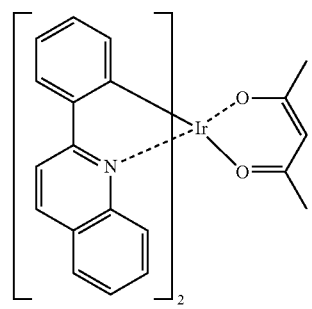
PD17
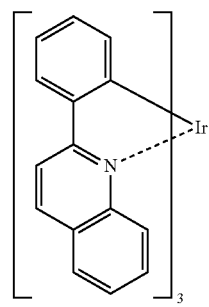
PD18

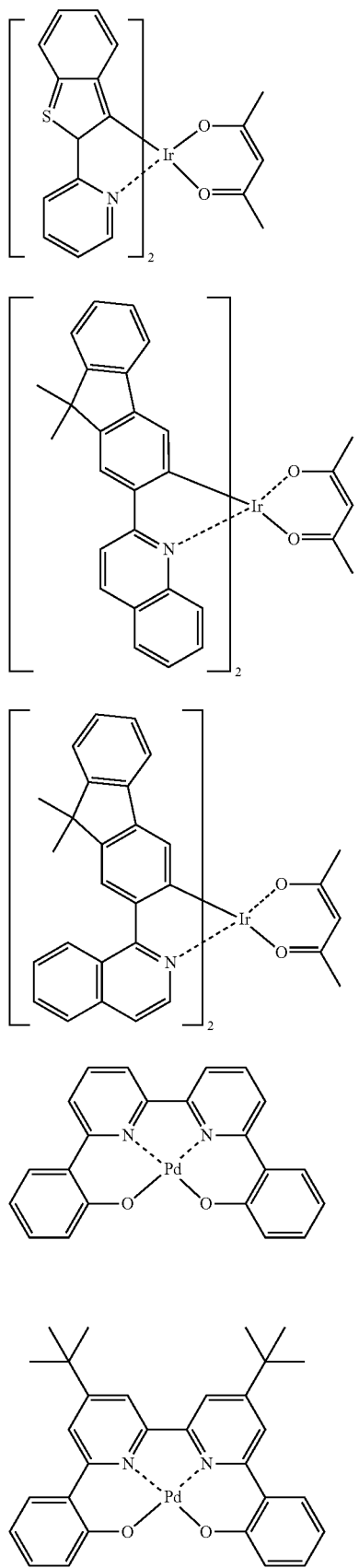
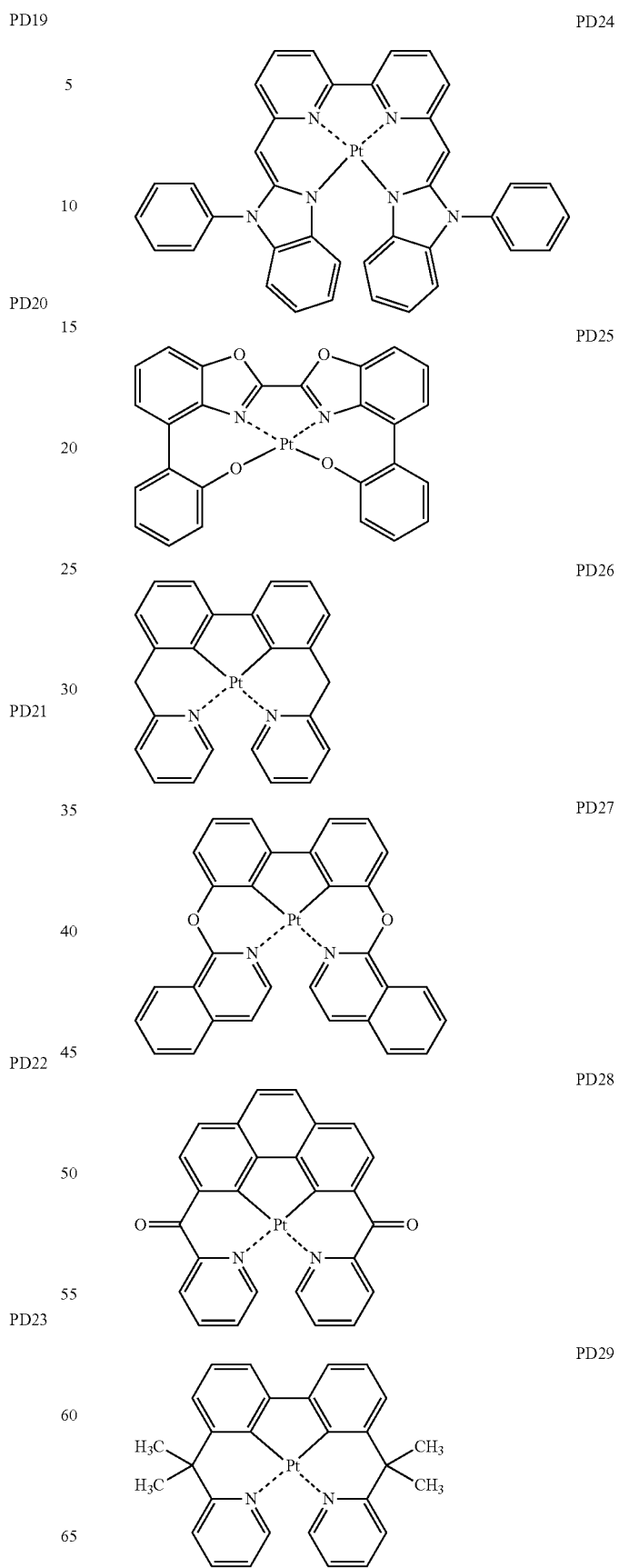

-continued
PD30
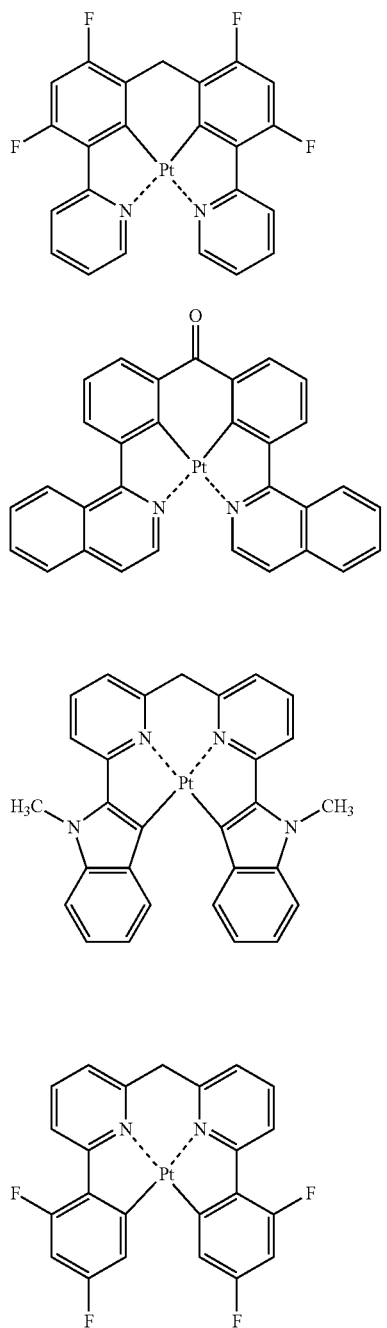
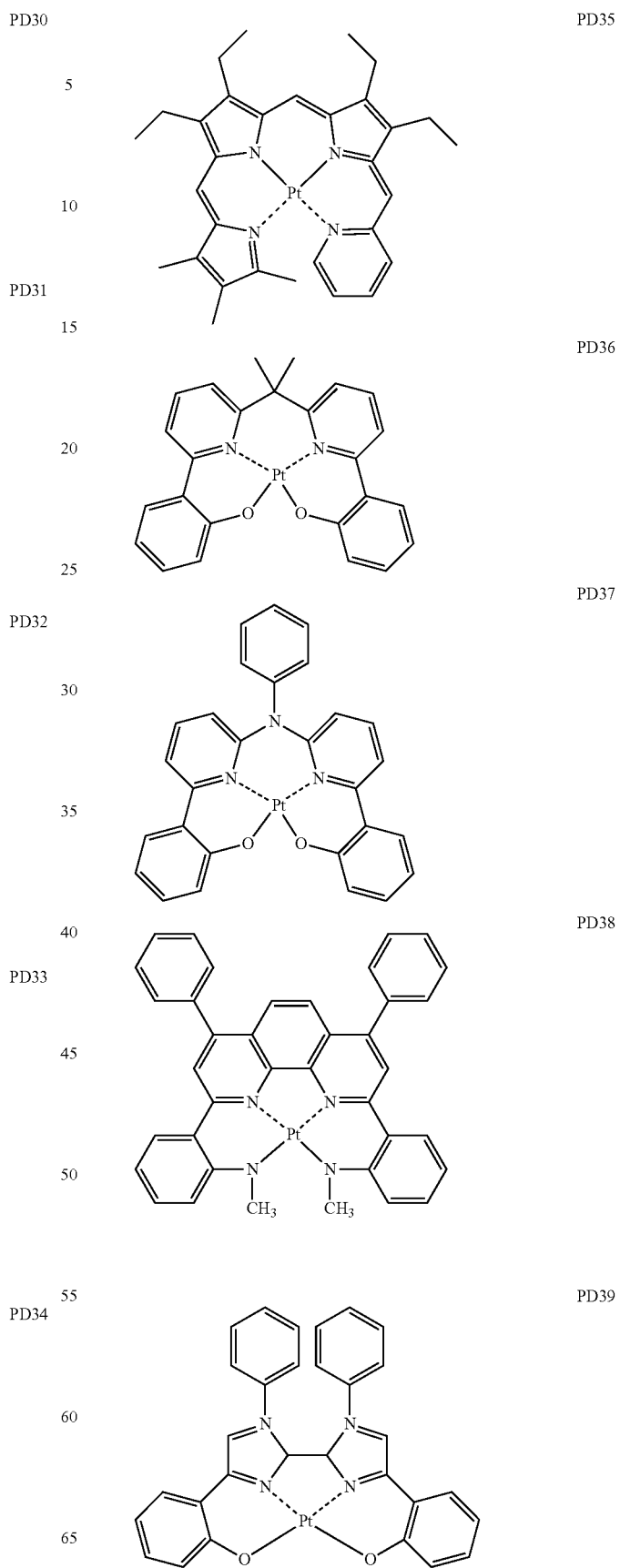

PD40
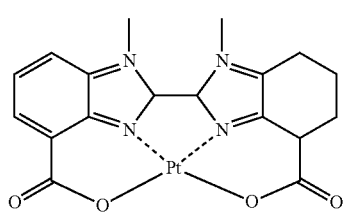
PD41
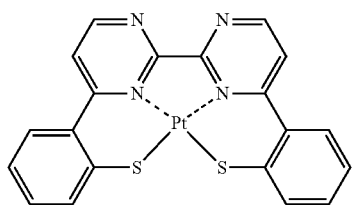
PD42
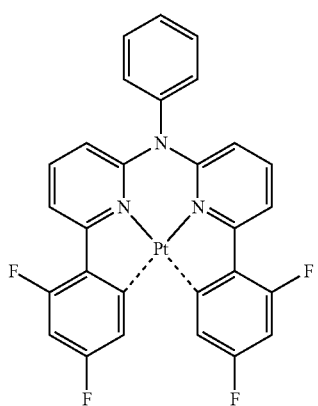
PD43
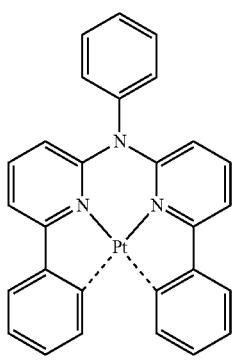
PD44
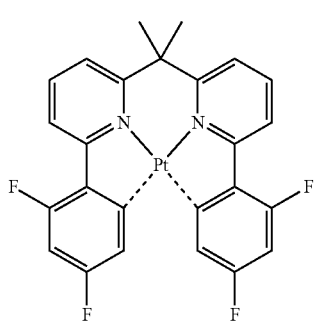
PD45
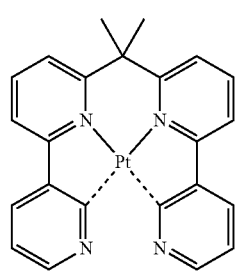
PD46
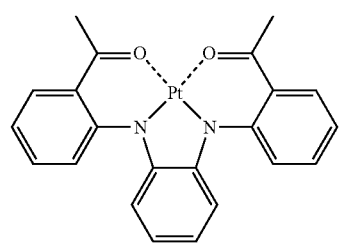
PD47
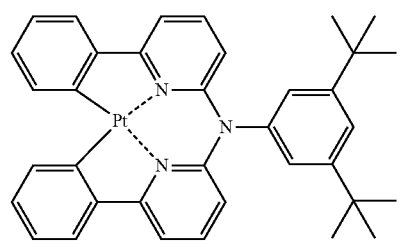
PD48
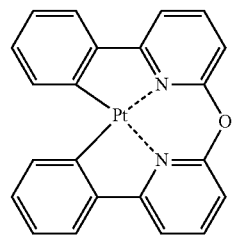
PD49
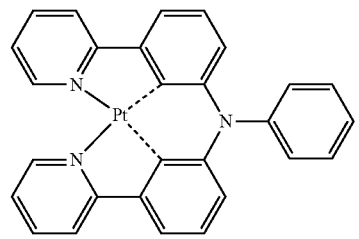
PD50
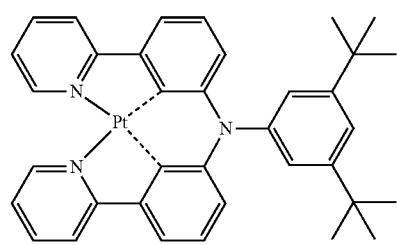

PD51 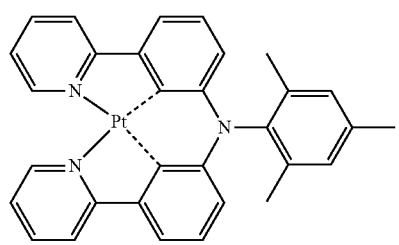
PD57 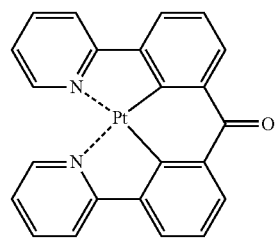
PD52 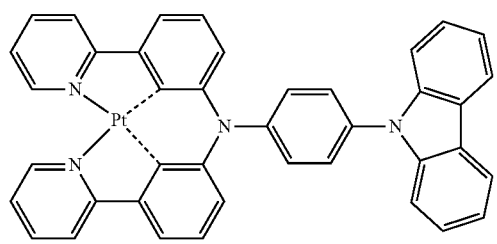
PD58 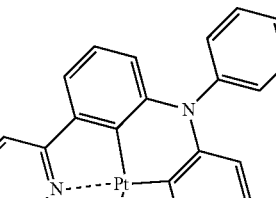
PD53 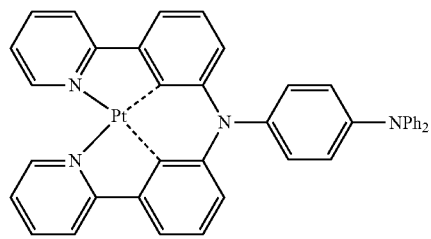
PD54 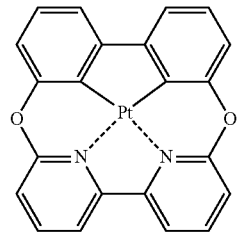
PD59 
PD55 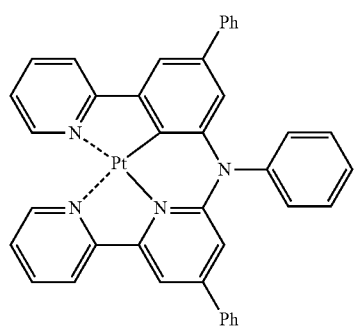
PD60 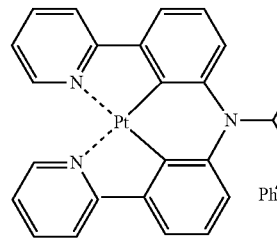
PD56 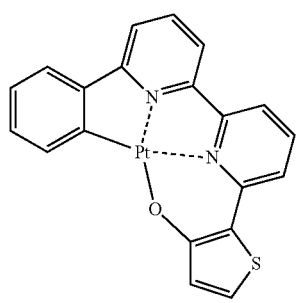
PD61 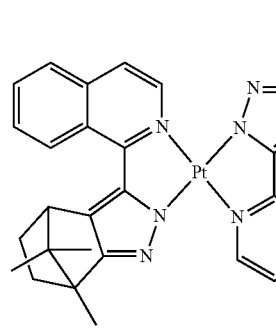

103
-continued
PD62
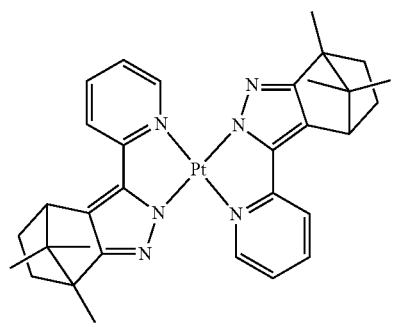
PD63
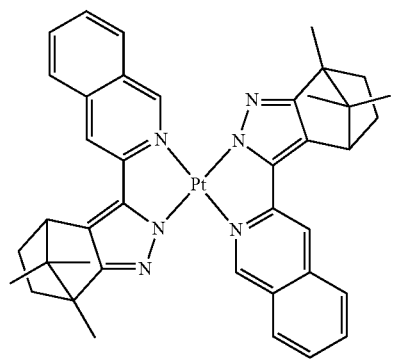
PD64
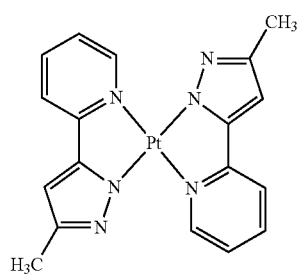
PD65
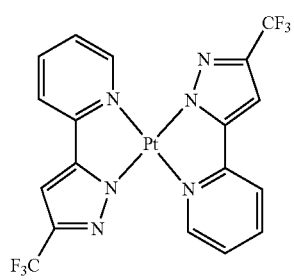
PD66
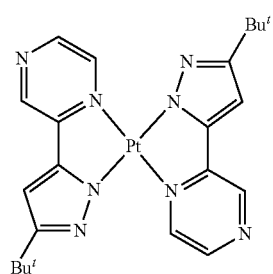
104
-continued
PD67
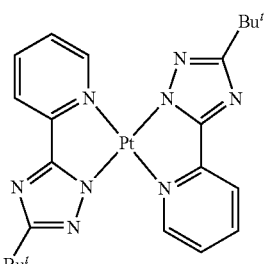
PD68
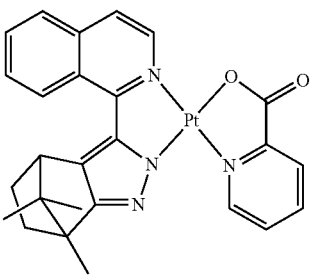
PD69
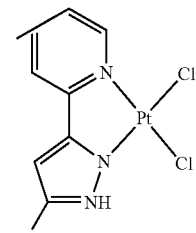
PD70
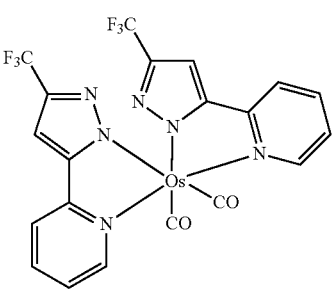
PD71
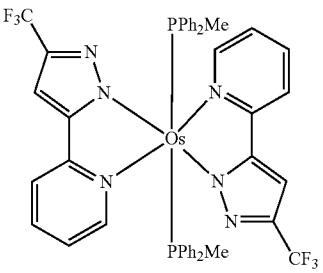

-continued
PD72 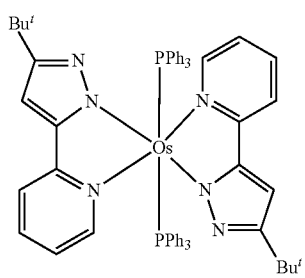
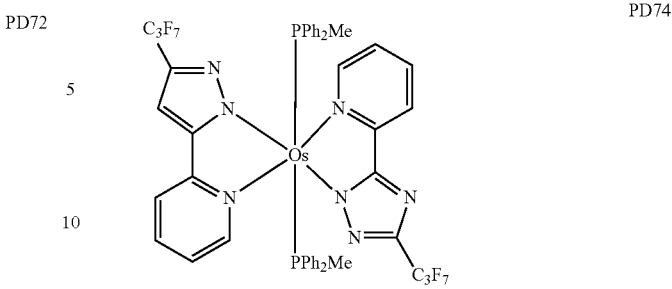
Alternatively, the phosphorescent dopant may include PtOEP:
PD73 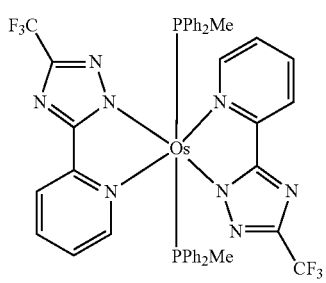
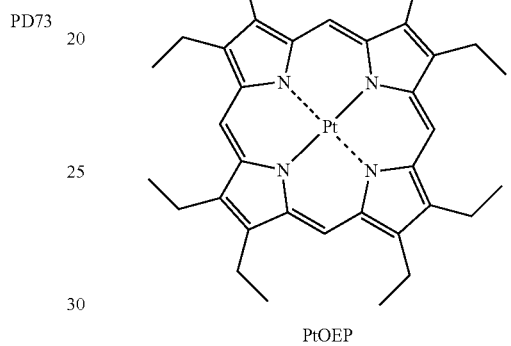
PtOEP
The fluorescent dopant may include at least one selected from DPAVBi, BDAVBi, TBPe, DCM, DCJTB, Coumarin 6, and C545T.
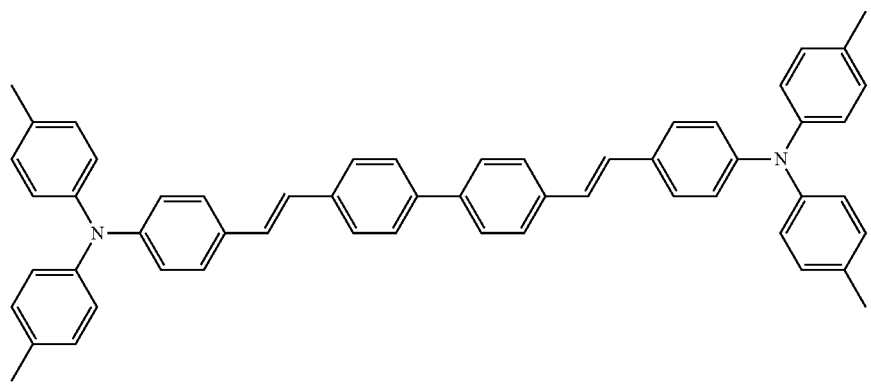
DPAVBi
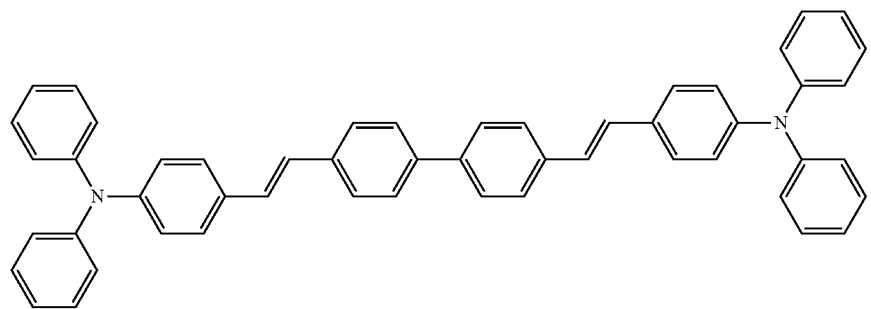
BDAVBi

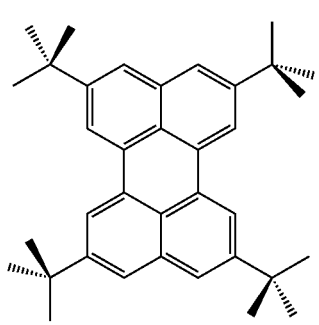
TBPe

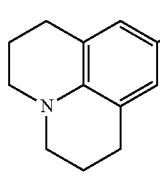
DCM

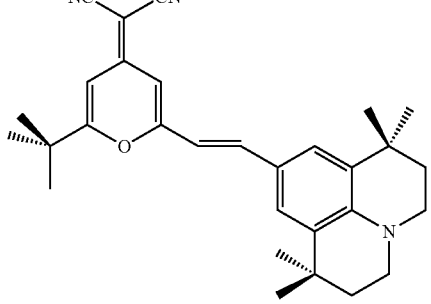
DCJTB

Coumarin 6

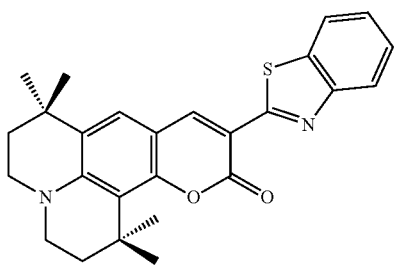
C545T

According to another embodiment of the present invention, the fluorescent dopant may include a compound represented by Formula 501 below.

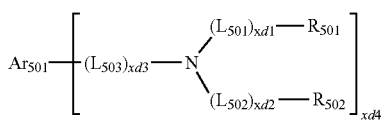

Formula 501 wherein in Formula 501, $Ar_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_2$-$C_{60}$ heteroaryl, non-aromatic condensed polycyclic group, and —Si($Q_{501}$)($Q_{502}$)($Q_{503}$) (wherein, $Q_{501}$ to $Q_{503}$ may be each independently a hydrogen, a $C_1$-$C_{60}$ alkyl, a $C_2$-$C_{60}$ alkenyl, a $C_6$-$C_{60}$ aryl, and a $C_2$-$C_{60}$ heteroaryl);

descriptions of $L_{501}$ to $L_{503}$ are the same as the description of $L_{201}$;

$R_{501}$ and $R_{502}$ are each independently selected from:

a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazole, a triazinyl, a dibenzofuranyl, and a dibenzothiophenyl; and a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, a triazinyl, a dibenzofuranyl, and a dibenzothiophenyl, each substituted with at least one selected from a deuterium, —F, —Cl, —Br, —I, a hydroxyl, a cyano, a nitro, an amino, an amidino, a hydrazine, a hydrazone, a carboxyl group and a salt thereof, a sulfonic acid group and a salt thereof, a phosphoric acid group and a salt thereof, a $C_1$-$C_{20}$ alkyl, a $C_1$-$C_{20}$ alkoxy, a phenyl, a naphthyl, a fluorenyl, a spiro-fluorenyl, a benzofluorenyl, a dibenzofluorenyl, a phenanthrenyl, an anthracenyl, a pyrenyl, a chrysenyl, a pyridinyl, a pyrazinyl, a pyrimidinyl, a pyridazinyl, a quinolinyl, an isoquinolinyl, a quinoxalinyl, a quinazolinyl, a carbazolyl, a triazinyl, a dibenzofuranyl, and a dibenzothiophenyl;

xd1 to xd3 are each independently selected from 0, 1, 2, and 3; and xb4 is selected from 1, 2, 3, and 4.

The fluorescent host may include at least one selected from Compounds FD1 to FD8 below:

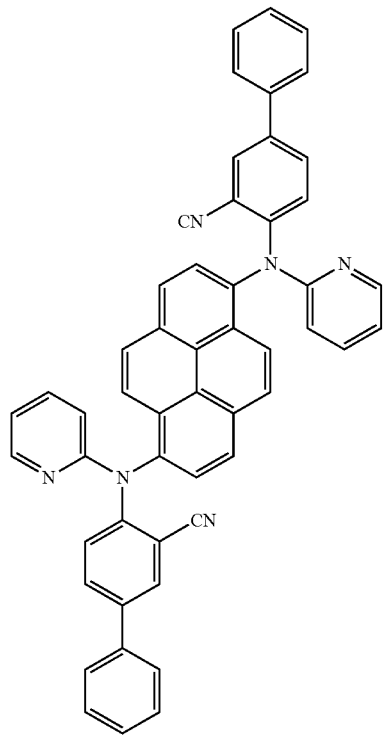

FD4

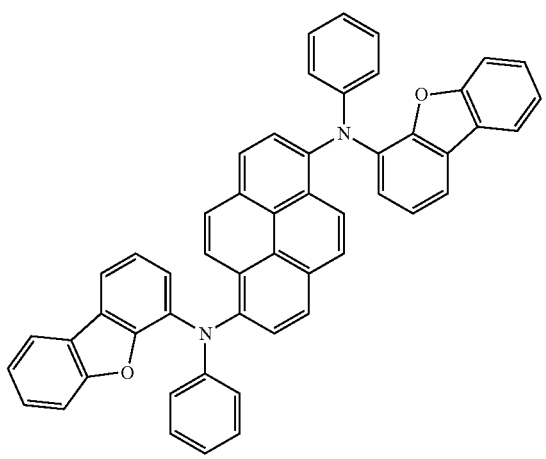

FD5

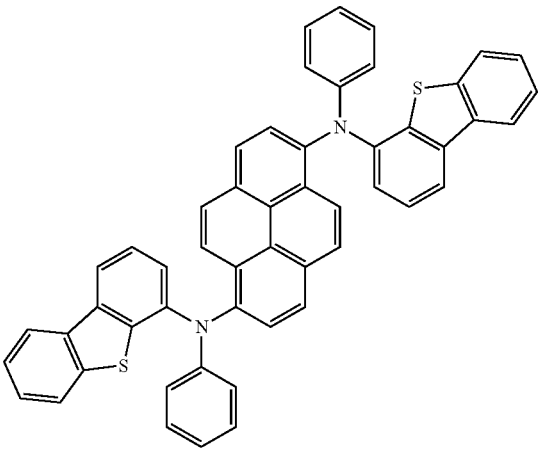

FD6

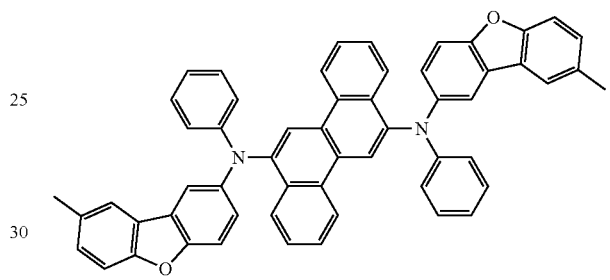

FD7

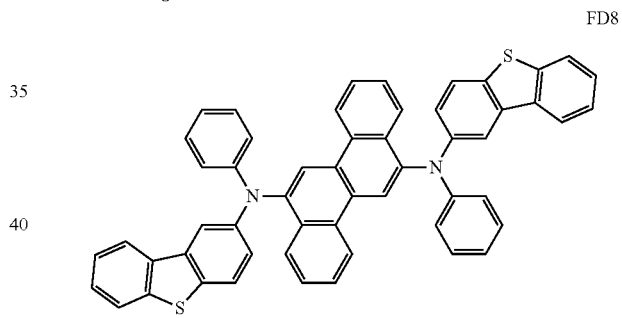

FD8

An amount of the dopant in the EML may be, in general, in a range of about 0.01 to about 15 parts by weight based on 100 parts by weight of the host, but is not limited thereto.

A thickness of the EML may be in a range of about 100 Å to about 1000 Å, for example, about 200 Å to about 600 Å. In one embodiment, when the thickness of the EML is within this range, excellent light-emission characteristics are obtained without a substantial increase in driving voltage.

Then, an electron transport region may be disposed on the EML.

The electron transport region may include at least one selected from an HBL, an ETL, and an EIL, but is not limited thereto.

For example, the electron transport region may have a structure of ETL/EIL or a structure of HBL/ETL/EIL, wherein layers of each structure are sequentially stacked from the EML in the stated order, but is not limited thereto.

According to an embodiment of the present invention, the organic layer 150 of the organic light-emitting device includes an electron transport region disposed between the EML and the second electrode 190, wherein the electron transport region includes the triazine-based compound represented by Formula 1.

The electron transport region may include an HBL. When the EML includes a phosphorescent dopant, the HBL may be formed to prevent diffusion of excitons or holes into an ETL.

When the electron transport region includes an HBL, the HBL may be formed on the EML by using (utilizing) various suitable methods, such as vacuum deposition, spin coating, casting, an LB method, ink-jet printing, laser-printing, or laser-induced thermal imaging. When the HBL is formed by vacuum deposition or spin coating, deposition and coating conditions for the HBL may be determined by referring to the deposition and coating conditions for the HIL.

The HBL may include, for example, at least one selected from BCP and Bphen, but is not limited thereto.

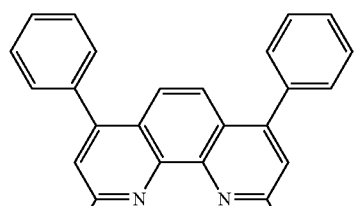

BCP

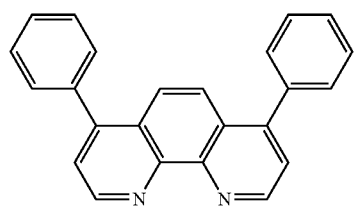

Bphen

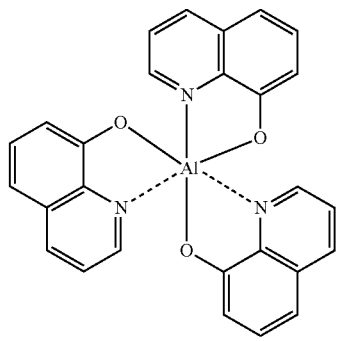

Alq$_3$

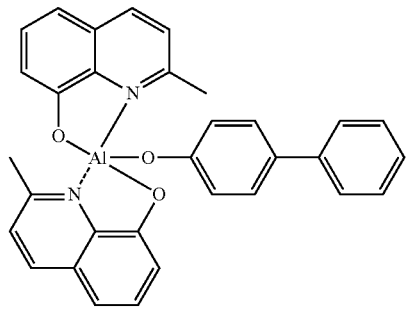

BAlq

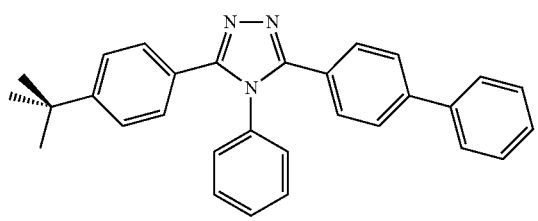

TAZ

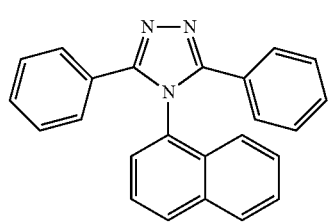

NTAZ

A thickness of the HBL may be in a range of about 20 Å to about 1000 Å, for example, about 30 Å to about 300 Å. In one embodiment, when the thickness of the HBL is within these ranges, the HBL has excellent hole blocking characteristics without a substantial increase in driving voltage.

The electron transport region may include an ETL. The ETL may be formed on the EML or the HBL by using (utilizing) various suitable methods, such as vacuum deposition, spin coating casting, an LB method, ink-jet printing, laser-printing, or laser-induced thermal imaging. When an ETL is formed by vacuum deposition or spin coating, deposition and coating conditions for the ETL may be determined by referring to the deposition and coating conditions for the HIL.

According to an embodiment of the present invention, the organic layer 150 of the organic light-emitting device includes an electron transport region disposed between the EML and the second electrode 190, wherein the electron transport region includes an ETL, and the ETL includes the triazine-based compound represented by Formula 1.

The ETL may further include, in addition to the triazine-based compound represented by Formula 1, at least one selected from BCP and Bphen described above, and Alq$_3$, Balq, TAZ, and NTAZ, which are illustrated below.

A thickness of the ETL may be in a range of about 100 Å to about 1000 Å, for example, about 150 Å to about 500 Å. In one embodiment, when the thickness of the ETL is within the range described above, the ETL has satisfactory electron transportation characteristics without a substantial increase in driving voltage.

Also, the ETL may further include, in addition to the materials described above, a metal-containing material.

The metal-containing material may include a Li complex. The Li complex may include, for example, Compound ET-D1 (lithium quinolate, LiQ) or ET-D2.

ET-D1

ET-D2

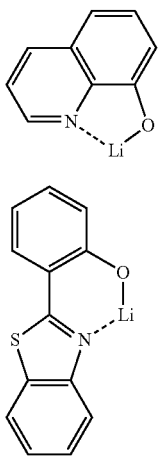

The electron transport region may include an EIL that allows electrons to be easily provided from the second electrode 190.

The EIL may be formed on the ETL by using (utilizing) various suitable methods, such as vacuum deposition, spin coating, casting, an LB method, ink-jet printing, laser-printing, or laser-induced thermal imaging. When an EIL is formed by vacuum deposition or spin coating, deposition and coating conditions for the EIL may be determined by referring to the deposition and coating conditions for the HIL.

The EIL may include at least one selected from, LiF, NaCl, CsF, $Li_2O$, BaO, and LiQ.

A thickness of the EIL may be in a range of about 1 Å to about 100 Å, for example, about 3 Å to about 90 Å. In one embodiment, when the thickness of the EIL is within the range described above, the EIL has satisfactory electron transportation characteristics without a substantial increase in driving voltage.

The second electrode 190 is disposed on the organic layer 150 having the structure described above. The second electrode 190 may be a cathode that is an electron injection electrode, and in this regard, a material for forming the second electrode 190 may be a material having a low work function, and such a material may be a metal, an alloy, an electrically conductive compound, or a mixture thereof. Detailed examples of the second electrode 190 are lithium (Li), magnesium (Mg), aluminum (Al), aluminum-lithium (Al—Li), calcium (Ca), magnesium-indium (Mg—In), or magnesium-silver (Mg—Ag). According to another embodiment of the present invention, the material for forming the second electrode 190 may be ITO or IZO. The second electrode 190 may be a reflective electrode, a semi-transmissive electrode, or a transmissive electrode.

Hereinbefore, the organic light-emitting device has been described with reference to the drawing, but is not limited thereto.

A "$C_1$-$C_{60}$ alkyl" as used herein refers to a linear or branched aliphatic hydrocarbon monovalent group having 1 to 60 carbon atoms, and detailed examples thereof are a methyl, an ethyl, a propyl, an isobutyl, a sec-butyl, a tert-butyl, a pentyl, an iso-amyl, and a hexyl. A "$C_1$-$C_{60}$ alkylene" used herein refers to a divalent group having the same structure as the $C_1$-$C_{60}$ alkyl group.

A "$C_1$-$C_{60}$ alkoxy" as used herein refers to a monovalent group represented by —$OA_{101}$ (wherein $A_{101}$ is the $C_1$-$C_{60}$ alkyl group), and detailed examples thereof are a methoxy, an ethoxy, and an isopropyloxy.

A "$C_2$-$C_{60}$ alkenyl" as used herein refers to a hydrocarbon group having at least one carbon double bond in the middle or terminal of the $C_2$-$C_{60}$ alkyl group, and detailed examples thereof are an ethenyl group, a prophenyl group, and a butenyl group. A "$C_2$-$C_{60}$ alkenylene" as used herein refers to a divalent group having the same structure as the $C_2$-$C_{60}$ alkenyl group.

A "$C_2$-$C_{60}$ alkynyl" as used herein refers to a hydrocarbon group having at least one carbon triple bond in the middle or terminal of the $C_2$-$C_{60}$ alkyl group, and detailed examples thereof are an ethynyl group and a propynyl group. A "$C_2$-$C_{60}$ alkynylene (group)" herein refers to a divalent group having the same structure as the $C_2$-$C_{60}$ alkynyl group.

A "$C_3$-$C_{10}$ cycloalkyl" as used herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group. A "$C_3$-$C_{10}$ cycloalkylene (group)" used herein refers to a divalent group having the same structure as the $C_3$-$C_{10}$ cycloalkyl group.

A "$C_3$-$C_{10}$ heterocycloalkyl" as used herein refers to a monovalent monocyclic group having at least one heteroatom selected from N, O, P, and S as a ring-forming atom and 3 to 10 carbon atoms, and detailed examples thereof are tetrahydrofuranyl and tetrahydrothiophenyl. A "$C_2$-$C_{10}$ heterocycloalkylene (group)" used herein refers to a divalent group having the same structure as the $C_3$-$C_{10}$ heterocycloalkyl group.

A "$C_3$-$C_{10}$ cycloalkenyl" as used herein refers to a monovalent monocyclic group that has 3 to 10 carbon atoms and at least one double bond in the ring thereof and does not have aromacity, and detailed examples thereof are a cyclopentenyl group, a cyclohexenyl group, and a cycloheptenyl group. A "$C_3$-$C_{10}$ cycloalkenylene (group)" used herein refers to a divalent group having the same structure as the $C_3$-$C_{10}$ cycloalkenyl group.

A "$C_3$-$C_{10}$ heterocycloalkenyl" as used herein refers to a monovalent monocyclic group that has at least one heteroatom selected from N, O, P, and S as a ring-forming atom, 3 to 10 carbon atoms, and at least one double bond in its ring. Detailed examples of the $C_3$-$C_{10}$ heterocycloalkenyl group are a 2,3-hydrofuranyl group and a 2,3-hydrothiophenyl group. A "$C_3$-$C_{10}$ heterocycloalkenylene (group)" used herein refers to a divalent group having the same structure as the $C_3$-$C_{10}$ heterocycloalkenyl group.

A "$C_6$-$C_{60}$ aryl" as used herein refers to a monovalent group having a carbocyclic aromatic system having 6 to 60 carbon atoms, and a "$C_6$-$C_{60}$ arylene (group)" used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A "$C_2$-$C_{60}$ heteroaryl" as used herein refers to a monovalent group having a carbocyclic aromatic system that has at least one heteroatom selected from N, O, P, and S as a ring-forming atom, and 2 to 60 carbon atoms. A "$C_2$-$C_{60}$ heteroarylene (group)" used herein refers to a divalent group having a carbocyclic aromatic system that has at least one heteroatom selected from N, O, P, and S as a ring-forming atom, and 2 to 60 carbon atoms. Detailed examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

A "$C_6$-$C_{60}$ aryloxy (group)" used herein is represented by —$OA_{102}$ (wherein $A_{102}$ is the $C_6$-$C_{60}$ aryl), and a "$C_6$-$C_{60}$ arylthio (group)" used herein is represented by —$SA_{103}$ (wherein $A_{103}$ is the $C_6$-$C_{60}$ aryl group).

A "monovalent non-aromatic condensed polycyclic group" as used herein refers to a monovalent group that has two or more rings condensed to each other, only carbon atoms as a ring-forming atom, and non-aromacity in the entire molecular structure. A detailed example of the monovalent non-aromatic condensed polycyclic group is a fluorenyl group. A "divalent non-aromatic condensed polycyclic group" as used herein refers to a divalent group having the same structure as the monovalent non-aromatic condensed polycyclic group.

A "monovalent non-aromatic hetero-condensed polycyclic group" as used herein refers to a monovalent group that has two or more rings condensed with each other, has a heteroatom selected from N, O P, and S as a ring forming atom other than carbon atoms, and has non-aromacity in the entire molecular structure. Detailed examples of the monovalent non-aromatic condensed heteropolycyclic group are a carbazolyl group. A "divalent non-aromatic condensed heteropolycyclic group" as used herein refers to a divalent group having the same structure as the monovalent non-aromatic hetero-condensed polycyclic group.

The term "Ph" used herein refers to a phenyl group, the term "Me" used herein refers to a methyl group, the term "Et" used herein refers to an ethyl group, and the term "tert-Bu" or "Bu$^t$" used herein refers to a tert-butyl group.

Hereinafter, an organic light-emitting device according to an embodiment of the present invention will be described in more detail with reference to Synthesis Examples and Examples. The wording "B was used (utilized) instead of A" used in describing Synthesis Examples means that a molar equivalent of A was identical to a molar equivalent of B.

EXAMPLE

Synthesis Example 1

Synthesis of Compound 1

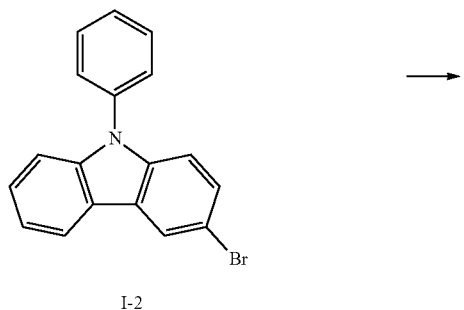

I-2

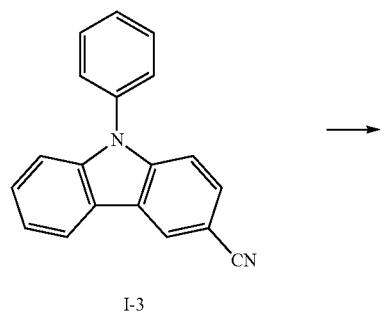

I-3

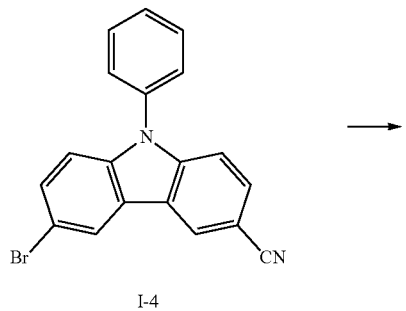

I-4

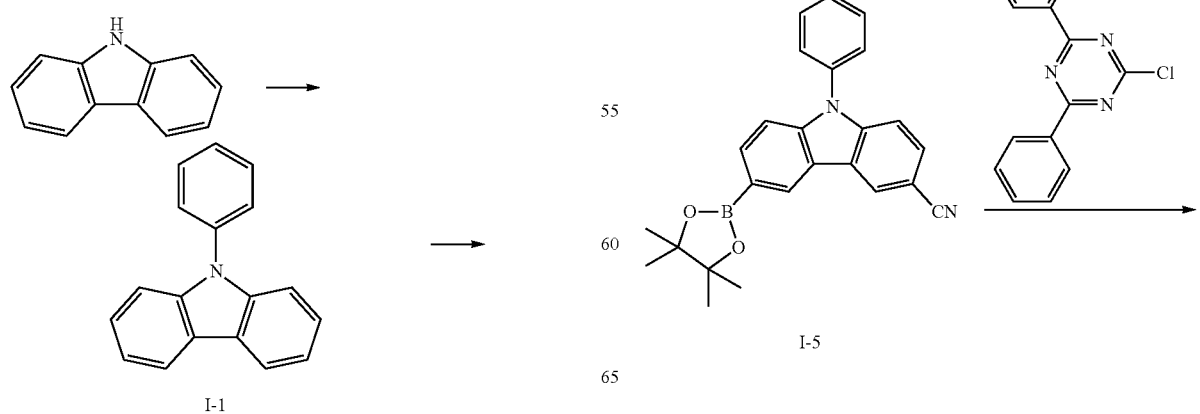

I-1

I-5

-continued

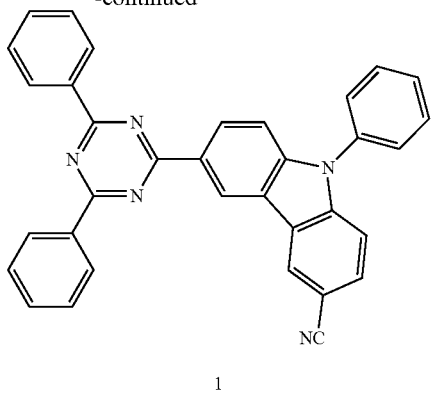

1

1) Synthesis of Intermediate I-1

5.02 g (30 mmol) of 9H-carbazole, 4.71 g (30 mmol) of bromobenzene, 1.14 g (18 mmol) of copper powder, and 6.22 g (45 mmol) of $K_2CO_3$ were dissolved in 80 mL of o-dichlorobenzene and then stirred at a temperature of 180° C. for 24 hours to prepare a reaction solution. The reaction solution was cooled to room temperature, 60 mL of water was added thereto, and then extracted three times with 50 mL of ethylacetate to collect organic layers. The collected organic layers were dried with magnesium sulfate and a solvent was evaporated therefrom to obtain residues, which were separated and purified by using (utilizing) silica gel column chromatography to obtain 5.47 g (yield 75%) of Intermediate I-1. The compound obtained therefrom was analyzed through LC-MS. $C_{18}H_{13}N$: $M^+$ 243.10.

2) Synthesis of Intermediate I-2

4.00 g (22.5 mmol) of N-bromosuccinimide was added to a solution in which 5.47 g (22.5 mmol) of Intermediate I-1 was completely dissolved in 80 mL of $CH_2Cl_2$ and then stirred at room temperature for 12 hours to prepare a reaction solution. 60 mL of water was added to the reaction solution and then extracted three times with 50 mL of $CH_2Cl_2$ to collect organic layers. The collected organic layers were dried with magnesium sulfate, a solvent was evaporated therefrom and then recrystallized with methanol to obtain 6.16 g (yield 85%) of Intermediate I-2. The compound obtained therefrom was analyzed through LC-MS. $C_{18}H_{12}BrN$: $M^+$ 321.0.

3) Synthesis of Intermediate I-3

6.16 g (19.1 mmol) of Intermediate I-2 and 2.57 g (281 mmol) of CuCN were dissolved in DMF 70 mL and then stirred at 150° C. for 24 hours to prepare a reaction solution. The reaction solution was cooled to room temperature and then 60 mL of ammonia water and 60 mL of water were added thereto and then extracted three times with 50 mL of $CH_2Cl_2$ to collect organic layers. The collected organic layers were dried with magnesium sulfate and a solvent was evaporated therefrom to obtain residues, which were separated and purified by using (utilizing) silica gel column chromatography to obtain 4.71 g (yield 92%) of Intermediate I-3. The compound obtained therefrom was analyzed through LC-MS. $C_{19}H_{12}N_2$: $M^+$ 268.1.

4) Synthesis of Intermediate I-4

3.13 g (17.6 mmol) of N-bromosuccinimide was added to a solution in which 4.71 g (17.6 mmol) of Intermediate I-3 was completely dissolved in 80 mL of $CH_2Cl_2$ and then stirred at room temperature for 8 hours to prepare a reaction solution. 60 mL of water was added to the reaction solution and then extracted three times with 50 mL of $CH_2Cl_2$ to collect organic layers. The collected organic layers were dried with magnesium sulfate, a solvent was evaporated therefrom, and then recrystallized by using (utilizing) methanol to obtain 5.81 g (yield 95%) of Intermediate I-4. The compound obtained therefrom was analyzed through LC-MS. $C_{19}H_{11}BrN_2$: $M^+$ 346.0.

5) Synthesis of Intermediate I-5

5.81 g (16.7 mmol) of Intermediate I-4, 0.68 g (0.84 mmol) of 0.68 g (0.84 mmol) of $Pd(dppf)_2Cl_2$, and 4.92 g (50.1 mmol) of KOAc were dissolved in 80 mL of DMSO and then stirred at 150° C. for 24 hours to prepare a reaction solution. The reaction solution was cooled to room temperature, 100 mL of water was added thereto and then extracted three times with 50 mL of $CH_2Cl_2$ to collect organic layers. The collected organic layers were dried with magnesium sulfate and a solvent was evaporated therefrom to obtain residues, which were separated and purified by using (utilizing) silica gel column chromatography to obtain 4.61 g (yield 70%) of Intermediate I-5. The compound obtained therefrom was analyzed through LC-MS. $C_{33}H_{19}BrN_2$: $M^+$ 522.1.

6) Synthesis of Compound 1

4.61 g (11.7 mmol) of Intermediate I-5, 3.13 g (11.7 mmol) of 2-chloro-4,6-diphenyl-1,3,5-triazine, 0.68 g (0.585 mmol) of $Pd(PPh_3)_4$, and 4.85 g (35.1 mmol) of $K_2CO_3$ were dissolved in 60 mL of THF and 30 mL of $H_2O$ and then stirred at a temperature of 80° C. for 12 hours to prepare a reaction solution. The reaction solution was cooled to room temperature and then extracted three times with 30 mL of water and 30 mL of ethylacetate to collect organic layers. The collected organic layers were dried with magnesium sulfate, a solvent was evaporated therefrom to obtain residues, which were separated and purified by using (utilizing) silica gel column chromatography to obtain 4.09 g (yield 70%) of Compound 1. The compound obtained therefrom was analyzed through MS/FAB and $^1H$ NMR. $C_{34}H_{21}N_5$ cal. 499.18, found 499.17.

Synthesis Example 2

Synthesis of Compound 3

4.63 g (yield 72%) of Compound 3 was synthesized in the same manner as in the synthesis of Compound 1, except that 2-bromo-naphthalene was used (utilized) instead of bromobenzene in the synthesis of Intermediate I-1. The compound obtained therefrom was analyzed through MS/FAB and $^1H$ NMR. $C_{38}H_{23}N_5$ cal. 549.20, found 549.21.

Synthesis Example 3

Synthesis of Compound 13

4.56 g (yield 65%) of Compound 13 was synthesized in the same manner as in the synthesis of Compound 1, except that 2-chloro-4,6-di-(naphthalene-1-yl)-1,3,5-triazine was used (utilized) instead of 2-chloro-4,6-diphenyl-1,3,5-triazine in the synthesis of Compound 1. The compound obtained therefrom was analyzed through MS/FAB and $^1H$ NMR. $C_{42}H_{25}N_5$ cal. 599.21, found 599.20.

Synthesis Example 4

Synthesis of Compound 20

4.72 g (yield 62%) of Compound 20 was synthesized in the same manner as in the synthesis of Compound 13, except that 2-bromoquinoline was used (utilized) instead of bromobenzene in the synthesis of Compound 13. The compound obtained therefrom was analyzed through MS/FAB and $^1$H NMR. $C_{45}H_{26}N_6$ cal. 650.22, found 650.21.

Synthesis Example 5

Synthesis of Compound 28

4.43 g (yield 63%) of Compound 28 was synthesized in the same manner as in the synthesis of Compound 1, except that 3-bromopyridine was used (utilized) instead of bromobenzene and 2-chloro-4,6-di-(naphthalene-2-yl)-1,3,5-triazine was used (utilized) instead of 2-chloro-4,6-diphenyl-1,3,5-triazine in the synthesis of Intermediate I-1. The compound obtained therefrom was analyzed through MS/FAB and $^1$H NMR. $C_{41}H_{24}N_6$ cal. 600.21, found 600.22.

Synthesis Example 6

Synthesis of Compound 35

4.69 g (yield 57%) of Compound 35 was synthesized in the same manner as in the synthesis of Compound 1, except that 2-bromoquinoline was used (utilized) instead of bromobenzene and 2,4-di([1,1'-biphenyl]-4-yl)-6-chloro-1,3,5-triazine was used (utilized) instead of 2-chloro-4,6-diphenyl-1,3,5-triazine in the synthesis of Intermediate I-1. The compound obtained therefrom was analyzed through MS/FAB and $^1$H NMR. $C_{49}H_{30}N_6$ cal. 702.25, found 702.26.

Synthesis Example 7

Synthesis of Compound 43

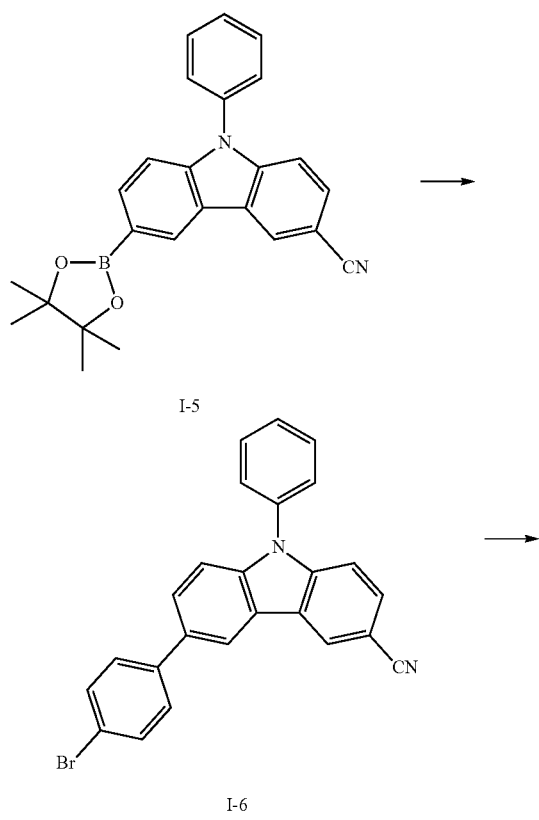

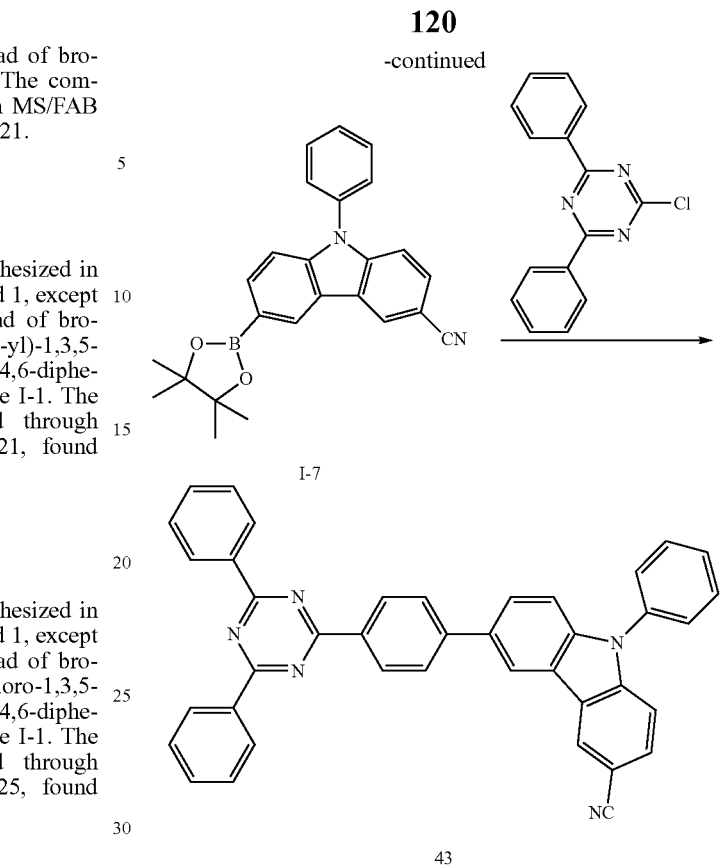

1) Synthesis of Intermediate I-6

4.61 g (11.7 mmol) of Intermediate I-5, 4.14 g (17.6 mmol) of 1,4-dibromobenzene, 0.68 g (0.585 mmol) of Pd(PPh$_3$)$_4$, and 4.85 g (35.1 mmol) of K$_2$CO$_3$ were dissolved in 60 mL of THF and 30 mL of H$_2$O and then stirred at 80° C. for 12 hours to prepare a reaction solution. The reaction solution was cooled to room temperature and then extracted three times with 30 mL of water and 30 mL of ethylacetate to collect organic layers. The collected organic layers were dried with magnesium sulfate, a solvent was evaporated therefrom to obtain residues, which were separated and purified by using (utilizing) silica gel column chromatography to obtain 3.76 g (yield 76%) of Intermediate I-6. The compound obtained therefrom was analyzed through LC-MS. $C_{25}H_{15}BrN_2$: M$^+$ 422.0.

2) Synthesis of Intermediate I-7

3.76 g (8.89 mmol) of Intermediate I-6, 0.36 g (0.44 mmol) of Pd(dppf)$_2$Cl$_2$, and 2.62 g (26.7 mmol) of KOAc were dissolved in 80 mL of DMSO and then stirred at 150° C. for 24 hours to prepare a reaction solution. The reaction solution was cooled to room temperature, 100 mL of water was added thereto and then extracted three times with 50 mL of CH$_2$Cl$_2$ to collect organic layers. The collected organic layers were dried with magnesium sulfate and a solvent was evaporated therefrom to obtain residues, which were separated and purified by using (utilizing) silica gel column chromatography to obtain 3.64 g (yield 87%) of Intermediate I-7. The compound obtained therefrom was analyzed through LC-MS. $C_{31}H_{27}BN_2O_2$: M$^+$ 470.2.

3) Synthesis of Compound 43

3.64 g (7.73 mmol) of Intermediate I-7, 2.07 g (7.73 mmol) of 2-chloro-4,6-diphenyl-1,3,5-triazine, 0.45 g (0.387 mmol) of Pd(PPh$_3$)$_4$, and 3.21 g (23.2 mmol) of K$_2$CO$_3$ were dissolved in 60 mL of THF and 30 mL of H$_2$O and then stirred at a temperature of 80° C. for 12 hours to prepare a reaction solution. The reaction solution was cooled to room temperature and then extracted three times with 30 mL of water and 30 mL of ethylacetate to collect organic layers. The collected organic layers were dried with magnesium sulfate, a solvent was evaporated therefrom to obtain residues, which were separated and purified by using (utilizing) silica gel column chromatography to obtain 3.03 g (yield 68%) of Compound 43. The compound obtained therefrom was analyzed through. MS/FAB 2H $^1$H NMR. $C_{40}H_{25}N_5$ cal. 575.21, found 575.23.

Synthesis Example 8

Synthesis of Compound 48

3.18 g (yield 63%) of Compound 48 was synthesized in the same manner as in the synthesis of Compound 43, except that 3-(4-bromophenyl)pyridine was used (utilized) instead of bromobenzene in the synthesis of Intermediate I-1. The compound produced was analyzed through MS/FAB and $^1$H NMR. $C_{45}H_{28}N_6$ cal. 652.24, found 652.25.

Synthesis Example 9

Synthesis of Compound 54

4.08 g (yield 69%) of Compound 54 was synthesized in the same manner as in the synthesis of Compound 43, except that 2-bromo-dibenzo[b,d]furan was used (utilized) instead of bromobenzene and 2-chloro-4,6-di-(naphthalene-1-yl)-1,3,5-triazine was used (utilized) instead of 2-chloro-4,6-diphenyl-1,3,5-triazine in the synthesis of intermediate I-1. The compound produced was analyzed through MS/FAB and $^1$H NMR. $C_{54}H_{31}N_5O$ cal. 765.25, found 765.23.

Synthesis Example 10

Synthesis of Compound 59

3.71 g (yield 66%) of Compound 59 was synthesized in the same manner as in the synthesis of Compound 43, except that 2-bromoquinoline was used (utilized) instead of bromobenzene and 2-chloro-4,6-di-(naphthalene-2-yl)-1,3,5-triazine was used (utilized) instead of 2-chloro-4,6-diphenyl-1,3,5-triazine in the synthesis of Intermediate I-1. The compound produced was analyzed through MS/FAB and $^1$H NMR. $C_{51}H_{30}N_6$ cal. 726.25, found 726.27.

Synthesis Example 11

Synthesis of Compound 68

3.66 g (yield 70%) of Compound 68 was synthesized in the same manner as in the synthesis of Compound 43, except that 1-bromonaphthalene was used (utilized) instead of bromobenzene and 1,4-dibromo-naphthalene was used (utilized) instead of 1,4-dibromobenzene in the synthesis of Intermediate I-1. The compound produced was analyzed through MS/FAB and $^1$H NMR. $C_{48}H_{29}N_5$ cal. 675.24, found 675.23.

Synthesis Example 12

Synthesis of Compound 75

3.76 g (yield 67%) of Compound 75 was synthesized in the same manner as in the synthesis of Compound 43, except that 1,4-dibromo-naphthalene was used instead of 1,4-dibromobenzene and 2-chloro-4,6-di-(naphthalene-2-yl)-1,3,5-triazine was used (utilized) instead of 2-chloro-4,6-diphenyl-1,3,5-triazine in the synthesis of Intermediate I-6. The compound produced was analyzed through MS/FAB and $^1$H NMR. $C_{52}H_{31}N_5$ cal. 725.26, found 725.28.

Synthesis Example 13

Synthesis of Compound 84

3.31 g (yield 59%) of Compound 84 was synthesized in the same manner as in the synthesis of Compound 43, except that 2-bromonaphthalene was used (utilized) instead of bromobenzene in the synthesis of Intermediate I-1,5-bromo-2-iodopyridine was used (utilized) instead of 1,4-dibromobenzene in the synthesis of Intermediate I-6, and 2-chloro-4,6-di-(naphthalene-2-yl)-1,3,5-triazine was used (utilized) instead of 2-chloro-4,6-diphenyl-1,3,5-triazine in the synthesis of Compound 43. The compound produced was analyzed through MS/FAB and $^1$H NMR. $C_{51}H_{30}H_6$ cal. 726.84, found 726.85.

Synthesis Example 14

Synthesis of Compound 88

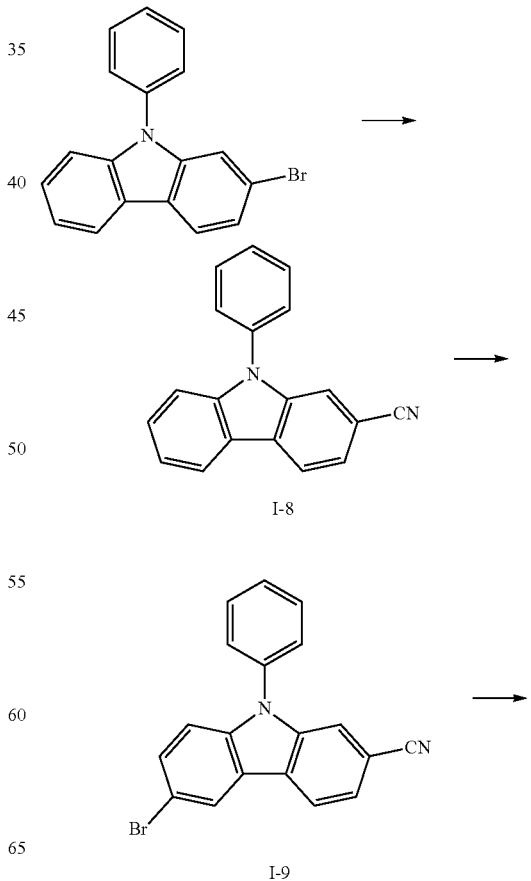

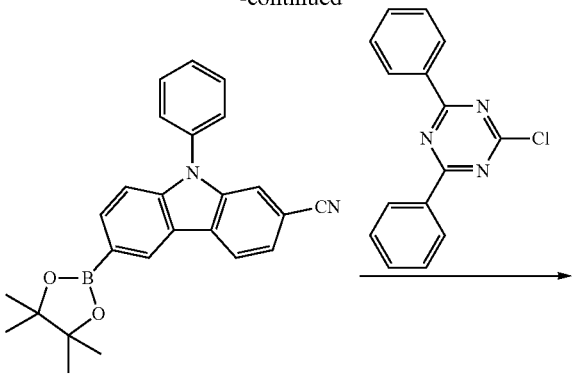

I-10

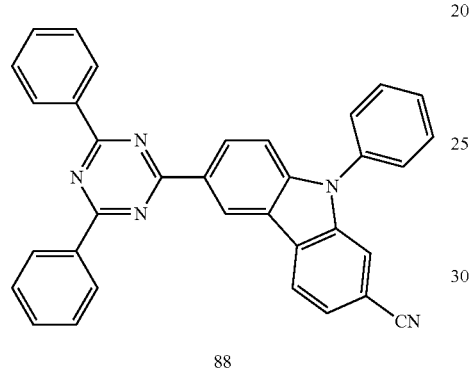

88

1) Synthesis of Intermediate I-8

6.12 g (19.0 mmol) of 2-bromo-9-a phenyl-9H-a carbazole and 2.55 g (28.5 mmol) of CuCN were dissolved in 70 mL of DMF and then stirred at 150° C. for 24 hours to prepare a reaction solution. The reaction solution was cooled to room temperature and 60 mL of ammonia water and 60 mL of water were added thereto and then extracted three times with 50 mL of $CH_2Cl_2$ to collect organic layers. The collected organic layers were dried with magnesium sulfate, a solvent was evaporated therefrom to obtain residues, which were separated and purified by using (utilizing) silica gel column chromatography to obtain 4.74 g (yield 93%) of Intermediate I-8. The compound obtained therefrom was analyzed through LC-MS. $C_{19}H_{12}N_2$: $M^+$ 268.1.

2) Synthesis of Intermediate I-9

3.14 g (17.7 mmol) of N-bromosuccinimide was added to a solution in which 4.74 g (17.7 mmol) of Intermediate I-8 was dissolved in 80 mL of $CH_2Cl_2$ and then stirred at room temperature for 8 hours to prepare a reaction solution. 60 mL of water was added to the reaction solution and then extracted three times with 50 mL of $CH_2Cl_2$ to collect organic layers. The collected organic layers were dried with magnesium sulfate, a solvent was evaporated therefrom and then recrystallized with methanol to obtain 5.83 g (yield 95%) of Intermediate I-9. The compound obtained therefrom was analyzed through LC-MS. $C_{19}H_{11}BrN_2$: $M^+$ 346.0.

3) Synthesis of Intermediate I-10

5.82 g (16.8 mmol) of Intermediate I-9, 0.68 g (0.84 mmol) of $Pd(dppf)_2Cl_2$, and 4.92 g (50.1 mmol) of KOAc were dissolved in 80 mL of DMSO and then stirred at 150° C. for 24 hours to prepare a reaction solution. The reaction solution was cooled to room temperature, 100 mL of water was added thereto, and then extracted three times with 50 mL of $CH_2Cl_2$ to collect organic layers. The organic layers were dried with magnesium sulfate, a solvent was evaporated therefrom to obtain residues, which were separated and purified by using (utilizing) silica gel column chromatography to obtain 4.31 g (yield 65%) of Intermediate I-10. The compound obtained therefrom was analyzed through LC-MS. $C_{25}H_{23}BN_2O_2$: $M^+$ 394.2.

4) Synthesis of Compound 88

4.31 g (10.9 mmol) of Intermediate I-10, 2.92 g (10.9 mmol) of 2-chloro-4,6-diphenyl-1,3,5-triazine, 0.63 g (0.55 mmol) of $Pd(PPh_3)_4$, and 4.52 g (32.7 mmol) of $K_2CO_3$ were dissolved in 60 mL of THF and 30 mL of $H_2O$, and then stirred at 80° C. for 12 hours to prepare a reaction solution. The reaction solution was cooled to room temperature and then extracted three times with 30 mL of water and 30 mL of ethylacetate to collect organic layers. The collected organic layers were dried with magnesium sulfate and a solvent was evaporated therefrom to obtain residues, which were separated and purified by using (utilizing) silica gel column chromatography to obtain 4.13 g (yield 76%) of Compound 88. The compound obtained therefrom was analyzed through MS/FAB and $^1$H NMR. $C_{34}H_{21}N_5$ cal. 499.18, found 499.20.

Synthesis Example 15

Synthesis of Compound 95

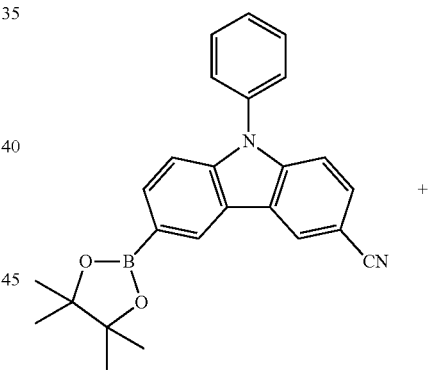

I-5

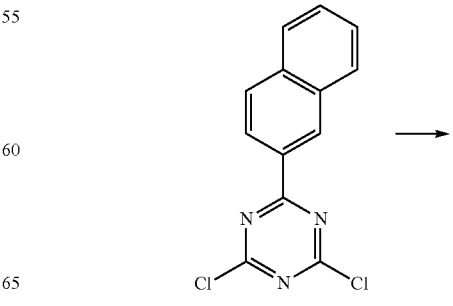

-continued

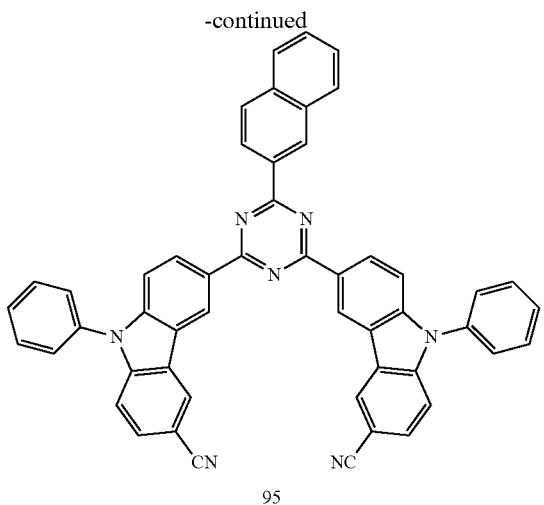

95

7.89 g (20.0 mmol) of Intermediate I-5, 2.76 g (10.0 mmol) of 2,4-dichloro-6-(naphthalene-2-yl)-1,3,5-triazine, 0.58 g (0.50 mmol) of Pd(PPh$_3$)$_4$, and 4.15 g (30.0 mmol) of K$_2$CO$_3$ were dissolved in 60 mL of THF and 30 mL of H$_2$O and then stirred at 80° C. for 12 hours to obtain a reaction solution. The reaction solution was cooled to room temperature and then extracted three times with 30 mL of water and 30 mL of ethylacetate to collect organic layers. The collected organic layers were dried with magnesium sulfate, a solvent was evaporated therefrom to obtain residues, which were separated and purified by using (utilizing) silica gel column chromatography to obtain 3.85 g (yield 52%) of Compound 95. The compound obtained therefrom was analyzed through MS/FAB and $^1$H NMR. C$_{51}$H$_{29}$N$_7$ cal. 739.25, found 739.26.

Additional compounds were synthesized by using (utilizing) the same synthesis pathway and synthesis method, and by using (utilizing) suitable intermediate materials. $^1$H NMR and MS/FAB of the synthesized compounds are shown in Table 1.

In addition to the compounds shown in Table 1, other compounds may be easily synthesized by one of ordinary skill in the art based on the synthesis pathway and raw materials described above.

TABLE 1

| Compound | $^1$H NMR (CDCl$_3$, 400 MHz) δ | MS/FAB found | MS/FAB calc. |
|---|---|---|---|
| 1 | δ = 8.85-8.83 (m, 1H), 8.80-8.78 (m, 4H), 8.57-8.54 (m, 1H), 8.47 (dd, 1H), 8.06 (d, 1H), 7.70 (d, 1H), 7.54-7.41 (m, 10H), 7.34-7.28 (m, 1H), 7.25 (dd, 1H) | 499.17 | 499.18 |
| 3 | δ = 8.88-8.86 (m, 1H), 8.81-8.78 (m, 4H), 8.58-8.55 (m, 1H), 8.57 (dd, 1H), 8.03 (d, 1H), 7.92 (d, 1H), 7.86 (d, 1H), 7.73 (d, 1H), 7.69 (d, 1H), 7.61-7.38 (m, 10H), 7.26 (d, 1H) | 549.21 | 549.20 |
| 13 | δ = 8.83-8.81 (m, 1H), 8.68 (d, 2H), 8.58 (d, 1H), 8.51 (dd, 1H), 8.19 (d, 2H), 8.10 (d, 1H), 8.06 (d, 2H), 7.99 (d, 2H), 7.71-7.63 (m ,5H), 7.52-7.47 (m, 6H), 7.34-7.24 (m, 2H) | 599.20 | 599.21 |
| 20 | δ = 8.87-8.84 (m, 1H), 8.69-8.66 (m, 3H), 8.53 (dd, 1H), 8.28 (d, 1H), 8.18 (d, 2H), 8.09 (d, 2H), 8.03-7.93 (m, 5H), 7.77-7.72 (m, 3H), 7.68-7.63 (m, 4H), 7.61-7.57 (m, 2H), 7.52-7.48 (m, 2H) | 650.21 | 650.22 |
| 28 | δ = 9.16 (d, 1H), 8.92 (d, 2H), 8.74 (dd, 2H), 8.65-8.63 (m, 2H), 8.50 (d, 1H), 8.32 (dd, 1H), 8.18-8.12 (m, 5H), 8.06-8.02 (m, 3H), 7.72 (d, 1H), 7.67 (t, 2H), 7.58 (t, 2H), 7.48 (dd, 1H), 7.32 (d, 1H) | 600.22 | 600.21 |
| 35 | δ = 8.93-8.92 (m, 1H), 8.67-8.65 (m, 1H), 8.53-8.48 (m, 5H), 8.27 (d, 1H), 8.02-7.93 (m, 7H), 7.77-7.72 (m, 3H), 7.60-7.53 (m, 6H), 7.48-7.44 (m, 4H), 7.38-7.35 (m, 2H) | 702.26 | 702.25 |
| 43 | δ = 8.83-8.77 (m, 4H), 8.56-8.53 (m, 2H), 8.46-8.44 (m, 1H), 8.18-8.16 (m, 1H), 8.06-8.03 (m, 2H), 7.87 (d, 1H), 7.69 (d, 1H), 7.62 (d, 1H), 7.56-7.41 (m, 10H), 7.33-7.24 (m, 2H) | 575.23 | 575.21 |
| 48 | δ = 8.94 (dd, 1H), 8.81-8.78 (m, 4H), 8.56-8.52 (m, 2H), 8.47-8.43 (m, 2H), 8.19-8.17 (m, 1H), 8.08-8.03 (m, 3H), 7.70 (d, 1H), 7.63 (d, 1H), 7.55-7.50 (m, 6H), 7.46-7.37 (m, 5H), 7.26 (d, 1H), 7.15 (d, 1H) | 652.25 | 652.24 |
| 54 | δ = 8.68 (d, 2H), 8.61-8.57 (m, 2H), 8.48-8.46 (m, 1H), 8.21-8.17 (mm, 3H), 8.11-8.04 (m, 4H), 7.98 (dd, 2H), 7.90-7.85 (m, 2H), 7.71-7.63 (m, 7H), 7.52-7.47 (m, 2H), 7.42-7.33 (m, 4H), 7.27 (d, 1H), 7.18 (d, 1H) | 765.23 | 765.25 |
| 59 | δ = 8.93 (d, 2H), 8.74 (dd, 2H), 8.56-8.53 (m, 3H), 8.30-8.27 (m, 2H), 8.19-8.13 (m, 4H), 8.07-7.93 (rn, 6H), 7.76-7.64 (m, 6H), 7.60-7.56 (m, 4H), 7.42 (d, 1H) | 726.27 | 726.25 |
| 68 | δ = 8.83-8.81 (m, 4H), 8.66 (d, 1H), 8.47-8.42 (m, 2H), 8.28 (d, 1H), 8.19 (d, 1H), 8.08 (d, 1H), 8.04 (d, 1H), 7.78 (d, 1H), 7.72-7.63 (m, 7H), 7.55-7.41 (m, 8H), 7.28 (t, 1H), 7.16 (t, 1H) | 675.23 | 675.24 |
| 75 | δ = 9.00 (d, 2H), 8.75 (d, 2H), 8.66 (d, 1H), 8.47-8.42 (m, 2H), 8.30 (d, 1H), 8.20-8.12 (m, 5H), 8.03 (t, 3H), 7.05 (d, 1H), 7.71-7.64 (m, 4H), 7.60-7.56 (m, 2H), 7.50-7.45 (m, 5H), 7.34-7.24 (m, 2H), 7.18-7.14 (m, 1H) | 725.28 | 725.26 |

TABLE 1-continued

| Compound | $^1$H NMR (CDCl$_3$, 400 MHz) δ | MS/FAB found | MS/FAB calc. |
|---|---|---|---|
| 84 | δ = 9.23 (d, 1H), 8.92-8.85 (m, 4H), 8.74 (d, 2H), 8.53-8.51 (m, 1H), 8.18-8.13 (m, 6H), 8.02 (d, 2H), 7.93-7.86 (m, 3H), 7.74-7.40 (m, 10H), 7.27 (d, 1H) | 726.85 | 726.84 |
| 88 | δ = 8.81-8.78 (m, 4H), 8.76-8.75 (m, 1H), 8.48 (dd, 1H), 8.07-8.03 (m, 2H), 7.76 (dd, 1H), 7.65 (d, 1H), 7.58-7.48 (m, 8H), 7.45-7.41 (m, 2H), 7.32-7.28 (m, 1H) | 499.20 | 499.18 |
| 95 | δ = 8.92, (d, 1H), 8.84-8.82 (m, 2H), 8.74 (d, 1H), 8.57 (d, 2H), 8.47 (d, 2H), 8.17 (d, 1H), 8.13 (d, 1H), 8.06 (d, 2H), 8.03 (d ,1H), 7.70 (d, 2H), 7.66 (d, 1H), 7.60-7.46 (m, 9H), 7.34-7.24 (m, 4H) | 739.26 | 739.25 |

Example 1

An ITO glass substrate including an ITO layer having a thickness of 1200 Å was cut to a size of 50 mm×50 mm×0.7 mm, sonicated by using (utilizing) isopropyl alcohol for 10 minutes and pure water for 10 minutes, and cleaned by irradiating ultraviolet rays and exposing to ozone for 10 minutes. Then, the ITO glass substrate was mounted on a vacuum deposition apparatus.

2-TNATA was deposited on the ITO layer acting as an anode to form a hole injection layer having a thickness of 600 Å, NPB was deposited on the hole injection layer to form a hole transport layer having a thickness of 300 Å, and then, DNA (host) and DPAVBi (dopant) were co-deposited at a weight ratio of 98:2 on the emission layer to form an emission layer having a thickness of 300 Å. Thereafter, Compound 1 was deposited on the emission layer to form an electron transport layer having a thickness of 300 Å, LiF was deposited on the electron transport layer to form an electron injection layer having a thickness of 10 Å, and Al was deposited on the electron injection layer to form a cathode having a thickness of 3000 Å, thereby completing the manufacture of an organic light-emitting device.

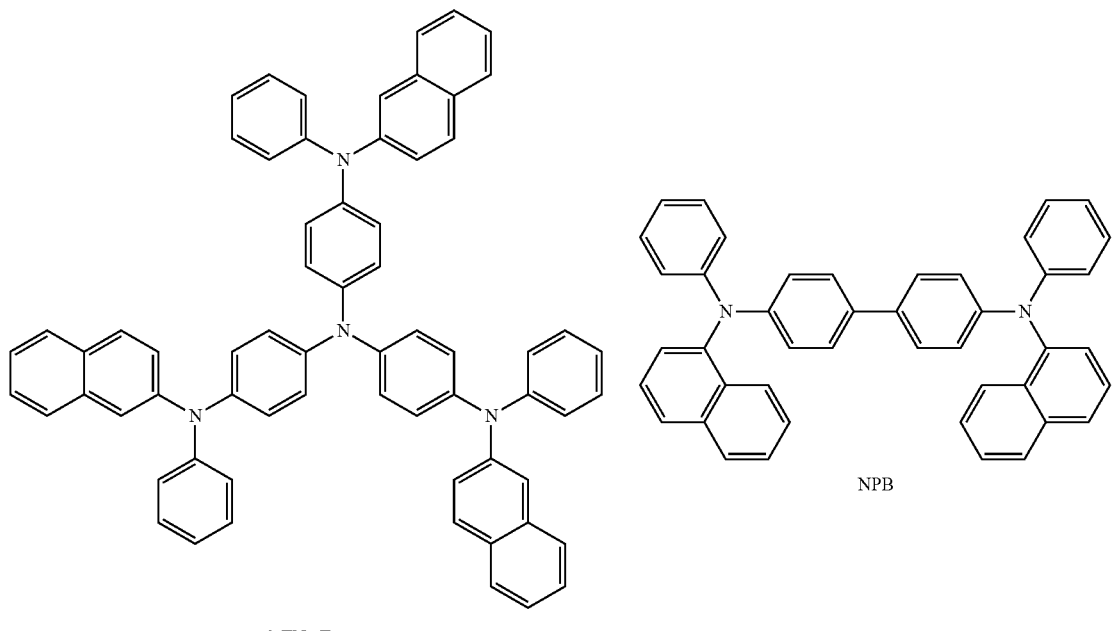

2-TNATA

NPB

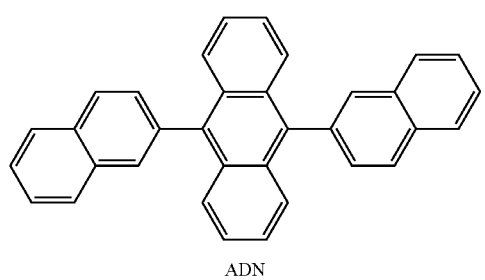

ADN

-continued

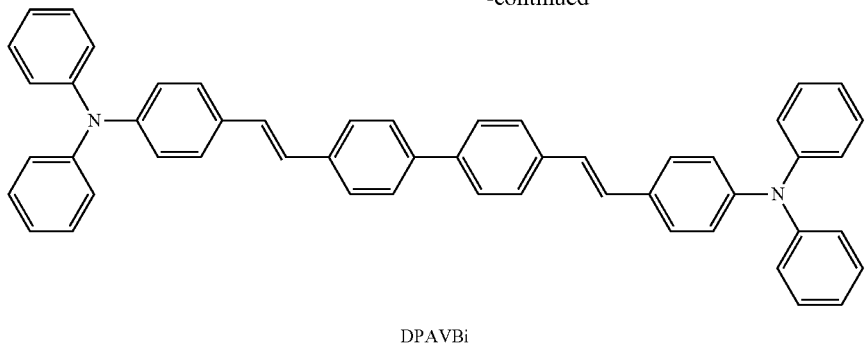

DPAVBi

Example 2

An organic light-emitting device was manufactured in the same manner as in Example 1, except that in forming an electron transport layer, Compound 13 was used (utilized) instead of Compound 1.

Example 3

An organic light-emitting device was manufactured in the same manner as in Example 1, except that in forming an electron transport layer, Compound 28 was used (utilized) instead of Compound 1.

Example 4

An organic light-emitting device was manufactured in the same manner as in Example 1, except that in forming an electron transport layer, Compound 43 was used (utilized) instead of Compound 1.

Example 5

An organic light-emitting device was manufactured in the same manner as in Example 1, except that in forming an electron transport layer, Compound 48 was used (utilized) instead of Compound 1.

Example 6

An organic light-emitting device was manufactured in the same manner as in Example 1, except that in forming an electron transport layer, Compound 68 was used (utilized) instead of Compound 1.

Example 7

An organic light-emitting device was manufactured in the same manner as in Example 1, except that in forming an electron transport layer, Compound 75 was used (utilized) instead of Compound 1.

Example 8

An organic light-emitting device was manufactured in the same manner as in Example 1, except that in forming an electron transport layer, Compound 84 was used (utilized) instead of Compound 1.

Example 9

An organic light-emitting device was manufactured in the same manner as in Example 1, except that in forming an electron transport layer, Compound 88 was used (utilized) instead of Compound 1.

Example 10

An organic light-emitting device was manufactured in the same manner as in Example 1, except that in forming an electron transport layer, Compound 95 was used (utilized) instead of Compound 1.

Comparative Example 1

An organic light-emitting device was manufactured in the same manner as in Example 1, except that in forming an electron transport layer, Compound A was used (utilized) instead of Compound 1.

Compound A

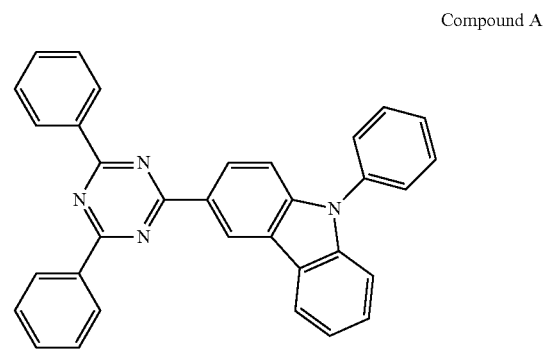 [SMILES: c1ccc(-c2nc(-c3ccccc3)nc(-c3ccc4c(c3)c3ccccc3n4-c3ccccc3)n2)cc1]

Comparative Example 2

An organic light-emitting device was manufactured in the same manner as in Example 1, except that in forming an electron transport layer, Compound B was used (utilized) instead of Compound 1.

Compoound B

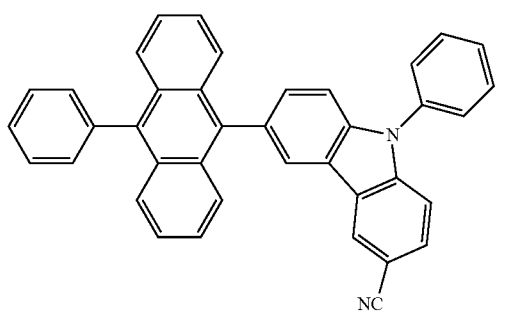

Comparative Example 3

An organic light-emitting device was manufactured in the same manner as in Example 1, except that in forming an electron transport layer, Compound C was used (utilized) instead of Compound 1.

Compound C

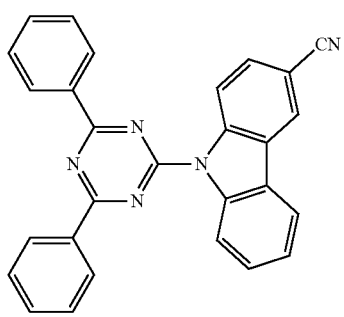

Evaluation Example 1

The driving voltage, current density, brightness, efficiency, emission color, and half-life of the organic light-emitting devices manufactured according to Examples 1 to 10, and Comparative Examples 1, 2, and 3 were measured by using (utilizing) a Kethley SMU 236 and a brightness photometer PR650, and results thereof are shown in Table 2.

TABLE 2

|  | Electron Transport Layer | Driving voltage (V) | Current density (mA/cm$^2$) | Brightness (cd/m$^2$) | Efficiency (cd/A) | Emission color | Half-life (hr @100 mA/cm$^2$) |
|---|---|---|---|---|---|---|---|
| Example 1 | Compound 1 | 4.35 | 50 | 3,980 | 8.25 | blue | 675 hr |
| Example 2 | Compound 13 | 4.42 | 50 | 3,750 | 8.07 | blue | 652 hr |
| Example 3 | Compound 28 | 4.30 | 50 | 3,525 | 7.81 | blue | 667 hr |
| Example 4 | Compound 43 | 4.83 | 50 | 3,500 | 7.05 | blue | 420 hr |
| Example 5 | Compound 48 | 4.97 | 50 | 3,375 | 6.98 | blue | 458 hr |
| Example 6 | Compound 68 | 5.02 | 50 | 3,625 | 7.62 | blue | 537 hr |
| Example 7 | Compound 75 | 5.00 | 50 | 3,610 | 7.53 | blue | 561 hr |
| Example 8 | Compound 84 | 4.86 | 50 | 3,380 | 7.19 | blue | 503 hr |
| Example 9 | Compound 88 | 4.37 | 50 | 3,860 | 8.22 | blue | 468 hr |
| Example 10 | Compound 95 | 4.75 | 50 | 3,695 | 7.35 | blue | 552 hr |
| Comparative Example 1 | Compound A | 5.23 | 50 | 3,325 | 6.78 | blue | 326 hr |
| Comparative Example 2 | Compound B | 5.01 | 50 | 3,180 | 5.36 | blue | 502 hr |
| Comparative Example 3 | Compound C | 5.30 | 50 | 2,805 | 5.15 | blue | 357 hr |

From Table 2, it may be concluded that the driving voltage, current density, brightness, efficiency, and half-life of the organic light-emitting devices manufactured according to Examples 1 to 10 are better than the driving voltage, current density, brightness, efficiency, and half-life of the organic light-emitting devices manufactured according to Comparative Examples 1 and 3.

As described above, according to the one or more of the above embodiments of the present invention, an organic light-emitting device including the triazine-based compound may have low driving voltage, high efficiency, and high brightness.

It should be understood that the example embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the FIGURES, it will be understood by those of ordinary skill in the art that various changes in form and details may be made therein without departing from the spirit and scope of the present invention as defined by the following claim, and equivalents thereof.

What is claimed is:

1. A triazine-based compound represented by Formula 1:

Formula 1

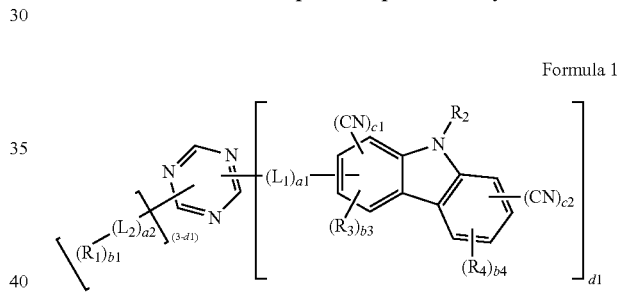

in Formula 1,

L$_1$ and L$_2$ are each independently selected from:
a substituted or unsubstituted C$_3$-C$_{10}$ cycloalkylene group, a substituted or unsubstituted C$_1$-C$_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic hetero-condensed polycyclic group, except for a substituted or unsubstituted anthracenylene group and a substituted or unsubstituted pyrenylene group;

a1 and a2 are each independently selected from integers of 0 to 6;

$R_1$ is selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic hetero-condensed polycyclic group;

$R_2$ is selected from a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic hetero-condensed polycyclic group;

$R_3$ and $R_4$ are each independently selected from a hydrogen, a deuterium, —F, —Cl, —Br, —I, a cyano group, a nitro group, a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic hetero-condensed polycyclic group;

at least one substituent for each of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group group, substituted divalent non-aromatic hetero-condensed polycyclic group, substituted $C_1$-$C_{60}$ alkyl group, substituted $C_6$-$C_{60}$ aryl group, substituted $C_1$-$C_{60}$ heteroaryl group, substituted monovalent non-aromatic condensed polycyclic group, and substituted monovalent non-aromatic hetero-condensed polycyclic group is selected from:

a deuterium, —F, —Cl, —Br, —I, a hydroxyl group, a cyano group, a nitro group, an amino group, an amidino group, a hydrazine, a hydrazone, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, and —Si($Q_1$)($Q_2$)($Q_3$);

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine, a hydrazone, a carboxyl group and a salt thereof, a sulfonic acid group and a salt thereof, a phosphoric acid group and a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic hetero-condensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic hetero-condensed polycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic hetero-condensed polycyclic group, each substituted with at least one selected from a deuterium, —F, —Cl, —Br, —I, a hydroxyl group, a cyano group, a nitro group, an amino group, an amidino group, a hydrazine, a hydrazone, a carboxyl group and a salt thereof, a sulfonic acid group and a salt thereof, a phosphoric acid group and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a non-aromatic condensed polycyclic group, and a non-aromatic hetero-condensed polycyclic group;

$Q_1$ to $Q_3$ are each independently selected from a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic hetero-condensed polycyclic group;

b1 and b3 are each independently selected from integers of 1 to 3;

b4 is selected from integers of 1 to 4;

c1 and c2 are each independently selected from integers of 0 to 3;

a sum of c1 and c2 is an integer of 1 or greater; and d1 is selected from integers of 1 to 3.

2. The compound of claim 1, wherein $L_1$ and $L_2$ are each independently selected from:

a triazine-based compound represented by any one of Formulae 3-1 to 3-30:

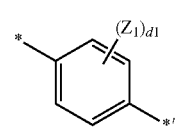

3-1

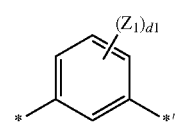

3-2

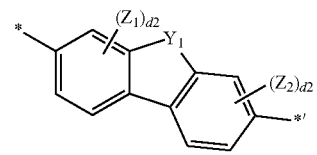

3-3

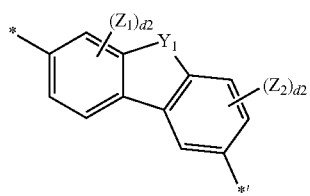
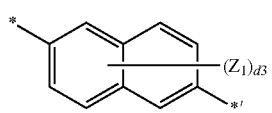
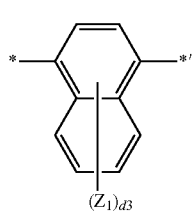
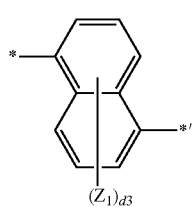
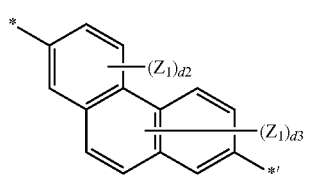
3-4
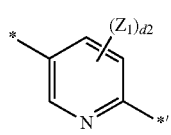
3-5
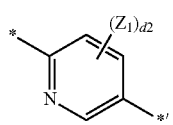
3-6
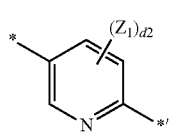
3-7
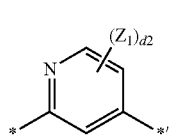
3-8
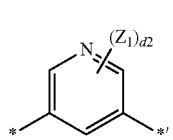
3-9
3-10
3-11
3-12
3-13
3-14
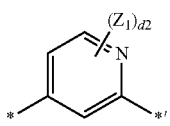
3-15
3-16
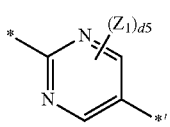
3-17
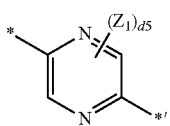
3-18
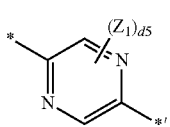
3-19
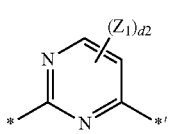
3-20
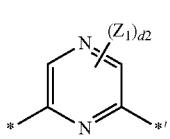
3-21
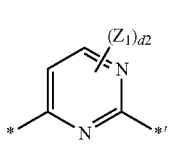
3-22
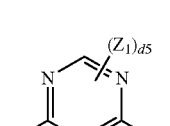
3-23
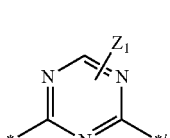
3-24
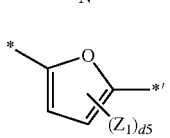
3-25
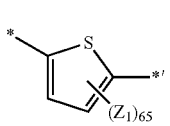

-continued 3-26
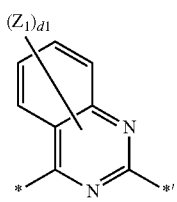

3-27
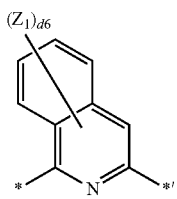

3-28
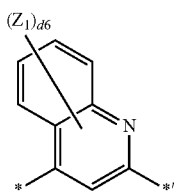

3-29
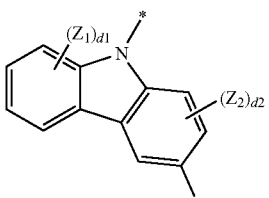

3-30
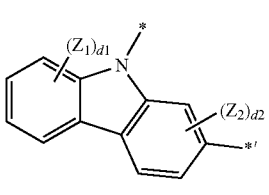

in Formulae 3-1 to 3-30, $Y_1$ is selected from $C(Q_{31})(Q_{32})$, $N(Q_{33})$, an oxygen atom, a sulfur atom, and $Si(Q_{34})(Q_{35})$;

$Q_{31}$ to $Q_{35}$ are each independently selected from a hydrogen, a deuterium, a $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$Z_1$ and $Z_2$ are each independently selected from a hydrogen, a deuterium, —F, —Cl, —Br, —I, a hydroxyl group, a cyano group, a nitro group, an amino group, an amidino group, a hydrazine, a hydrazone, a carboxyl group and a salt thereof, a sulfonic acid group and a salt thereof, a phosphoric acid group and a salt thereof, $C_1$-$C_{20}$ alkyl group, $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 is selected from integers of 1 to 4;
d2 is selected from integers of 1 to 3;
d3 is selected from integers of 1 to 6;
d5 is 1 or 2;
d6 is selected from integers of 1 to 5; and
* and *' are each independently a bonding site to another atom.

3. The compound of claim 1, wherein
$L_1$ and $L_2$ are each independently selected from:
a triazine-based compound represented by any one of Formulae 4-1 to 4-21:

4-1
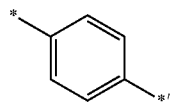

4-2
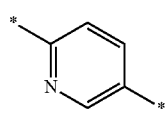

4-3
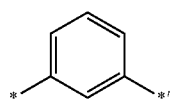

4-4
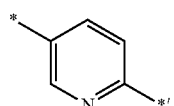

4-5
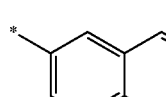

4-6
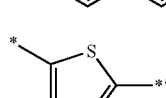

4-7
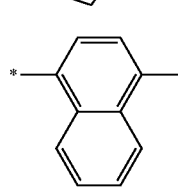

4-8
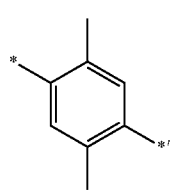

4-9
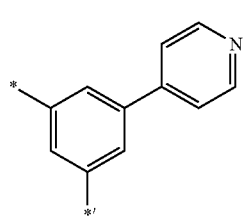

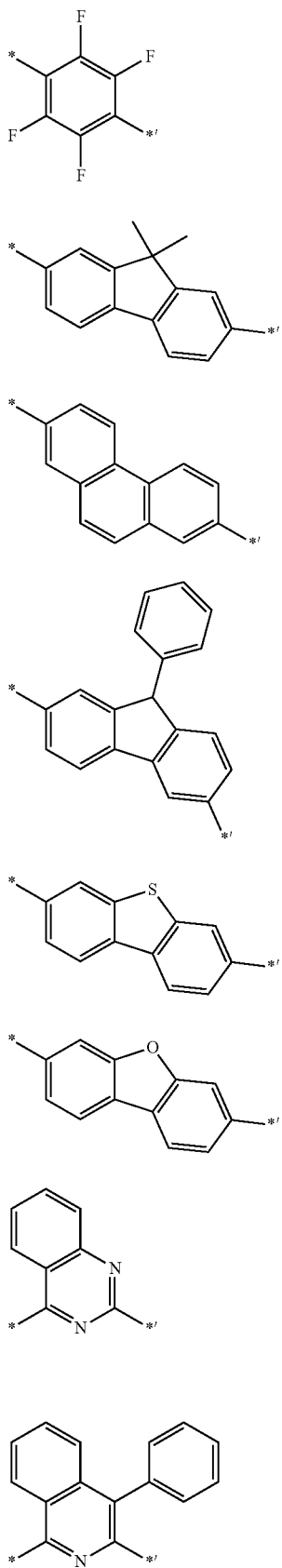

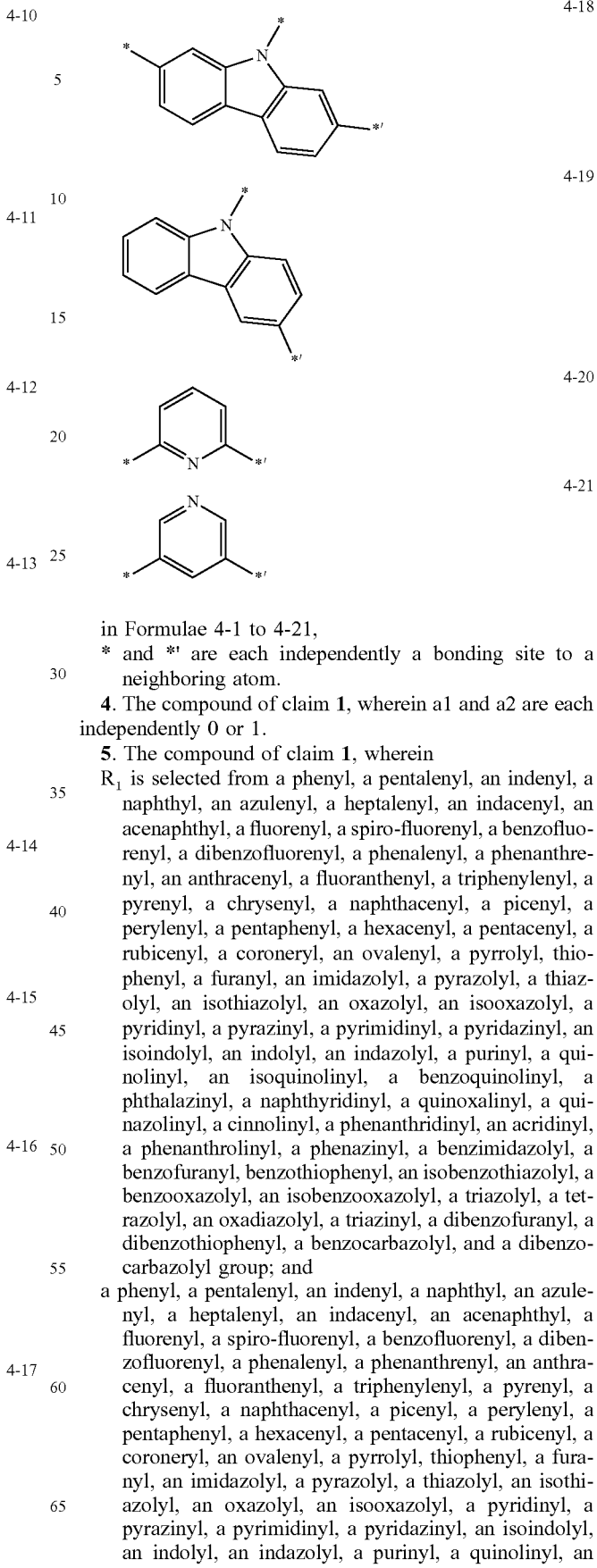

in Formulae 4-1 to 4-21,

\* and \*' are each independently a bonding site to a neighboring atom.

4. The compound of claim 1, wherein a1 and a2 are each independently 0 or 1.

5. The compound of claim 1, wherein $R_1$ is selected from a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a dibenzofuranyl, a dibenzothiophenyl, a benzocarbazolyl, and a dibenzocarbazolyl group; and a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a dibenzofuranyl, dibenzothiophenyl, a benzocarbazolyl, and a dibenzocarbazolyl group, each substituted with at least one selected from, a deuterium, —F, —Cl, —Br, —I, a hydroxyl group, a cyano group, a nitro group, an amino group, an amidino group, a hydrazine, a hydrazone, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, —Si($Q_1$)($Q_2$)($Q_3$), a halogen atom substituted $C_1$-$C_{20}$ alkyl group, a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a carbazolyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a dibenzofuranyl, dibenzothiophenyl, a benzocarbazolyl, and a dibenzocarbazolyl group; and $Q_1$ to $Q_3$ are each independently selected from a $C_1$-$C_{20}$ alkyl group, a phenyl, a naphthyl, and a pyridinyl group.

6. The compound of claim 1, wherein $R_1$ is selected from a phenyl, a naphthyl, a fluorenyl, a phenanthrenyl, a pyridinyl, a pyrazinyl, a pyrimidinyl, a quinolinyl, an isoquinolinyl, and a triazinyl group; and a phenyl, a naphthyl, a fluorenyl, a phenanthrenyl, a pyridinyl, a pyrazinyl, a pyrimidinyl, a quinolinyl, an isoquinolinyl, and a triazinyl group, each substituted with at least one selected from a deuterium, —F, —Cl, —Br, —I, a cyano group, a nitro group, a methyl group, a methoxy group, —Si(CH$_3$)$_3$, —Si(Ph)$_3$, —CF$_3$, a phenyl group, a naphthyl group, a fluorenyl group, a carbazolyl group, a pyridinyl group, a pyrazinyl group, a pyrimidinyl group, a quinolinyl group, an isoquinolinyl group, and a triazinyl group.

7. The compound of claim 1, wherein $R_1$ is any one group selected from Formulae 5-1 to 5-34:

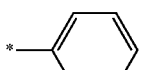

5-1

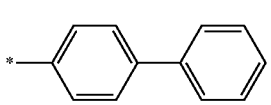

5-2

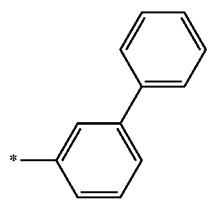

5-3

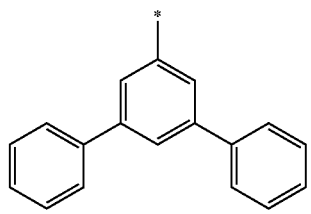

5-4

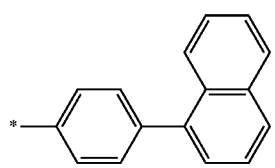

5-5

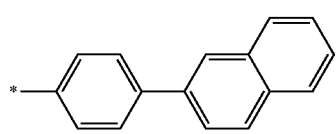

5-6

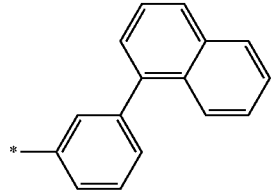

5-7

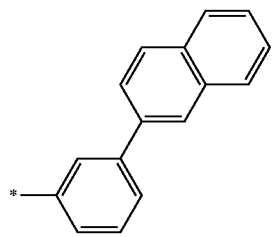

5-8

5-9

-continued
5-10
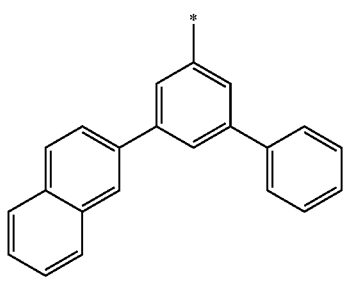
5-11
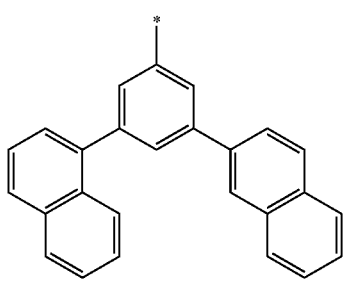
5-12
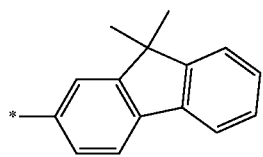
5-13
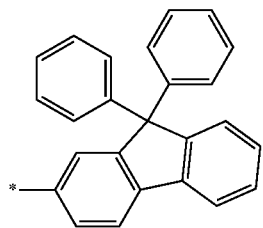
5-14
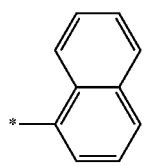
5-15
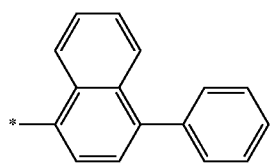
5-16
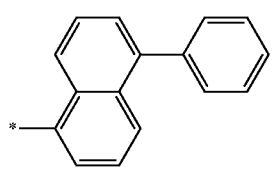
5-17
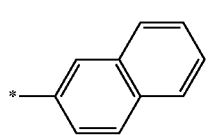
-continued
5-18
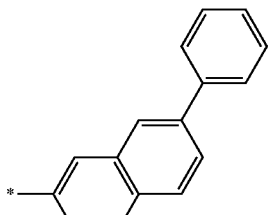
5-19
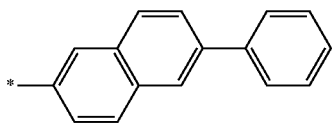
5-20
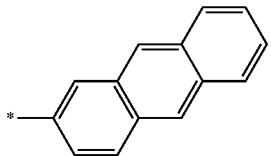
5-21
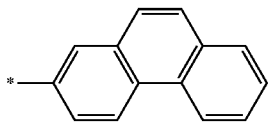
5-22
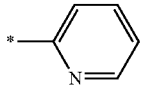
5-23
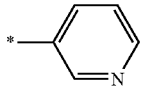
5-24
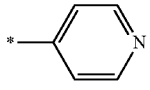
5-25
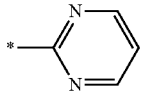
5-26
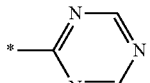
5-27
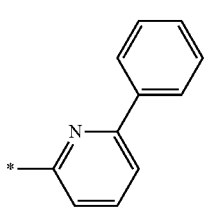
5-28
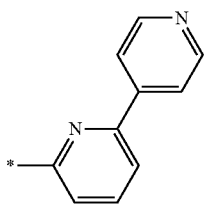

5-29 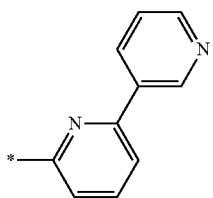

5-30 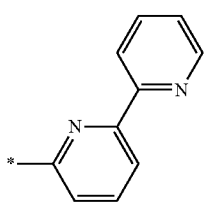

5-31 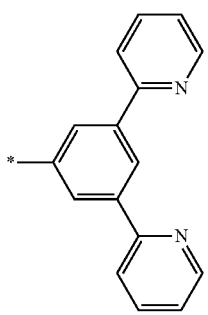

5-32 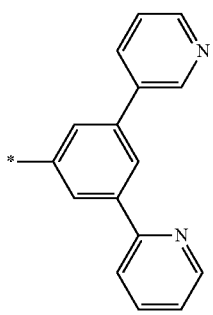

5-33 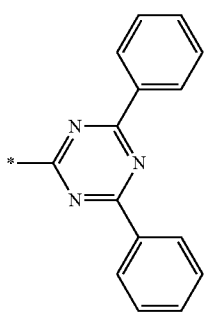

5-34 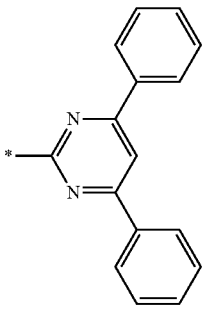

in Formulae 5-1 to 5-34,
* is a bonding site to a neighboring atom.

8. The compound of claim 1, wherein
$R_2$ is selected from a methyl, an ethyl, an n-propyl, an iso-propyl, an n-butyl, an iso-butyl, a tert-butyl, an n-pentyl, an n-hexyl, an n-heptyl, an n-octyl, a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a carbazolyl, a dibenzofuranyl, dibenzothiophenyl, a benzocarbazolyl, and a dibenzocarbazolyl group; and
a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a carbazolyl, a dibenzofuranyl, dibenzothiophenyl, a benzocarbazolyl and a dibenzocarbazolyl group, each substituted with at least one selected from a deuterium, —F, —Cl, —Br, —I, a hydroxyl group, a cyano group, a nitro group, an amino group, an amidino group, a hydrazine, a hydrazone, a carboxyl group and a salt thereof, a sulfonic acid group and a salt thereof, a phosphoric acid group and a salt thereof, a $C_1$-$C_{20}$ alkyl group, a $C_1$-$C_{20}$ alkoxy group, —Si($Q_1$)($Q_2$)($Q_3$), a halogen atom substituted $C_1$-$C_{20}$ alkyl group, a phenyl, a pentalenyl, an indenyl, a naphthyl, an azulenyl, a heptalenyl, an indacenyl, an acenaphthyl, a fluorenyl, a spiro-fluorenyl, a benzofluorenyl, a dibenzofluorenyl, a phenalenyl, a phenanthrenyl, an anthracenyl, a fluoranthenyl, a triphenylenyl, a pyrenyl, a chrysenyl, a naphthacenyl, a picenyl, a perylenyl, a pentaphenyl, a hexacenyl, a pentacenyl, a rubicenyl, a coroneryl, an ovalenyl, a pyrrolyl, thiophenyl, a furanyl, an imidazolyl, a pyrazolyl, a thiazolyl, an isothiazolyl, an oxazolyl, an isooxazolyl, a pyridinyl, a pyrazinyl, a pyrimidinyl, a pyridazinyl, an isoindolyl, an indolyl, an indazolyl, a purinyl, a quinolinyl, an isoquinolinyl, a benzoquinolinyl, a phthalazinyl, a naphthyridinyl, a quinoxalinyl, a quinazolinyl, a cinnolinyl, a carbazolyl, a phenanthridinyl, an acridinyl, a phenanthrolinyl, a phenazinyl, a benzimidazolyl, a benzofuranyl, benzothiophenyl, an isobenzothiazolyl, a benzooxazolyl, an isobenzooxazolyl, a triazolyl, a tetrazolyl, an oxadiazolyl, a triazinyl, a dibenzofuranyl, dibenzothiophenyl, a benzocarbazolyl, and a dibenzocarbazolyl group; and $Q_1$ to $Q_3$ are each independently selected from a $C_1$-$C_{20}$ alkyl group, a phenyl, a naphthyl, and a pyridinyl group.

9. The compound of claim 1, wherein $R_2$ is selected from a methyl, an ethyl, an n-propyl, an iso-propyl, an n-butyl, a phenyl, a naphthyl, a fluorenyl, a phenanthrenyl, a pyridinyl, a pyrazinyl, a pyrimidinyl, a quinolinyl, an isoquinolinyl, a triazinyl, a phenanthrolinyl, a dibenzofuranyl, and a dibenzothiophenyl group; and a phenyl, a naphthyl, a fluorenyl, a phenanthrenyl, a pyridinyl, a pyrazinyl, a pyrimidinyl, a quinolinyl, an isoquinolinyl, a triazinyl, a phenanthrolinyl, a dibenzofuranyl, and a dibenzothiophenyl group, each substituted with at least one selected from a deuterium, —F, —Cl, —Br, —I, a cyano group, a nitro group, a methyl group, a methoxy group, —Si(CH$_3$)$_3$, —Si(Ph)$_3$, —CF$_3$, a phenyl, a naphthyl, a fluorenyl, a carbazolyl, a pyridinyl, a pyrazinyl, a pyrimidinyl, a quinolinyl, an isoquinolinyl, and a triazinyl group.

10. The compound of claim 1, wherein $R_2$ is any one group selected from a methyl, an ethyl, and Formulae 5-1 to 5-38:

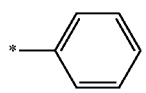

5-1

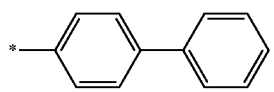

5-2

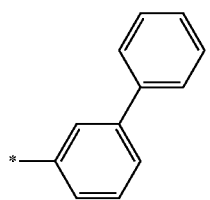

5-3

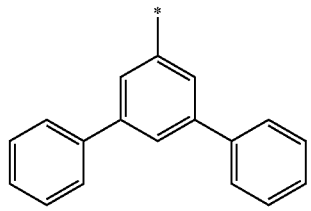

5-4

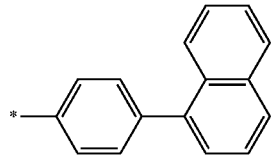

5-5

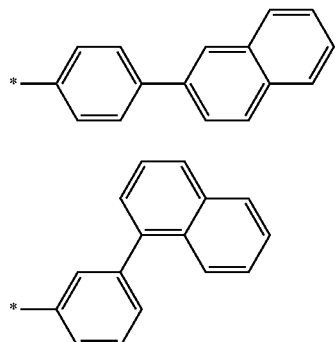

5-6

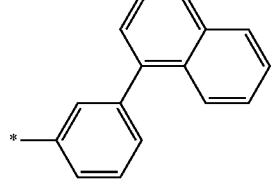

5-7

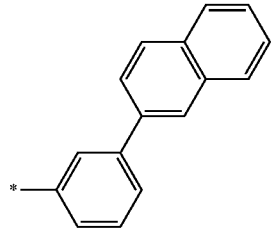

5-8

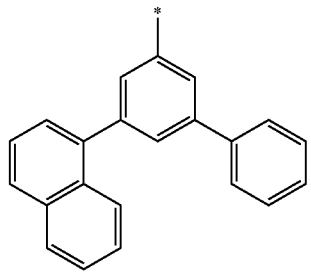

5-9

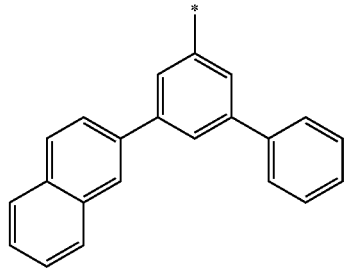

5-10

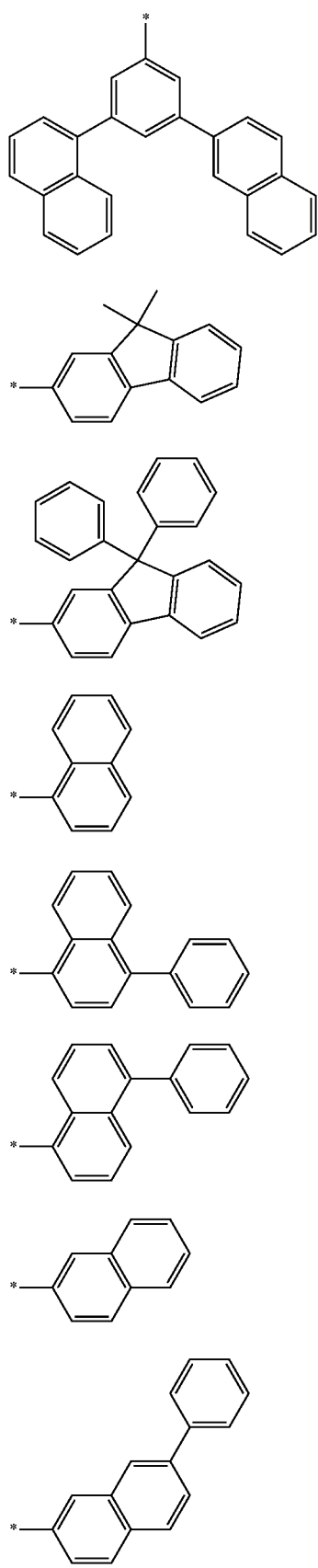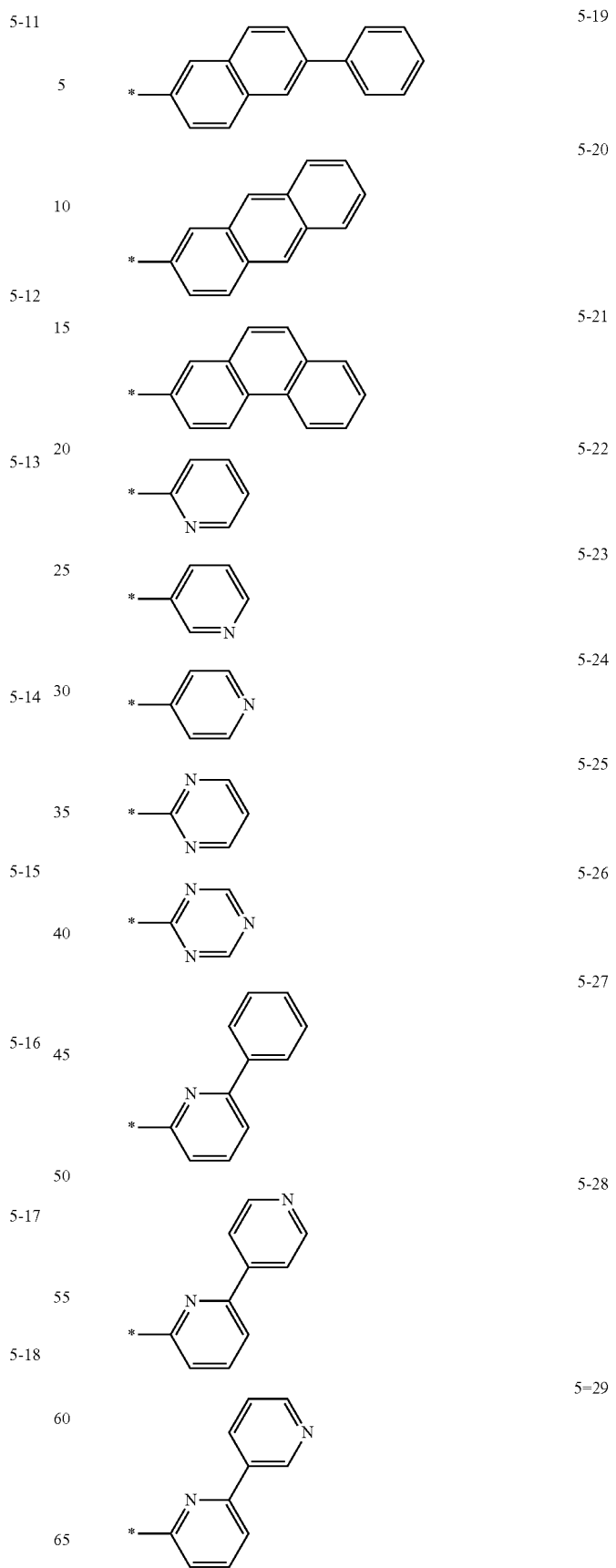

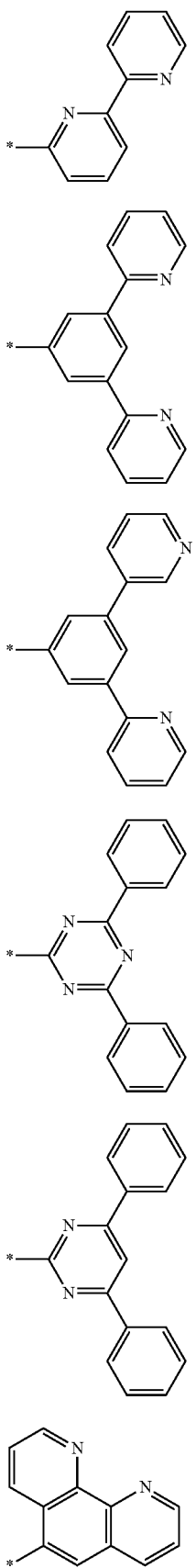

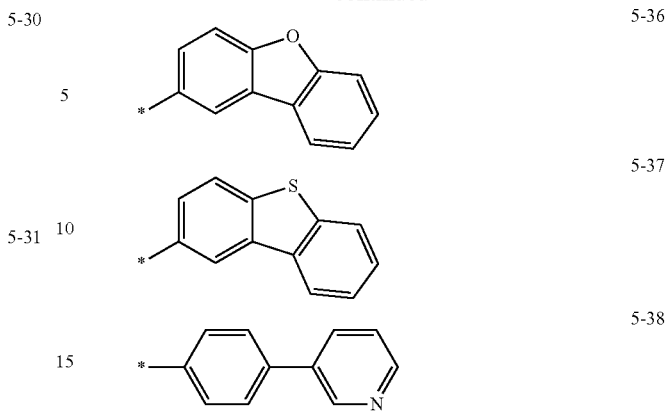

in Formulae 5-1 to 5-38,
* is a bonding site to a neighboring atom.

11. The compound of claim 1, wherein
$R_3$ and $R_4$ are each independently selected from:
a hydrogen, a deuterium, —F, —Cl, —Br, —I, a cyano group, a nitro group, and a $C_1$-$C_{20}$ alkyl group;
a $C_1$-$C_{20}$ alkyl group substituted with at least one selected from a deuterium, —F, —Cl, —Br, —I, a cyano group, a nitro group, a $C_6$-$C_{60}$ aryl group, a $C_1$-$C_{60}$ heteroaryl group, a non-aromatic condensed polycyclic group, and a non-aromatic hetero-condensed polycyclic group;
a $C_6$-$C_{60}$ aryl group, a $C_1$-$C_{60}$ heteroaryl group, a non-aromatic condensed polycyclic group, and a non-aromatic hetero-condensed polycyclic group; and
a $C_6$-$C_{60}$ aryl group, a $C_1$-$C_{60}$ heteroaryl group, a non-aromatic condensed polycyclic group, and a non-aromatic hetero-condensed polycyclic group, each substituted with at least one selected from a deuterium, —F, —Cl, —Br, —I, a cyano group, a nitro group, a $C_1$-$C_{20}$ alkyl group, a $C_6$-$C_{60}$ aryl group, a $C_1$-$C_{60}$ heteroaryl group, a non-aromatic condensed polycyclic group, and a non-aromatic hetero-condensed polycyclic group.

12. The compound of claim 1, wherein b1 is 1.

13. The compound of claim 1, wherein
c1 and c2 are each independently 0 or 1; and
a sum of c1 and c2 is 1 or greater.

14. The compound of claim 1, wherein d1 is 1 or 2.

15. The compound of claim 1, wherein the triazine-based compound is represented by Formula 1A:

Formula 1A

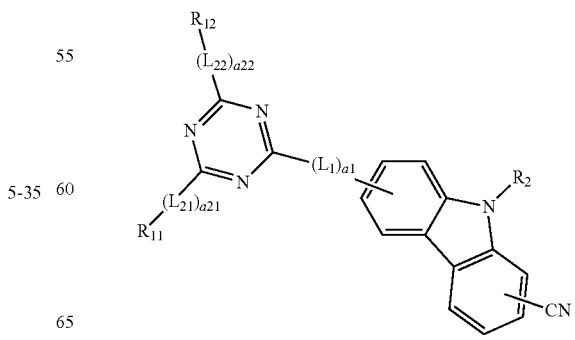

in Formula 1A, $L_{21}$ and $L_{22}$ are each the same as $L_2$ in claim 1;

a21 and a22 are each the same as a2 in claim 1; and $R_{11}$ and $R_{12}$ are each the same as $R_1$ in claim 1.

16. The compound of claim 1, wherein the triazine-based compound may be represented by any one of Formulae 1B and 1C:

Formula 1B

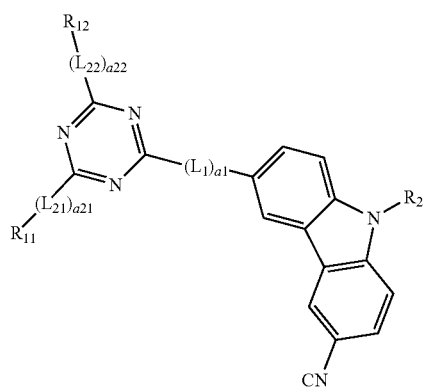

Formula 1C

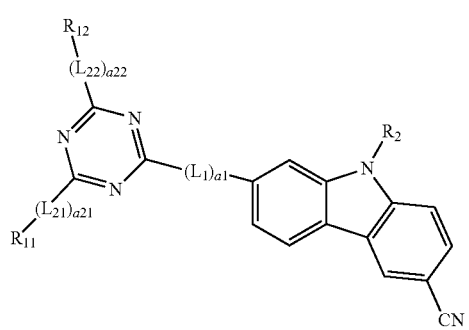

in Formula 1B and 1C, $L_{21}$ and $L_{22}$ are each the same as $L_2$ in claim 1;

a21 and a22 are each the same as a2 in claim 1; and $R_{11}$ and $R_{12}$ are each the same as $R_1$ in claim 1.

17. The compound of claim 1, wherein the triazine-based compound is selected from Compounds 1 to 95:

1

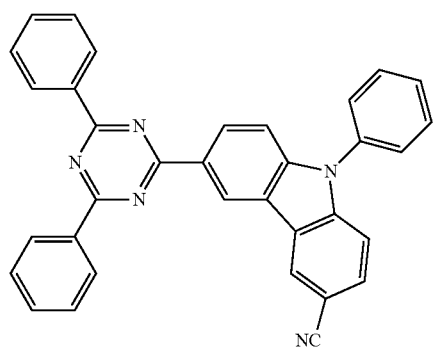

2

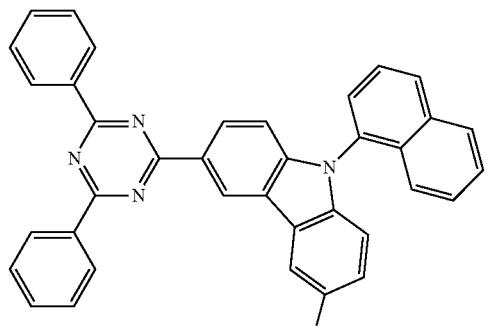

3

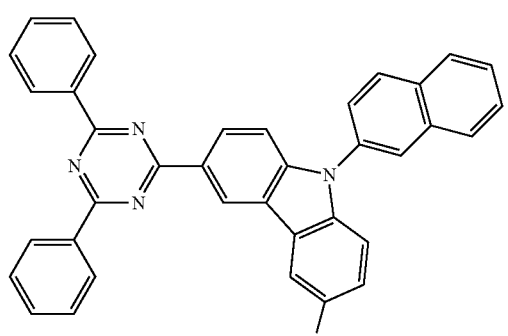

4

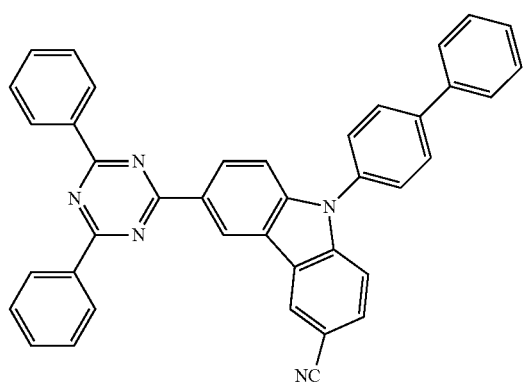

5

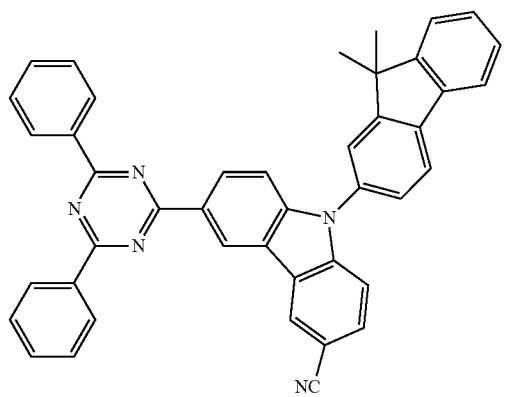

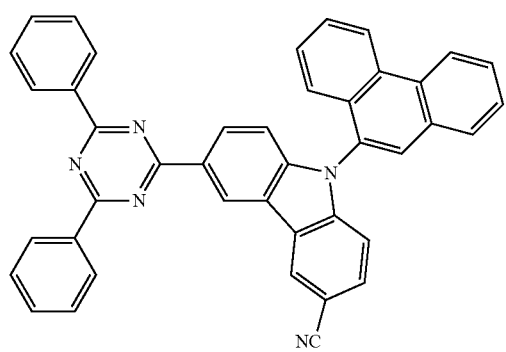
6
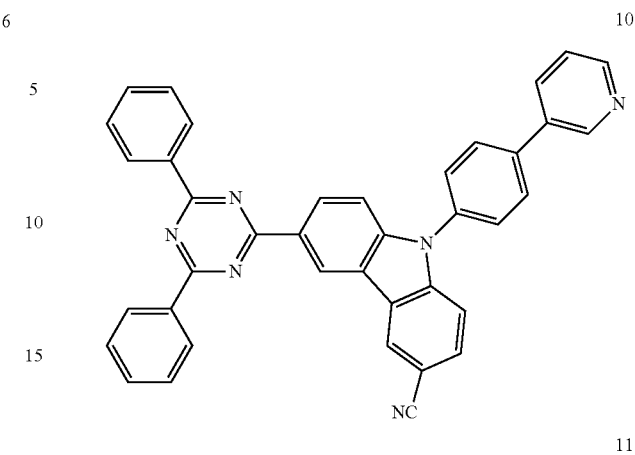
10
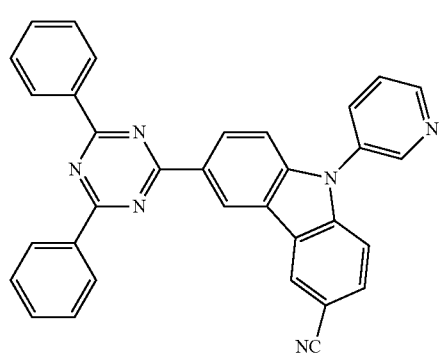
7
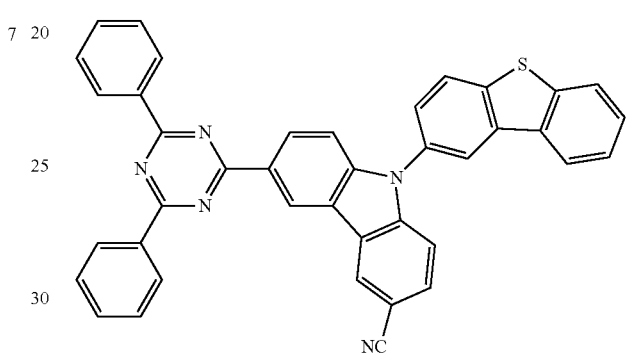
11
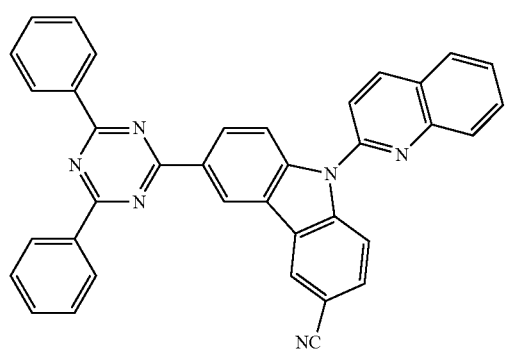
8
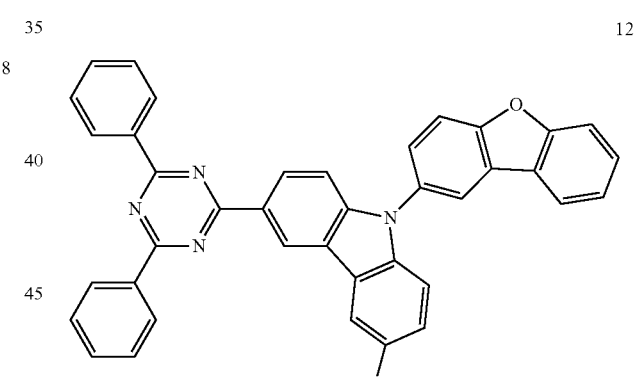
12
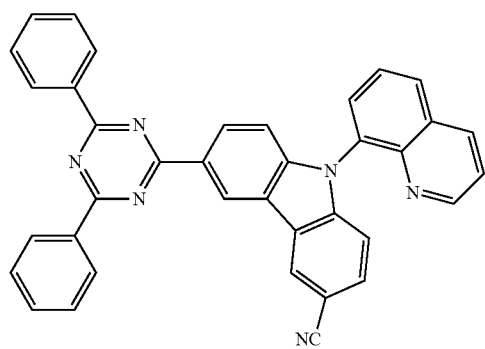
9
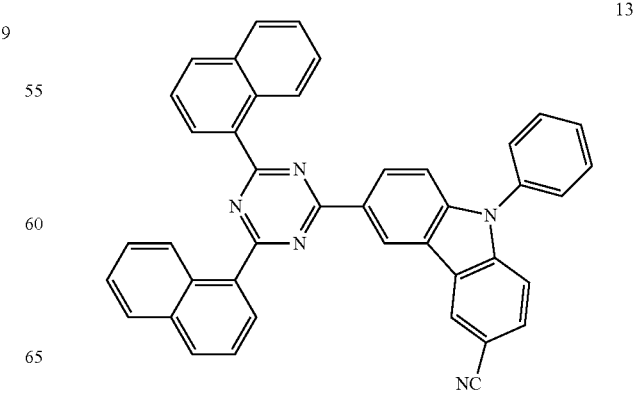
13

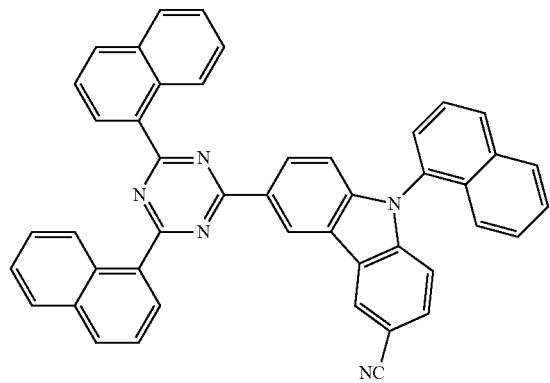
14
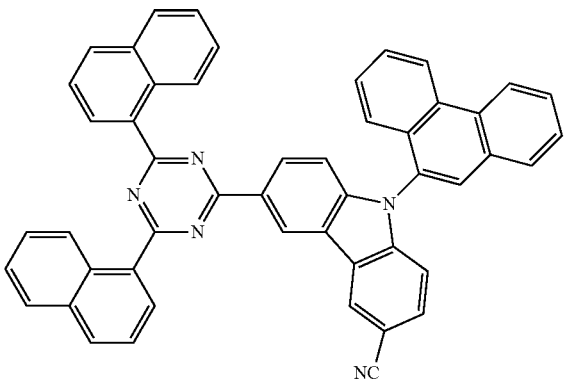
18
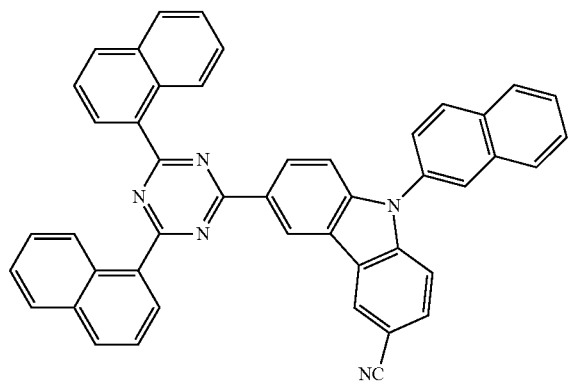
15
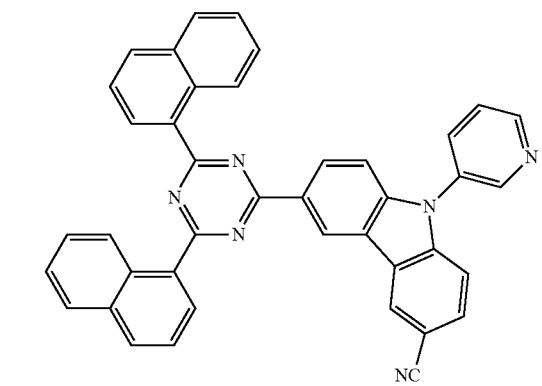
19
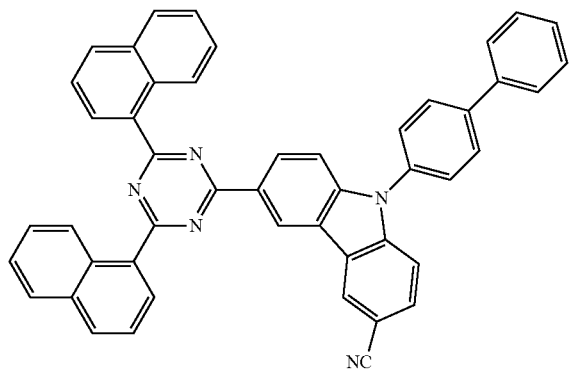
16
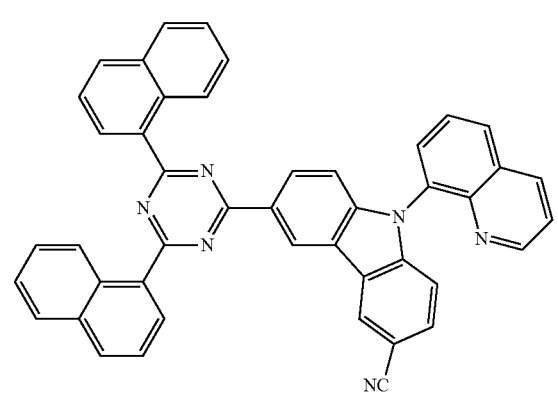 
20
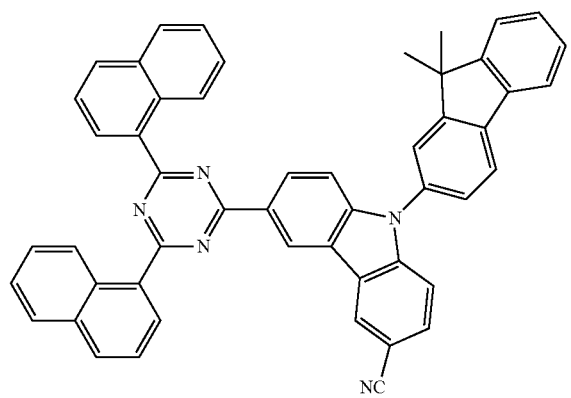
17
21

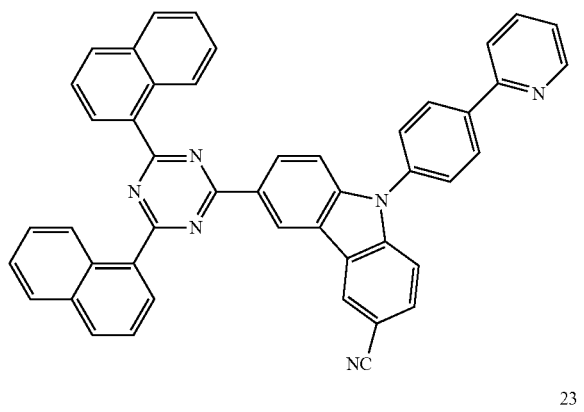
22
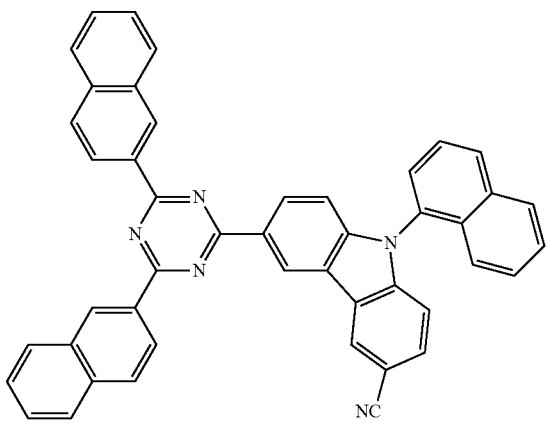
26
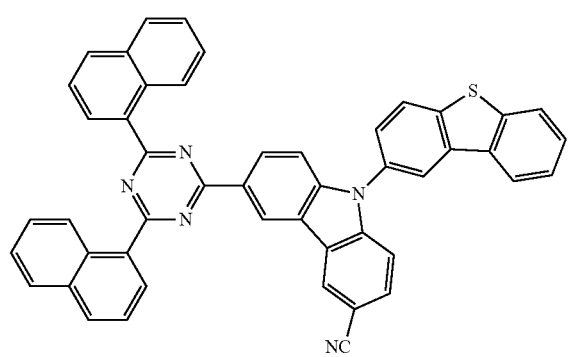
23
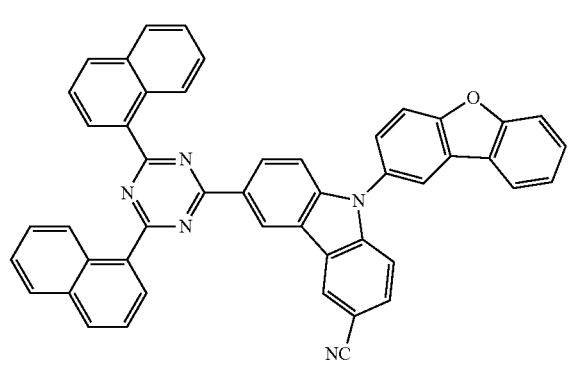
24
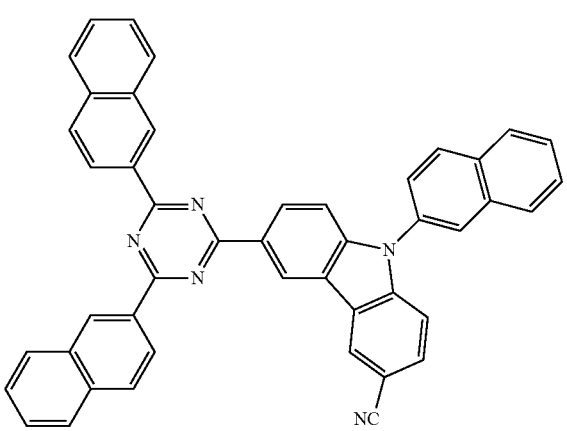
27
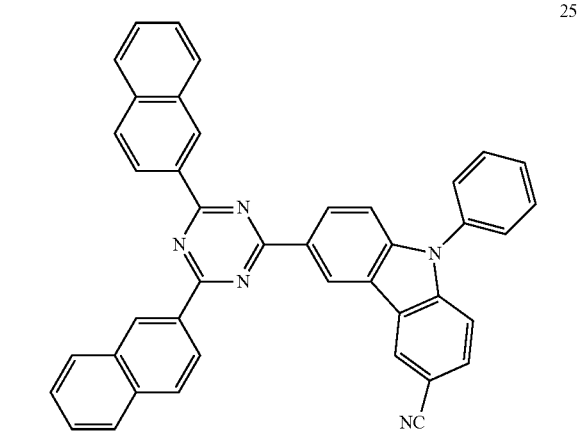
25
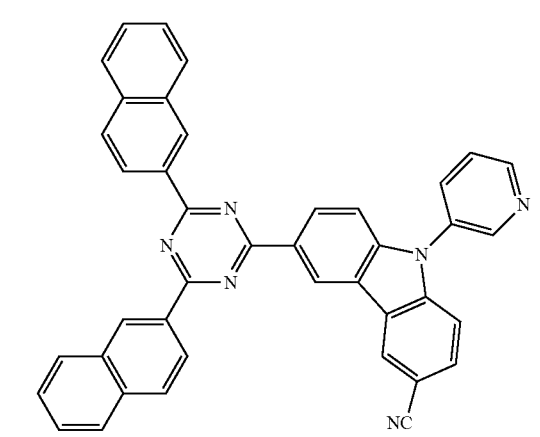
28

29
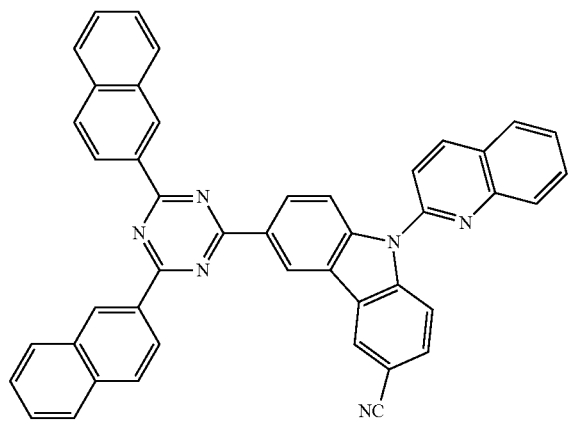
30
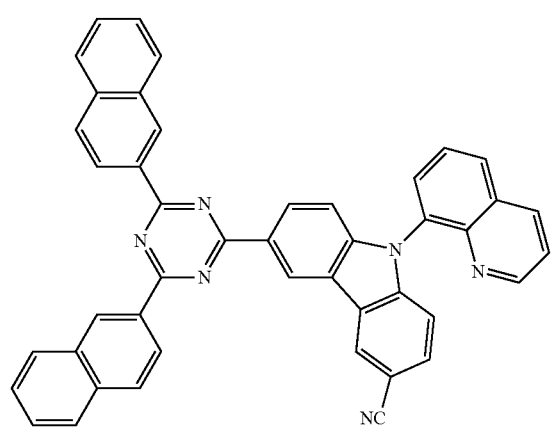
31
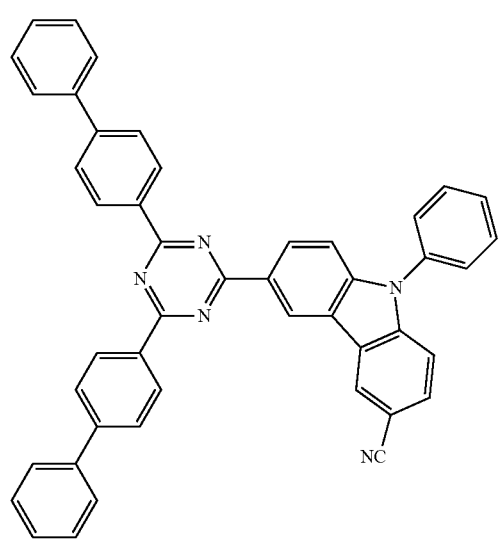
32
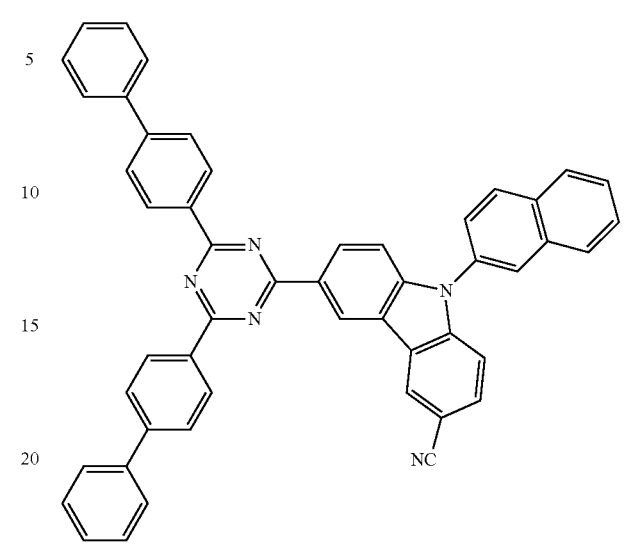
33
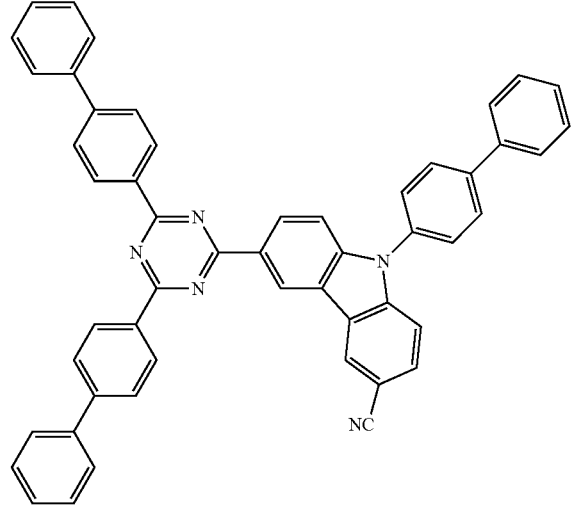
34
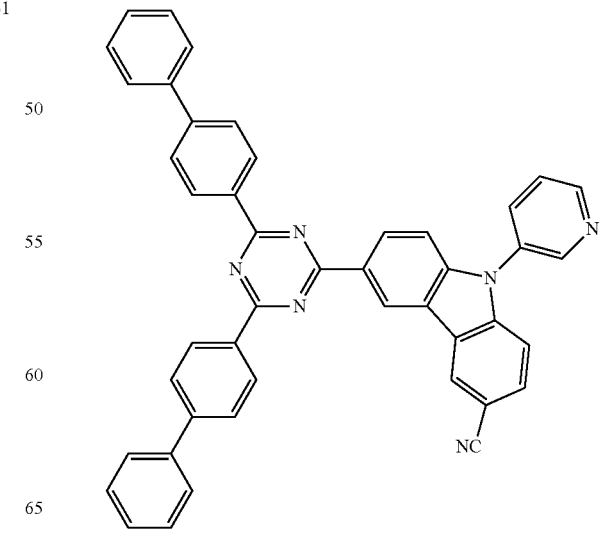

35
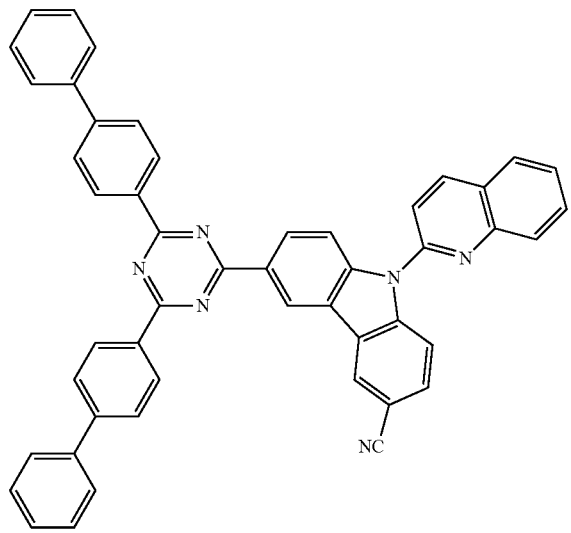
38
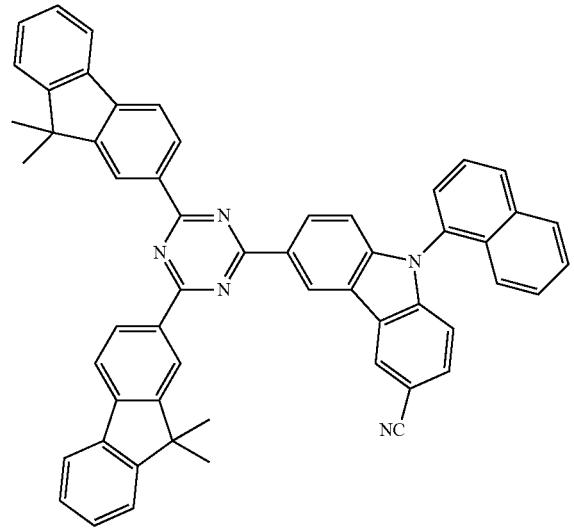
36
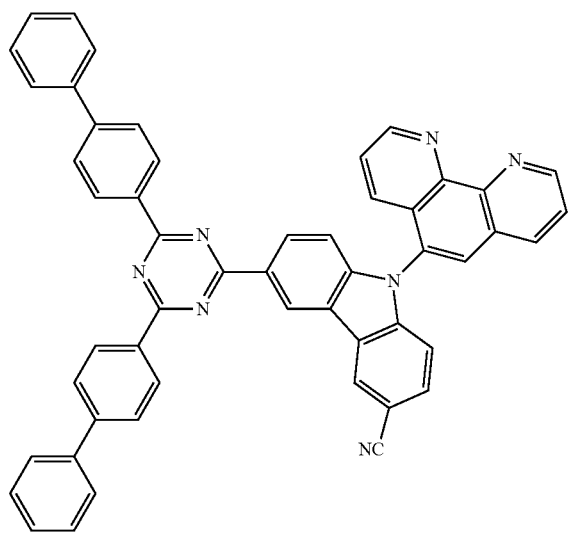
39
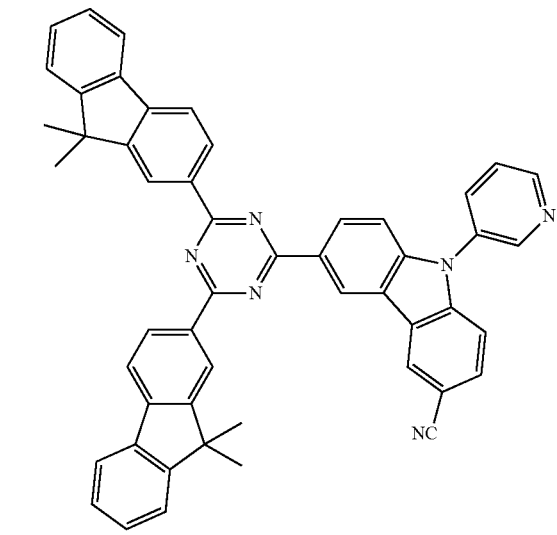
37
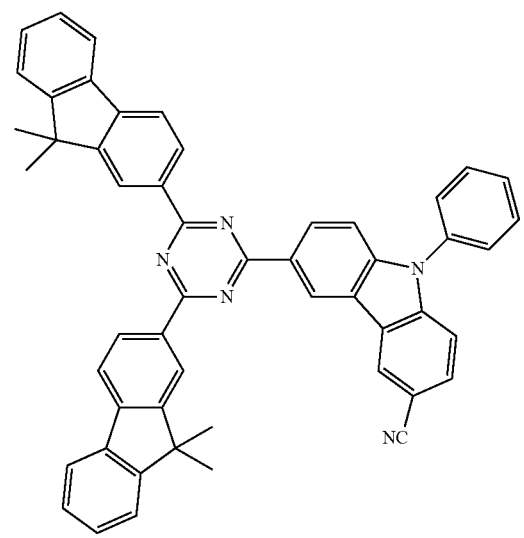
40
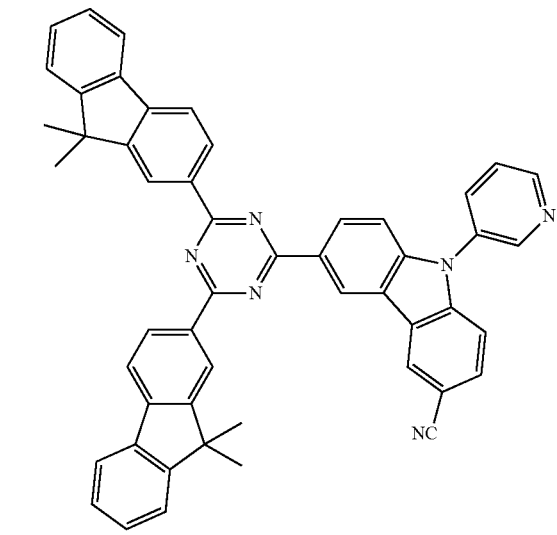

41
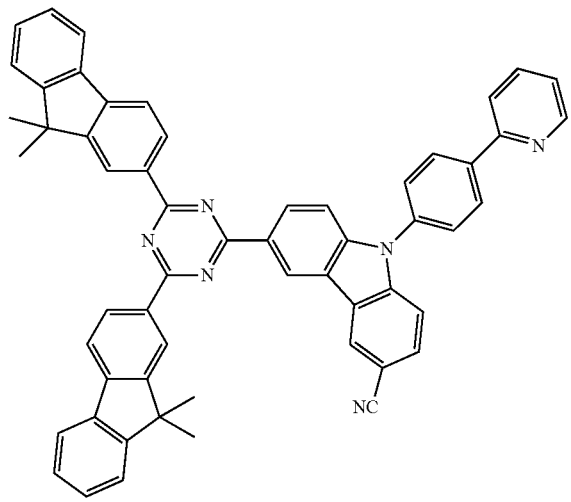
42
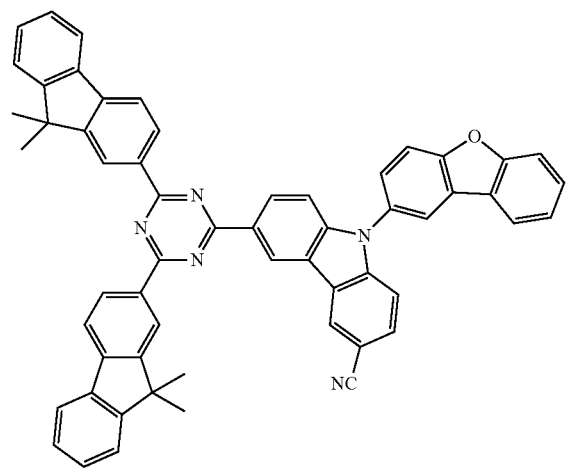
43
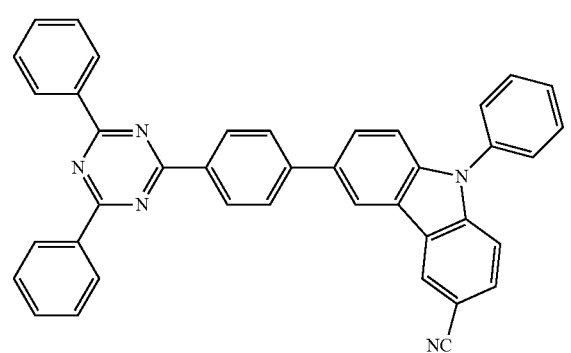
44
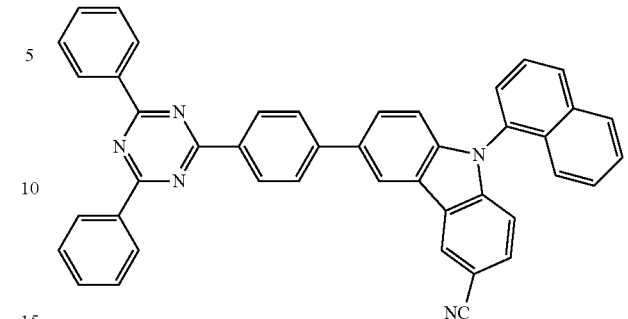
45
46
47
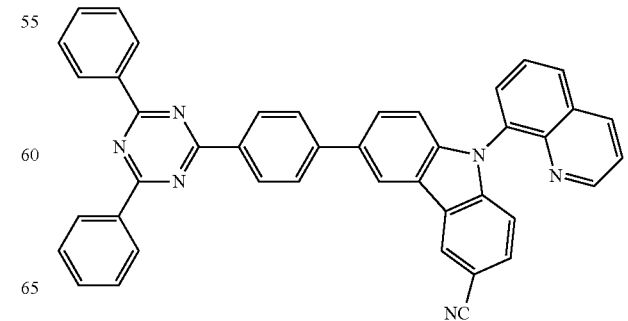

-continued
48
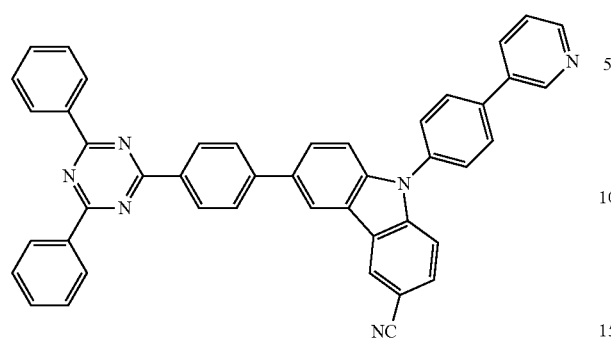
49
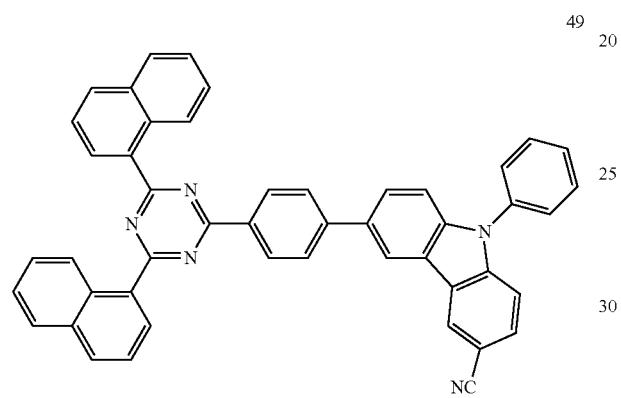
50
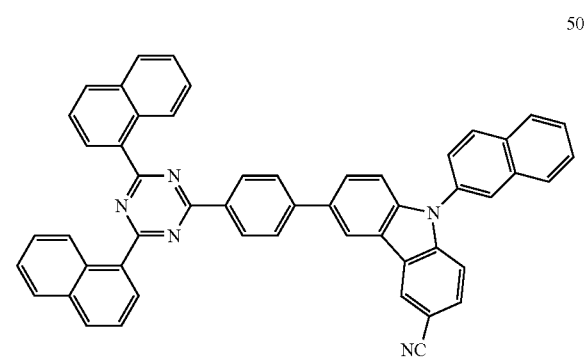
51
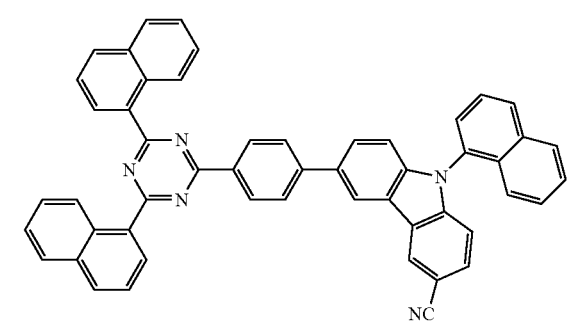
-continued
52
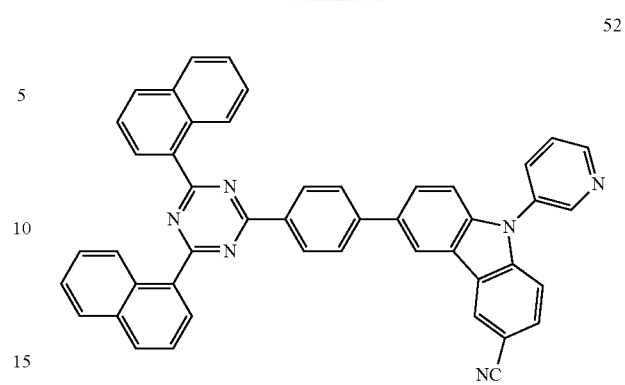
53
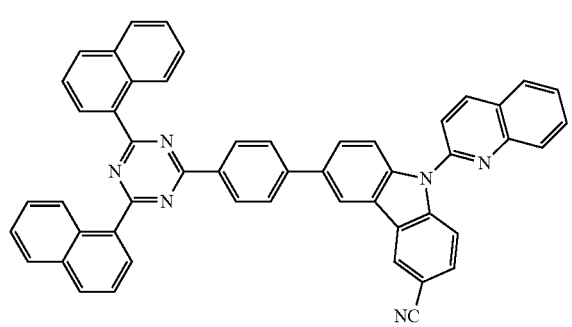
54
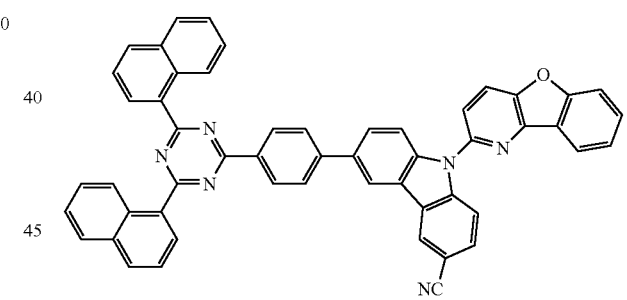
55
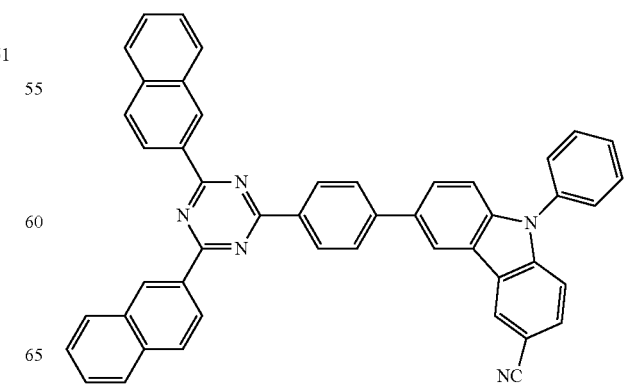

-continued
56
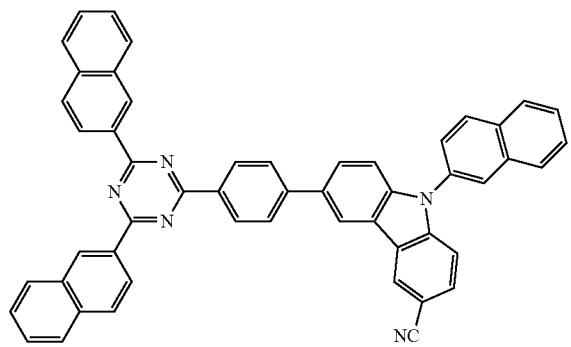
57
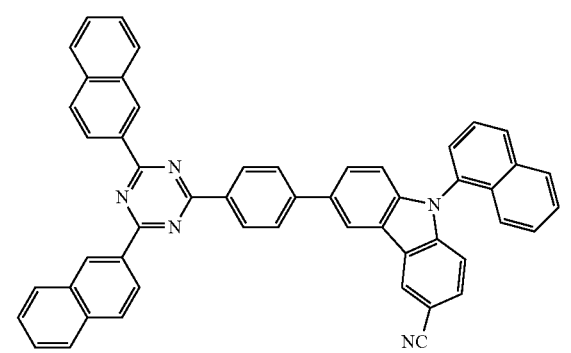
58
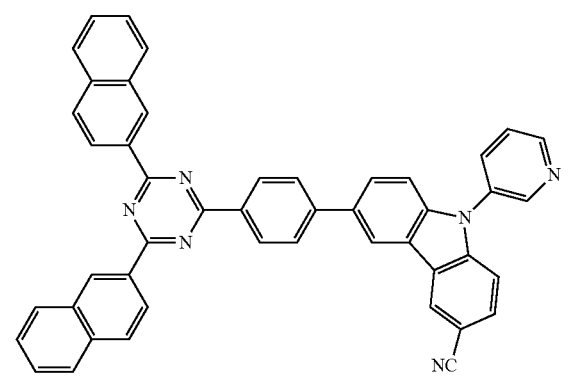
59
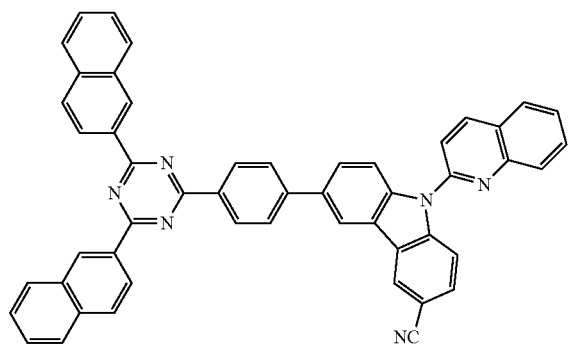
-continued
60
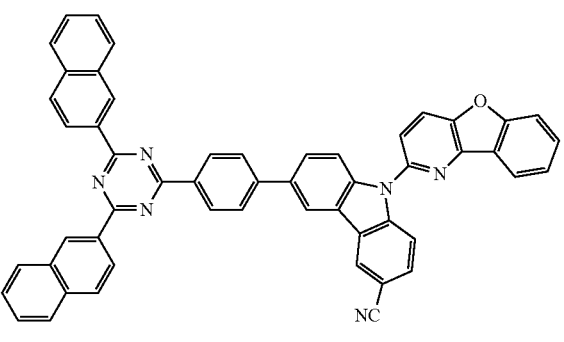
61
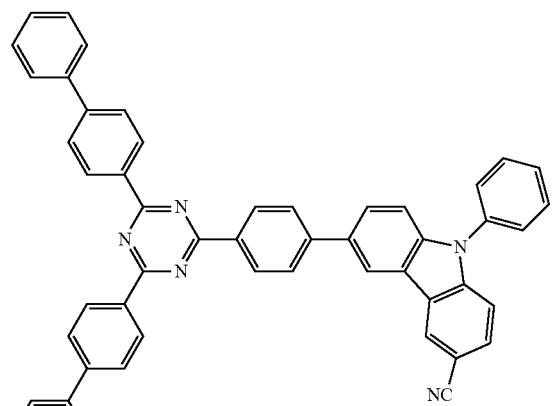
62
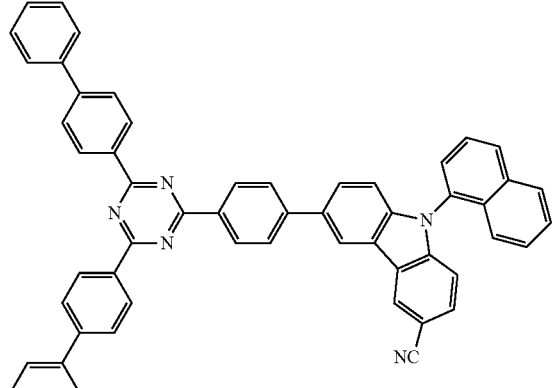

63
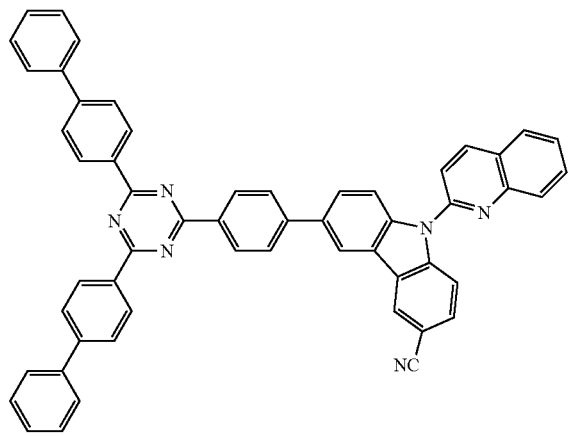
66
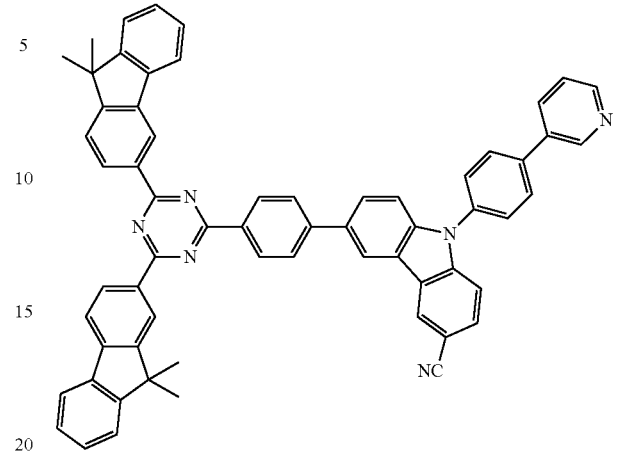
64
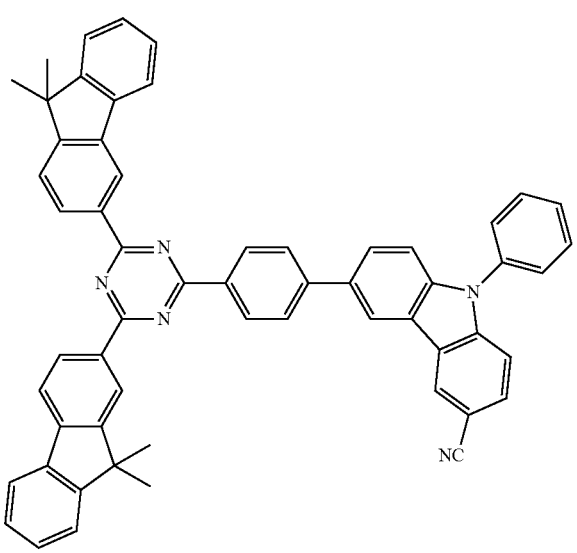
67
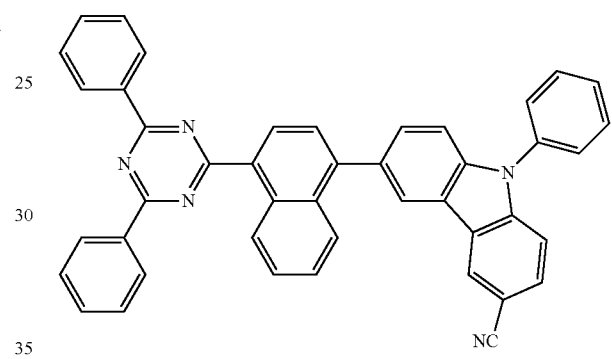
68
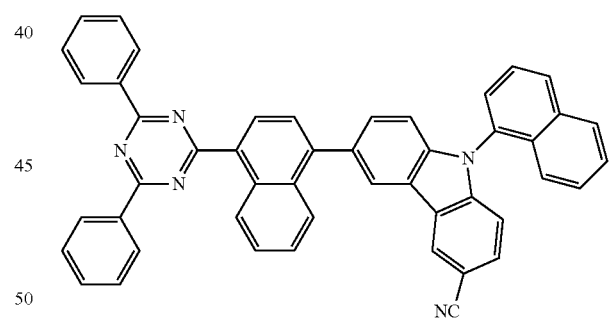
65
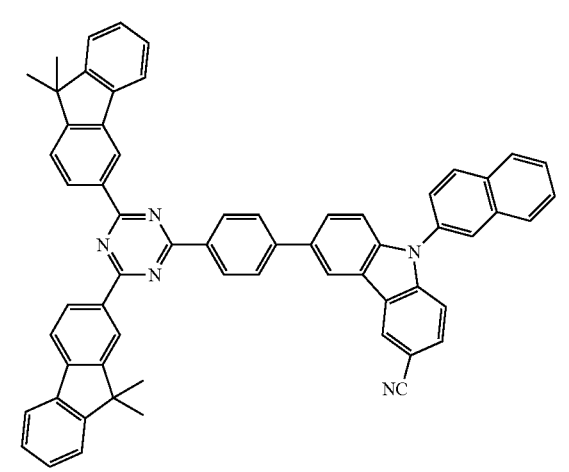
69
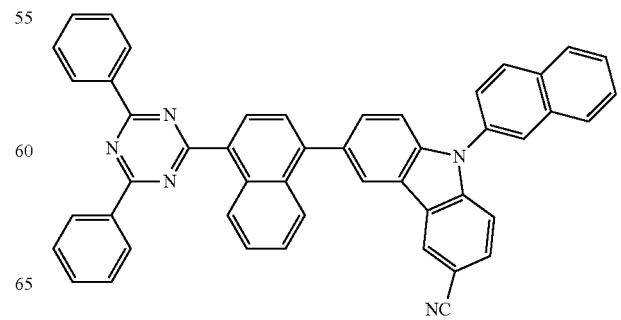

-continued
70
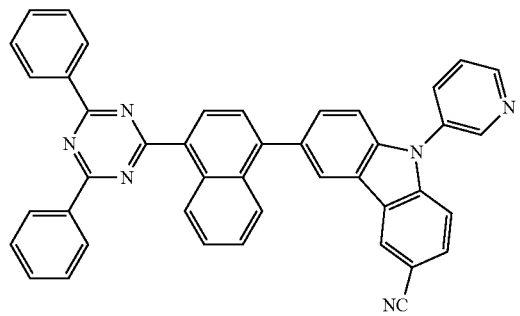
71
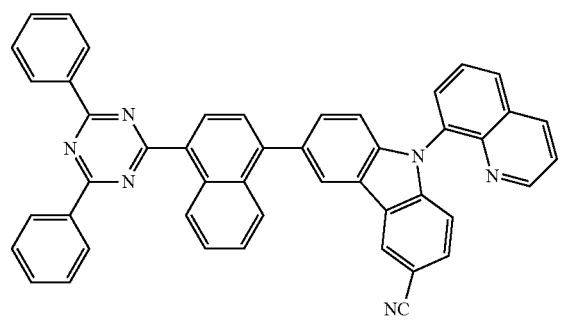
72
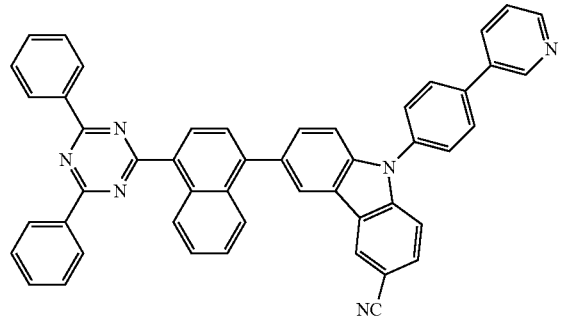
73
-continued
74
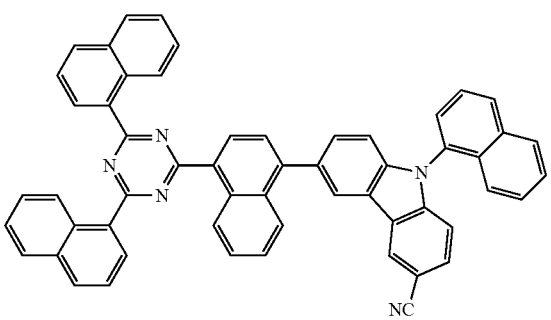
75
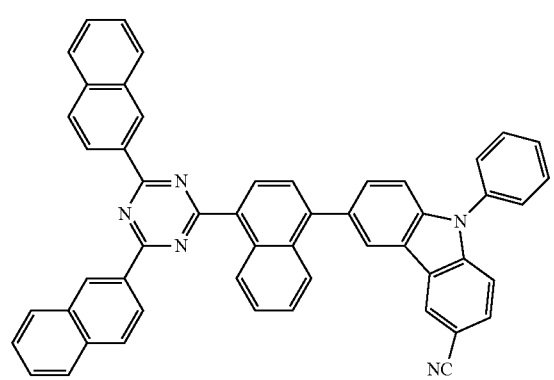
76
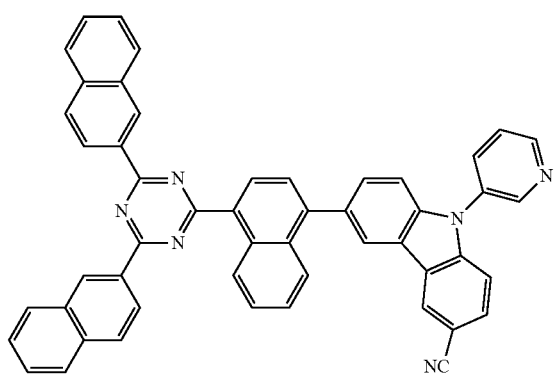
77
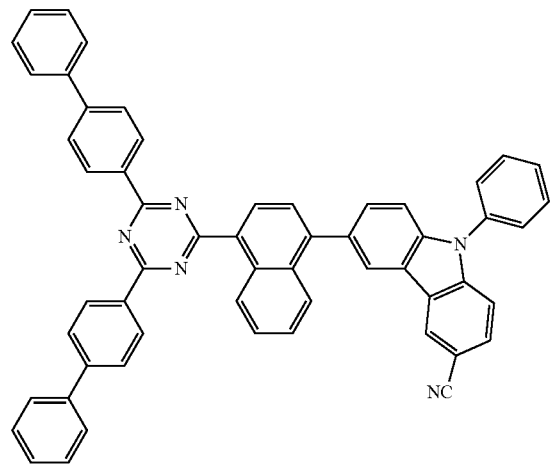

78
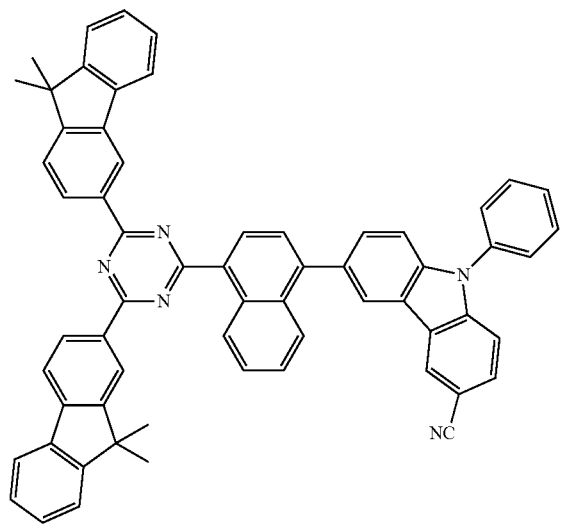
79
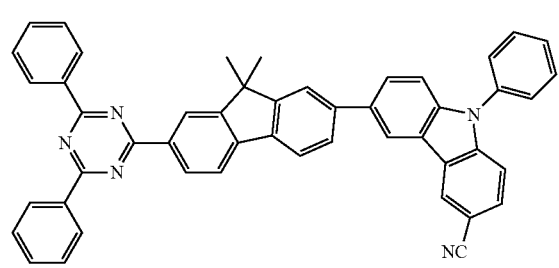
80
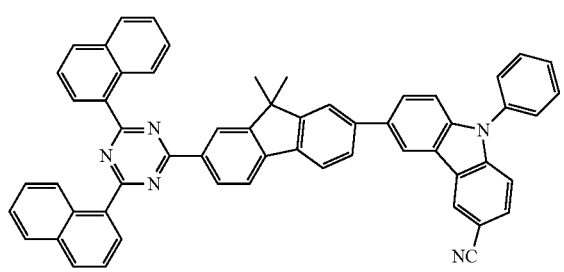
81
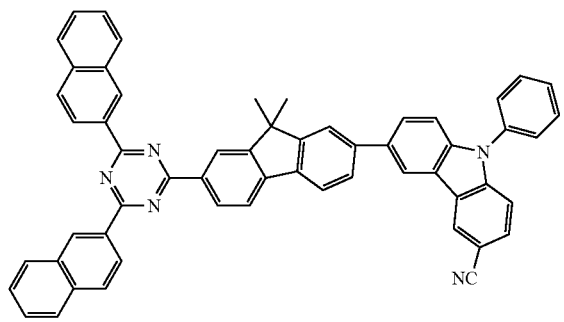
82
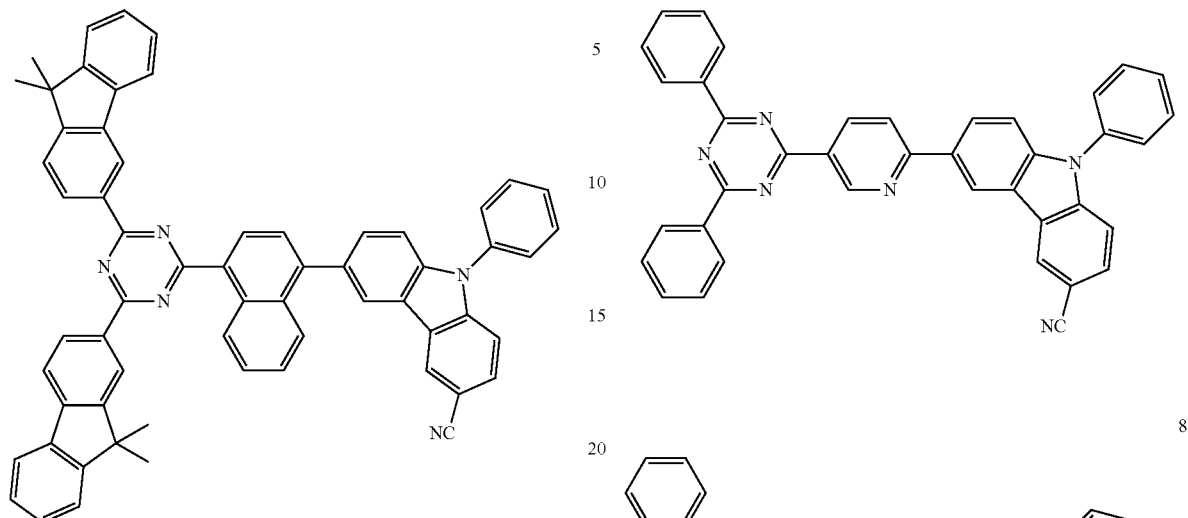
83
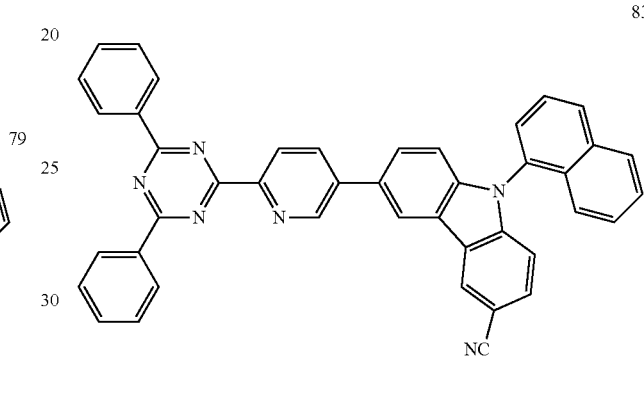
84
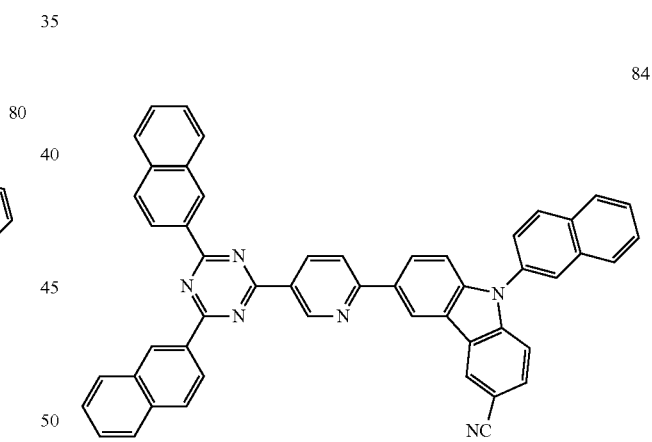
85
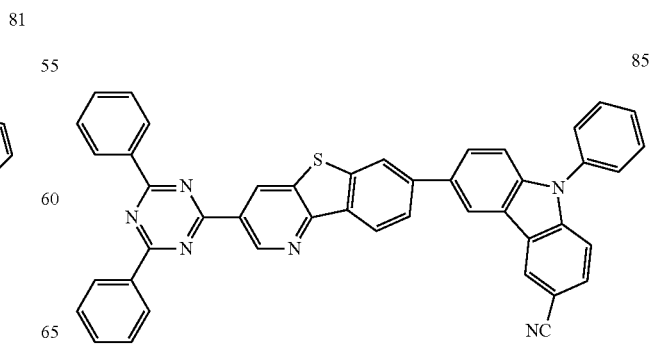

-continued
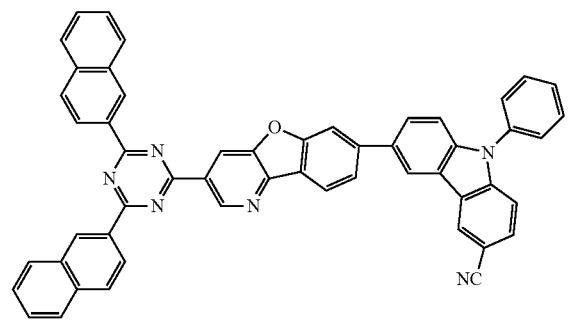
86
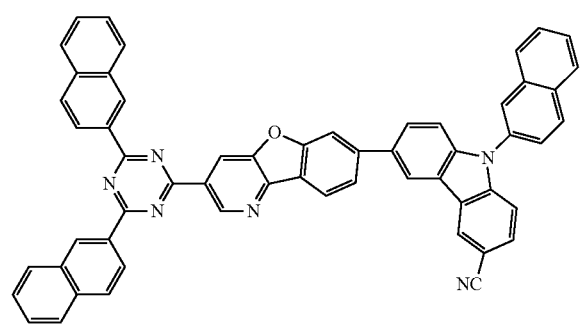
87
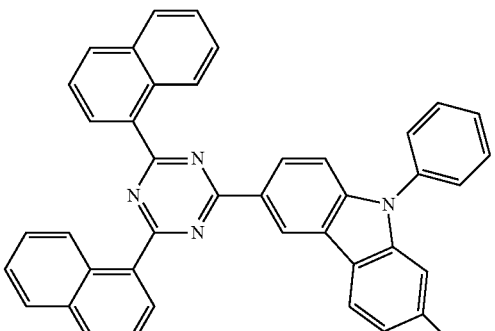
88
89
-continued
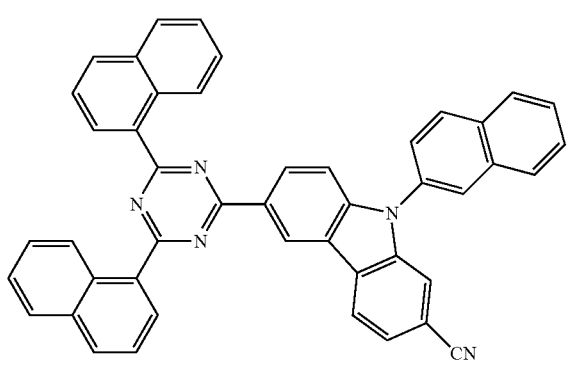
90
91
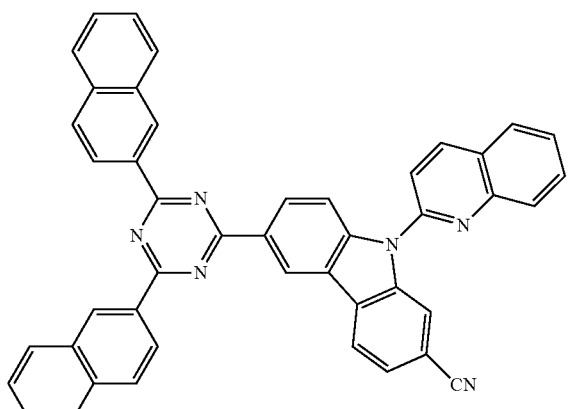
93
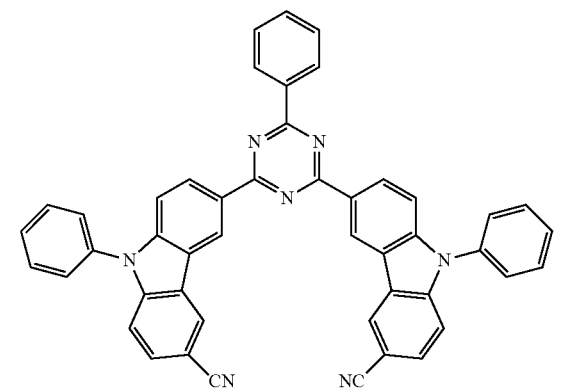
94

-continued

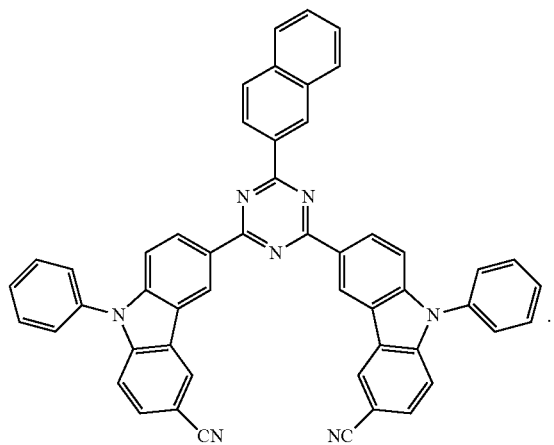

18. An organic light-emitting device comprising:
a first electrode;
a second electrode facing the first electrode; and
an organic layer between the first electrode and the second electrode, the organic layer comprising an emission layer and the triazine-based compound of claim 1.

19. The organic light-emitting device of claim 18, wherein the organic layer comprises an electron transport region between the emission layer and the second electrode, wherein the electron transport region comprises the triazine-based compound.

20. The organic light-emitting device of claim 19, wherein the electron transport region comprises an electron transporting layer comprising the triazine-based compound.

* * * * *